(12) United States Patent
Cals et al.

(10) Patent No.: US 10,118,895 B2
(45) Date of Patent: Nov. 6, 2018

(54) ROR GAMMA (RORγ) MODULATORS

(71) Applicants: LEAD PHARMA HOLDING B.V., Nijmegen (NL); SANOFI, Paris (FR)

(72) Inventors: Joseph Maria Gerardus Barbara Cals, Oss (NL); David Machnik, Paris (FR); Sander Bernardus Nabuurs, Oss (NL); Jean-Francois Sabuco, Paris (FR); Laurent Schio, Paris (FR)

(73) Assignees: LEAD PHARMA HOLDING B.V., Nijmegen (NL); SANOFI, Paris (FR)

( * ) Notice: Subject to any disclaimer, the term of this patent is extended or adjusted under 35 U.S.C. 154(b) by 0 days.

(21) Appl. No.: 15/578,997

(22) PCT Filed: Jun. 3, 2016

(86) PCT No.: PCT/EP2016/062708
§ 371 (c)(1),
(2) Date: Dec. 1, 2017

(87) PCT Pub. No.: WO2016/193468
PCT Pub. Date: Dec. 8, 2016

(65) Prior Publication Data
US 2018/0141909 A1    May 24, 2018

(30) Foreign Application Priority Data
Jun. 5, 2015 (EP) .................................... 15170768

(51) Int. Cl.
*C07D 213/71* (2006.01)
*C07D 237/18* (2006.01)
(Continued)

(52) U.S. Cl.
CPC ............ *C07D 213/71* (2013.01); *A61K 31/44* (2013.01); *A61K 31/444* (2013.01);
(Continued)

(58) Field of Classification Search
None
See application file for complete search history.

(56) References Cited

FOREIGN PATENT DOCUMENTS

| WO | 2013/029338 A1 | 3/2013 |
| WO | 2015/082533 A1 | 6/2015 |
| WO | 2015/145371 A1 | 10/2015 |

OTHER PUBLICATIONS

Jul. 13, 2016 International Search Report submitted within International Patent Application No. PCT/EP2016/062708.
Jul. 13, 2016 Written Opinion of the International Searching Authority issued in International Patent Application No. PCT/EP2016/062708.

*Primary Examiner* — Zinna Northington Davis
(74) *Attorney, Agent, or Firm* — Oliff PLC

(57) ABSTRACT

Novel compounds according to Formula I

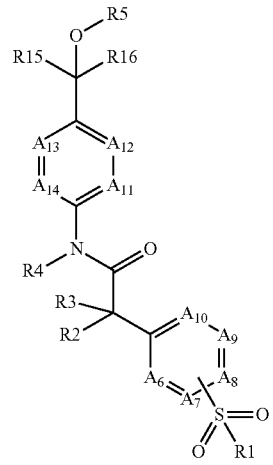

(Formula I)

Meta or para or a pharmaceutically acceptable salt thereof wherein:

$A_{11}$-$A_{14}$ are N or $CR_{11}$, $CR_{12}$, $CR_{13}$, $CR_{14}$, respectively, with the proviso that no more than two of the four positions A in $A_{11}$-$A_{14}$ can be simultaneously N; $A_6$, $A_7$, $A_8$, $A_9$, $A_{10}$ are N or $CR_6$, $CR_7$, $CR_8$, $CR_9$, $CR_{10}$, respectively, with the proviso that at least one but no more than two of the five positions A in $A_6$, $A_7$, $A_8$, $A_9$, $A_{10}$ is N; $R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino; $R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkylC(1-3)alkyl; the sulfonyl group with $R_1$ is represented by one of $R_7$, $R_8$ or $R_9$; $R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl; and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl.

10 Claims, No Drawings

(51) Int. Cl.
    *C07D 239/38*     (2006.01)
    *C07D 405/12*     (2006.01)
    *A61K 31/44*     (2006.01)
    *A61K 31/4965*     (2006.01)
    *A61K 31/50*     (2006.01)
    *A61K 31/444*     (2006.01)
    *A61K 31/4427*     (2006.01)
    *A61K 31/505*     (2006.01)
    *C07D 241/18*     (2006.01)

(52) U.S. Cl.
    CPC ...... *A61K 31/4427* (2013.01); *A61K 31/4965* (2013.01); *A61K 31/50* (2013.01); *A61K 31/505* (2013.01); *C07D 237/18* (2013.01); *C07D 239/38* (2013.01); *C07D 241/18* (2013.01); *C07D 405/12* (2013.01)

ROR GAMMA (RORγ) MODULATORS

The present invention relates to modulators of RORγ, to pharmaceutical compositions comprising the same and to the use of said compounds for the treatment of RORγ-mediated diseases or conditions, in particular autoimmune diseases and inflammatory diseases.

The retinoic-acid-receptor-related orphan receptor γt (RORγt) acts as a master regulator of the development of $T_H17$ cells, but also as a critical component in non-$T_H17$ IL-17 producing cells, such as for example γδ T-cells. The ROR gene family is part of the nuclear hormone receptor superfamily, and consists of three members (RORα, RORβ, and RORγ). Each gene is expressed in different isoforms, differing foremost in their N-terminal sequence. Two isoforms of RORγ have been identified: RORγ1 and RORγ2 (also known as RORγt). The term RORγ is used here to describe both RORγ1 and/or RORγ2.

The present invention relates to novel compounds according to Formula I

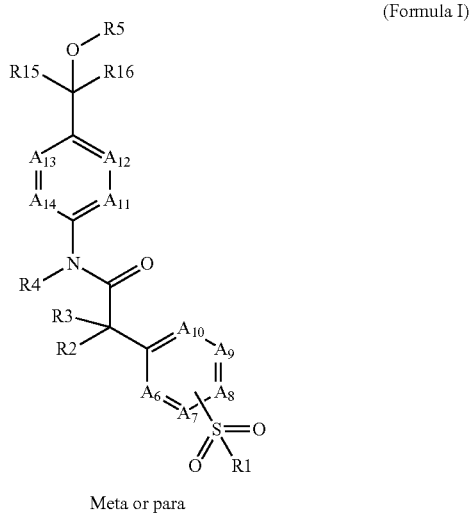

(Formula I)

Meta or para or a pharmaceutically acceptable salt thereof wherein:
$A_{11}$-$A_{14}$ are N or $CR_{11}$, $CR_{12}$, $CR_{13}$, $CR_{14}$, respectively, with the proviso that no more than two of the five positions A in $A_{11}$-$A_{14}$ can be simultaneously N;
$A_6$, $A_7$, $A_8$, $A_9$, $A_{10}$ are N or $CR_6$, $CR_7$, $CR_8$, $CR_9$, $CR_{10}$, respectively, with the proviso that at least one but no more than two of the four positions A in $A_6$, $A_7$, $A_8$, $A_9$, $A_{10}$ is N;
$R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino, with all carbon atoms of alkyl groups optionally substituted with one or more F and all carbon atoms of cycloalkyl groups optionally substituted with one or more F or methyl;
$R_2$ and $R_3$ are independently H, F, methyl, ethyl, hydroxy, methoxy or $R_2$ and $R_3$ together is carbonyl, all alkyl groups, if present, optionally being substituted with one or more F;
$R_4$ is H or C(1-6)alkyl;
$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkyl-C(1-3)alkyl, C(2-5)heterocycloalkyl or C(2-5)heterocycloalkylC(1-3)alkyl, all groups optionally substituted with one or more F, C(1-2)alkoxy or cyano;
the sulfonyl group with $R_1$ is represented by one of $R_7$, $R_8$ or $R_9$;
the remaining $R_6$-$R_{14}$ are independently H, halogen, amino, C(1-3)alkoxy, (di)C(1-3)alkylamino or C(1-6)alkyl, all of the alkyl groups optionally being substituted with one or more F; and
$R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, C(1-2)alkoxy or cyano;
and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano.

The term C(1-6)alkyl as used herein means a branched or unbranched alkyl group having 1-6 carbon atoms, for example methyl, ethyl, propyl, isopropyl, butyl, tert-butyl, n-pentyl and n-hexyl. All carbon atoms may optionally be substituted with one or more halogen.

The term C(2-6)alkyl as used herein means a branched or unbranched alkyl group having 2-6 carbon atoms, for example ethyl, propyl, isopropyl, butyl, tert-butyl, n-pentyl and n-hexyl. All carbon atoms may optionally be substituted with one or more halogen.

The term C(1-4)alkyl as used herein means an alkyl group having 1-4 carbon atoms, i.e. methyl, ethyl, propyl, isopropyl, butyl, isobutyl, sec-butyl, or tert-butyl. All carbon atoms may optionally be substituted with one or more halogen.

The term C(2-4)alkyl as used herein means an alkyl group having 2-4 carbon atoms, i.e. ethyl, propyl, isopropyl, butyl, isobutyl, sec-butyl, or tert-butyl. All carbon atoms may optionally be substituted with one or more halogen.

The term C(1-3)alkyl as used herein means an alkyl group having 1-3 carbon atoms, i.e. methyl, ethyl, propyl or isopropyl. All carbon atoms may optionally be substituted with one or more halogen.

The term C(1-2)alkyl as used herein means an alkyl group having 1-2 carbon atoms i.e. methyl or ethyl. All carbon atoms may optionally be substituted with one or more halogen.

The term C(6-10)aryl as used herein means an aromatic hydrocarbon group having 6-10 carbon atoms, for example phenyl or naphthyl. The preferred aromatic hydrocarbon group is phenyl. All carbon atoms may optionally be substituted with one or more halogen.

The term C(6-10)arylC(1-3)alkyl as used herein means an C(6-10)aryl group attached to a C(1-3)alkyl group, both with the same meaning as previously defined.

The term C(6)aryl as used herein means an aromatic hydrocarbon group having 6 carbon atoms, i.e. phenyl. All carbon atoms may optionally be substituted with one or more halogen.

The term C(6)arylC(1-3)alkyl as used herein means an C(6)aryl group attached to a C(1-3)alkyl group, both with the same meaning as previously defined.

The term heteroatom as used herein refers to a nitrogen, sulphur or oxygen atom.

The term C(1-9)heteroaryl as used herein means an aromatic group having 1-9 carbon atoms and 1-4 heteroatoms, which may be attached via a nitrogen atom if feasible, or a carbon atom. Examples include imidazolyl, thiadiazolyl, pyridinyl, pyrimidinyl, furyl, pyrazolyl, isoxazolyl, tetrazolyl and quinolyl. All carbon atoms may optionally be substituted with one or more halogen or methyl.

The term C(1-9)heteroarylC(1-3)alkyl as used herein means an C(1-9)heteroaryl group attached to a C(1-3)alkyl group, both with the same meaning as previously defined.

The term C(3-6)cycloalkyl as used herein means a saturated cyclic hydrocarbon having 3-6 carbon atoms, i.e. cyclopropyl, cyclobutyl, cyclopentyl or cyclohexyl. All carbon atoms may optionally be substituted with one or more halogen or methyl.

The term C(3-5)cycloalkyl as used herein means a saturated cyclic hydrocarbon having 3-5 carbon atoms, i.e. cyclopropyl, cyclobutyl or cyclopentyl. All carbon atoms may optionally be substituted with one or more halogen or methyl.

The term C(3-4)cycloalkyl as used herein means a saturated cyclic hydrocarbon having 3-4 carbon atoms, i.e. cyclopropyl or cyclobutyl. All carbon atoms may optionally be substituted with one or more halogen or methyl.

The term C(3-6)cycloalkylC(1-3)alkyl as used herein means an C(3-6)cycloalkyl group attached to an C(1-3)alkyl group, both with the same meaning as previously defined. An example is cyclopropylmethyl.

The term C(3-5)cycloalkylC(1-3)alkyl as used herein means an C(3-5)cycloalkyl group attached to an C(1-3)alkyl group, both with the same meaning as previously defined.

The term cyclopropylmethyl as used herein means a methyl group substituted with cyclopropyl. All carbon atoms are optionally substituted with one or more halogen or methyl.

The term C(2-5)heterocycloalkyl as used herein means a saturated cyclic hydrocarbon having 2-5 carbon atoms and 1-3 heteroatoms, which may be attached via a nitrogen atom if feasible, or a carbon atom. Examples include piperazinyl, pyrazolidilyl, piperidinyl, morpholinyl and pyrrolidinyl. All carbon atoms may optionally be substituted with one or more halogen or methyl.

The term C(2-5)heterocycloalkylC(1-3)alkyl as used herein means an C(2-5)heterocycloalkyl group attached to an C(1-3)alkyl group, both with the same meaning as previously defined.

The term amino as used herein refers to an $NH_2$ group.

The term (di)C(1-6)alkylamino as used herein means an amino group, which is monosubstituted or disubstituted with a C(1-6)alkyl group, the latter having the same meaning as previously defined.

It is to be understood that in the (di)C(1-6)alkylamino groups containing two C(1-6)alkyl groups, one of the C(1-6)alkyl groups can be replaced by a C(3-6)cycloalkyl group as previously defined.

The term (di)C(1-3)alkylamino as used herein means an amino group, which is monosubstituted or disubstituted with a C(1-3)alkyl group, the latter having the same meaning as previously defined.

The term (di)C(1-2)alkylamino as used herein means an amino group, which is monosubstituted or disubstituted with a C(1-2)alkyl group, the latter having the same meaning as previously defined. An example is dimethylamino.

The term (di)C(3-6)cycloalkylamino as used herein means an amino group, which is monosubstituted or disubstituted with a C(3-6)cycloalkyl group, the latter having the same meaning as previously defined. An example is cyclopropylamino.

The term (di)C(3-4)cycloalkylamino as used herein means an amino group, which is monosubstituted or disubstituted with a C(3-4)cycloalkyl group, the latter having the same meaning as previously defined.

The term cyclopropylamino means an amino group substituted with cyclopropyl. All carbon atoms may optionally be substituted with one or more halogen or methyl.

The term (di)(C(3-6)cycloalkylC(1-3)alkyl)amino as used herein means an amino group, which is monosubstituted or disubstituted with a C(3-6)cycloalkylC(1-3)alkyl group as previously defined.

It is to be understood that in the (di)(C(3-6)cycloalkylC(1-3)alkyl)amino groups containing two C(3-6)cycloalkylC(1-3)alkyl groups, one of the C(3-6)cycloalkylC(1-3)alkyl groups can be replaced by a C(1-6)alkyl or a C(3-6)cycloalkyl group, both as previously defined.

The term C(1-3)alkoxy means an alkoxy group having 1-3 carbon atoms, the alkyl moiety being branched or unbranched. All carbon atoms are optionally substituted with one or more F.

The term C(1-2)alkoxy means an alkoxy group having 1-2 carbon atoms. Preferred is methoxy. All carbon atoms may optionally be substituted with one or more F.

The term halogen as used herein means Cl or F.

In the above definitions with multifunctional groups, the attachment point is at the last group.

When, in the definition of a substituent, is indicated that "all of the alkyl groups" of said substituent are optionally substituted, this also includes the alkyl moiety of an alkoxy group.

The term "substituted" means that one or more hydrogens on the designated atom/atoms is/are replaced with a selection from the indicated group, provided that the designated atom's normal valency under the existing circumstances is not exceeded, and that the substitution results in a stable compound. Combinations of substituents and/or variables are permissible only if such combinations result in stable compounds. "Stable compound" or "stable structure" is defined as a compound or structure that is sufficiently robust to survive isolation to a useful degree of purity from a reaction mixture, and formulation into an efficacious therapeutic agent.

The term "optionally substituted" means optional substitution with the specified groups, radicals or moieties.

The term pharmaceutically acceptable salt represents those salts which are, within the scope of medical judgment, suitable for use in contact for the tissues of humans and lower animals without undue toxicity, irritation, allergic response and the like, and are commensurate with a reasonable benefit/risk ratio. Pharmaceutically acceptable salts are well known in the art. They may be obtained during the final isolation and purification of the compounds of the invention, or separately by reacting the free base function with a suitable mineral acid such as hydrochloric acid, phosphoric acid, or sulfuric acid, or with an organic acid such as for example ascorbic acid, citric acid, tartaric acid, lactic acid, maleic acid, malonic acid, fumaric acid, glycolic acid, succinic acid, propionic acid, acetic acid, methanesulfonic acid, and the like. The acid function can be reacted with an organic or a mineral base, like sodium hydroxide, potassium hydroxide or lithium hydroxide.

In one embodiment the invention also relates to a compound according to Formula I wherein:
$A_{11}$-$A_{14}$ are N or $CR_{11}$, $CR_{12}$, $CR_{13}$, $CR_{14}$, respectively, with the proviso that no more than two of the four positions A in $A_{11}$-$A_{14}$ can be simultaneously N;
$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is C(3-6)cycloalkylC(1-3)alkyl or (di)C(3-6)cycloalkylamino with all carbon atoms of alkyl groups optionally substituted with one or more F and all carbon atoms of cycloalkyl groups optionally substituted with one or more F or methyl;

$R_2$ and $R_3$ are independently H;

$R_4$ is H;

$R_5$ is H, hydroxyethyl, methoxyethyl, C(1-6)alkyl, C(2-5)heterocycloalkyl or C(2-5)heterocycloalkylC(1-3)alkyl, all groups optionally substituted with one or more F, C(1-2)alkoxy or cyano;

the sulfonyl group with $R_1$ is represented by $R_8$;

the remaining $R_6$-$R_{14}$ are independently H, halogen, C(1-3)alkoxy or C(1-6)alkyl, all of the alkyl groups optionally being substituted with one or more F; and $R_{15}$ is C(1-6)alkyl, or C(3-6)cycloalkyl, all groups optionally substituted with one or more F, C(1-2)alkoxy or cyano;

and $R_{16}$ is C(1-6)alkyl, C(3-6)cycloalkyl, C(3-6)cycloalkylC(1-3)alkyl, C(6-10)aryl, C(2-5)heterocycloalkyl or C(2-5)heterocycloalkyl-C(1-3)alkyl, all groups optionally substituted with one or more F, C(1-2)alkoxy or cyano.

In one embodiment the invention also relates to a compound according to Formula I wherein:

$A_{11}$-$A_{14}$ are respectively $CR_{11}$, $CR_{12}$, $CR_{13}$, $CR_{14}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is C(3-6)cycloalkylC(1-3)alkyl or (di)C(3-6)cycloalkylamino with all carbon atoms of alkyl groups optionally substituted with one or more F and all carbon atoms of cycloalkyl groups optionally substituted with one or more F or methyl;

$R_2$ and $R_3$ are independently H;

$R_4$ is H;

$R_5$ is H, hydroxyethyl, methoxyethyl, C(1-6)alkyl, C(2-5)heterocycloalkyl or C(2-5)heterocycloalkylC(1-3)alkyl, all groups optionally substituted with one or more F, C(1-2)alkoxy or cyano;

the sulfonyl group with $R_1$ is represented by $R_8$;

the remaining $R_6$-$R_{14}$ are independently H, halogen, C(1-3)alkoxy or C(1-6)alkyl, all of the alkyl groups optionally being substituted with one or more F; and $R_{15}$ is C(1-6)alkyl or C(3-6)cycloalkyl, all groups optionally substituted with one or more F, C(1-2)alkoxy or cyano;

and $R_{16}$ is C(1-6)alkyl, C(3-6)cycloalkyl, C(3-6)cycloalkylC(1-3)alkyl, C(6-10)aryl, C(2-5)heterocycloalkyl or C(2-5)heterocycloalkyl-C(1-3)alkyl, all groups optionally substituted with one or more F, C(1-2)alkoxy or cyano.

In one embodiment the invention also relates to a compound according to Formula I wherein:

$A_{11}$ or $A_{14}$ is N, the remaining position A being $CR_{11}$ or $CR_{14}$;

$A_{12}$ and $A_{13}$ are respectively $CR_{12}$ and $CR_{13}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is C(3-6)cycloalkylC(1-3)alkyl or (di)C(3-6)cycloalkylamino with all carbon atoms of alkyl groups optionally substituted with one or more F and all carbon atoms of cycloalkyl groups optionally substituted with one or more F or methyl;

$R_2$ and $R_3$ are independently H;

$R_4$ is H;

$R_5$ is H, hydroxyethyl, methoxyethyl, C(1-6)alkyl, C(2-5)heterocycloalkyl or C(2-5)heterocycloalkylC(1-3)alkyl, all groups optionally substituted with one or more F, C(1-2)alkoxy or cyano;

the sulfonyl group with $R_1$ is represented by $R_8$;

the remaining $R_6$-$R_{14}$ are independently H, halogen, C(1-3)alkoxy or C(1-6)alkyl, all of the alkyl groups optionally being substituted with one or more F; and $R_{15}$ is C(1-6)alkyl, or C(3-6)cycloalkyl, all groups optionally substituted with one or more F, C(1-2)alkoxy or cyano;

and $R_{16}$ is C(1-6)alkyl, C(3-6)cycloalkyl, C(3-6)cycloalkylC(1-3)alkyl, C(6-10)aryl, C(2-5)heterocycloalkyl or C(2-5)heterocycloalkyl-C(1-3)alkyl, all groups optionally substituted with one or more F, C(1-2)alkoxy or cyano.

In one embodiment the invention also relates to a compound according to Formula I wherein:

$A_{11}$-$A_{14}$ are respectively $CR_{11}$, $CR_{12}$, $CR_{13}$, $CR_{14}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is C(3-6)cycloalkylC(1-3)alkyl, all carbon atoms of cycloalkyl group optionally substituted with one or more F or methyl;

$R_2$ and $R_3$ are independently H;

$R_4$ is H;

$R_5$ is H, hydroxyethyl, methoxyethyl, C(1-6)alkyl or C(2-5)heterocycloalkylC(1-3)alkyl;

the sulfonyl group with $R_1$ is represented by $R_8$;

the remaining $R_6$-$R_{14}$ are independently H, halogen, C(1-3)alkoxy or C(1-6)alkyl;

$R_{15}$ is C(1-6)alkyl or C(3-6)cycloalkyl, all carbon atoms of the alkyl groups optionally substituted with one or more F;

and $R_{16}$ is C(1-6)alkyl, C(3-6)cycloalkyl, C(3-6)cycloalkylC(1-3)alkyl or C(6-10)aryl, all carbon atoms of the alkyl group optionally substituted with one or more F.

In one embodiment the invention also relates to a compound according to Formula I wherein:

$A_{11}$-$A_{14}$ are respectively $CR_{11}$, $CR_{12}$, $CR_{13}$, $CR_{14}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is cyclopropylmethyl, all carbon atoms of cycloalkyl groups optionally substituted with one or more F or methyl;

$R_2$ and $R_3$ are independently H;

$R_4$ is H;

$R_5$ is H, hydroxyethyl, methoxyethyl, methyl, isopropyl or oxetanylmethyl;

the sulfonyl group with $R_1$ is represented by $R_8$;

the remaining $R_6$-$R_{14}$ are independently H, Cl, F, methoxy, methyl or hydroxymethyl;

$R_{15}$ is $CF_3$ or cyclopropyl;

and $R_{16}$ is methyl, ethyl, $CF_3$, propyl, isobutyl, 3-methylbutyl, cyclopropyl, cyclopentyl, cyclopentylmethyl, cyclohexylmethyl or phenyl.

In one embodiment the invention also relates to a compound according to Formula I wherein:

$A_{11}$ or $A_{14}$ is N, the remaining position A being $CR_{11}$ or $CR_{14}$;

$A_{12}$ and $A_{13}$ are respectively $CR_{12}$ and $CR_{13}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is C(3-6)cycloalkylC(1-3)alkyl;

$R_2$ and $R_3$ are independently H;

$R_4$ is H;

$R_5$ is H;

the sulfonyl group with $R_1$ is represented by $R_8$;

the remaining $R_6$-$R_{14}$ are H;

$R_{15}$ is C(1-6)alkyl, all carbon atoms of alkyl groups optionally substituted with one or more F;

and $R_{16}$ is C(1-6)alkyl, all carbon atoms of alkyl groups optionally substituted with one or more F.

In one embodiment the invention also relates to a compound according to Formula I wherein:

$A_{11}$ or $A_{14}$ is N, the remaining position A being $CR_{11}$ or $CR_{14}$;

$A_{12}$ and $A_{13}$ are respectively $CR_{12}$ and $CR_{13}$;

$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;

$A_8$ is $CR_8$;

$R_1$ is cyclopropylmethyl;

$R_2$ and $R_3$ are independently H;

$R_4$ is H;

$R_5$ is H;

the sulfonyl group with $R_1$ is represented by $R_8$;

the remaining $R_6$-$R_{14}$ are H;

$R_{15}$ is $CF_3$;

and $R_{16}$ is methyl or $CF_3$.

The invention also relates to a compound according to Formula I wherein $R_1$ is C(3-6)cycloalkylC(1-3)alkyl or (di)C(3-6)cycloalkylamino with all carbon atoms of alkyl groups optionally substituted with one or more F and all carbon atoms of cycloalkyl groups optionally substituted with one or more F or methyl;

In one embodiment the invention also relates to a compound according to Formula I wherein $R_1$ is C(3-6)cycloalkylC(1-3)alkyl with all carbon atoms of cycloalkyl groups optionally substituted with one or more F or methyl.

In one embodiment the invention also relates to a compound according to Formula I wherein $R_1$ is cyclopropylmethyl, (methylcyclopropyl)methyl, (difluorocyclopropyl)methyl.

In one embodiment the invention also relates to a compound according to Formula I wherein $R_1$ is cyclopropylmethyl.

The invention also relates to a compound according to Formula I wherein $R_2$ and $R_3$ independently are H.

The invention also relates to a compound according to Formula I wherein $R_4$ is H.

The invention also relates to a compound according to Formula I wherein $R_5$ is H, hydroxyethyl, methoxyethyl, C(1-6)alkyl or C(2-5)heterocycloalkylC(1-3)alkyl.

In another embodiment the invention also relates to a compound according to Formula I wherein $R_5$ is H, hydroxyethyl, methoxyethyl, methyl, isopropyl or oxetanylmethyl.

In another embodiment the invention also relates to a compound according to Formula I wherein $R_5$ is H or C(1-6)alkyl.

In another embodiment, $R_5$ in Formula I is H.

In another embodiment, $R_5$ in Formula I is methyl or isopropyl.

In another embodiment, $R_5$ in Formula I is hydroxyethyl.

In another embodiment, $R_5$ in Formula I is methoxyethyl.

In another embodiment, $R_5$ in Formula I is oxetanylmethyl.

The invention also relates to a compound according to Formula I wherein one of the groups $R_7$, $R_8$, $R_9$ is the sulfonyl group with $R_1$ attached to it and the others including $R_6$ and $R_{10}$ are independently H or C(1-6)alkyl.

The invention also relates to a compound according to Formula I wherein one of the groups $R_8$ is the sulfonyl group with $R_1$ attached to it and $R_6$, $R_7$, $R_9$ and $R_{10}$ are independently H or C(1-6)alkyl.

The invention also relates to a compound according to Formula I wherein one of the groups $R_8$ is the sulfonyl group with $R_1$ attached to it and $R_6$, $R_7$, $R_9$ and $R_{10}$ are independently H or methyl.

In another embodiment the sulfonyl group is represented by $R_8$, i.e. the sulfonyl group is attached at the para position of the aryl ring.

The invention also relates to a compound according to Formula I wherein $R_{11}$-$R_{14}$ are independently H, halogen, C(1-3)alkoxy or C(1-6)alkyl.

In one embodiment the invention also relates to a compound according to Formula I wherein $R_{11}$-$R_{14}$ are independently H, Cl, F, methoxy or methyl.

In one embodiment the invention also relates to a compound according to Formula I wherein $R_{11}$-$R_{14}$ are independently H.

In one embodiment the invention also relates to a compound according to Formula I wherein $R_{11}$-$R_{14}$ are independently Cl.

In one embodiment the invention also relates to a compound according to Formula I wherein $R_{11}$-$R_{14}$ are independently F.

In one embodiment the invention also relates to a compound according to Formula I wherein $R_{11}$-$R_{14}$ are independently methoxy.

In one embodiment the invention also relates to a compound according to Formula I wherein $R_{11}$-$R_{14}$ are independently methyl.

In one embodiment the invention also relates to a compound according to Formula I wherein $A_{11}$-$A_{14}$ are carbon atoms.

In one embodiment the invention also relates to a compound according to Formula I wherein $A_{11}$ or $A_{14}$ is nitrogen, the remaining position A being a carbon.

In one embodiment the invention also relates to a compound according to Formula I wherein $A_7$ or $A_9$ is N, the remaining position A being a carbon.

In one embodiment the invention also relates to a compound according to Formula I wherein $A_6$ or $A_{10}$ is N, the remaining position A being a carbon.

In one embodiment the invention also relates to a compound according to Formula I wherein $A_6$ and $A_{10}$ is N, the remaining position A being a carbon.

In one embodiment the invention also relates to a compound according to Formula I wherein $A_7$ and $A_9$ is N, the remaining position A being a carbon.

In one embodiment the invention also relates to a compound according to Formula I wherein $A_6$ and $A_9$ or $A_7$ and $A_{10}$ is N, the remaining positions A being a carbon.

In one embodiment the invention also relates to a compound according to Formula I wherein $A_6$ and $A_7$ or $A_9$ and $A_{10}$ is N, the remaining positions A being a carbon.

In one embodiment the invention also relates to a compound according to Formula I wherein $A_{11}$ or $A_{14}$ and $A_7$ or $A_9$ is N, the remaining positions A being a carbon.

The invention also relates to a compound according to Formula I wherein $R_{15}$ is C(1-6)alkyl or C(3-6)cycloalkyl, all groups optionally substituted with one or more F, C(1-2)alkoxy or cyano;

and $R_{16}$ is C(1-6)alkyl, C(3-6)cycloalkyl, C(3-6)cycloalkylC(1-3)alkyl, C(6-10)aryl, C(2-5)heterocycloalkyl or C(2-5)heterocycloalkyl-C(1-3)alkyl, all groups optionally substituted with one or more F, C(1-2)alkoxy or cyano.

In one embodiment the invention also relates to a compound according to Formula I wherein $R_{15}$ is C(1-6)alkyl or C(3-6)cycloalkyl, all groups optionally substituted with one or more F;

and $R_{16}$ is C(1-6)alkyl, C(3-6)cycloalkyl, C(3-6)cycloalkylC(1-3)alkyl or C(6-10)aryl, all groups optionally substituted with one or more F.

In one embodiment the invention also relates to a compound according to Formula I wherein $R_{15}$ is $CF_3$ or cyclopropyl;

and $R_{16}$ is methyl, $CF_3$, ethyl, propyl, isobutyl, 3-methylbutyl, cyclopropyl, cyclopentyl, cyclopentylmethyl, cyclohexylmethyl or phenyl.

In one embodiment the invention also relates to a compound according to Formula I wherein $R_{15}$ and $R_{16}$ are both $CF_3$.

In one embodiment the invention also relates to a compound according to Formula I wherein either $R_{15}$ or $R_{16}$ is $CF_3$.

In one embodiment the invention also relates to a compound according to Formula I wherein $R_{15}$ is $CF_3$ and $R_{16}$ is C(1-6)alkyl, C(3-6)cycloalkyl, C(3-6)cycloalkylC(1-3)alkyl or C(6-10)aryl, all groups optionally substituted with one or more F.

In one embodiment the invention also relates to a compound according to Formula I wherein $R_{15}$ is $CF_3$ and $R_{16}$ is methyl, $CF_3$, ethyl, propyl, isobutyl, 3-methylbutyl, cyclopropyl, cyclopentyl, cyclopentylmethyl, cyclohexylmethyl or phenyl.

In one embodiment the invention also relates to a compound according to Formula I wherein $R_{15}$ is $CF_3$ and $R_{16}$ is C(1-6)alkyl with all carbon atoms of the alkyl groups optionally substituted with one or more F.

In one embodiment the invention also relates to a compound according to Formula I wherein $R_{15}$ is $CF_3$ and $R_{16}$ is methyl, $CF_3$, ethyl, propyl, isobutyl or 3-methylbutyl.

In one embodiment the invention also relates to a compound according to Formula I wherein $R_{15}$ is $CF_3$ and $R_{16}$ is C(3-6)cycloalkyl.

In one embodiment the invention also relates to a compound according to Formula I wherein $R_{15}$ is $CF_3$ and $R_{16}$ is cyclopropyl or cyclopentyl.

In one embodiment the invention also relates to a compound according to Formula I wherein $R_{15}$ is $CF_3$ and $R_{16}$ is C(3-6)cycloalkylC(1-3)alkyl.

In one embodiment the invention also relates to a compound according to Formula I wherein $R_{15}$ is $CF_3$ and $R_{16}$ is cyclopentylmethyl or cyclohexylmethyl.

In one embodiment the invention also relates to a compound according to Formula I wherein $R_{15}$ is $CF_3$ and $R_{16}$ is C(6-10)aryl.

In one embodiment the invention also relates to a compound according to Formula I wherein $R_{15}$ is $CF_3$ and $R_{16}$ is phenyl.

The invention also relates to a compound according to Formula I wherein $R_5$ is H, $R_{15}$ is $CF_3$ and $R_{16}$ is C(1-6)alkyl, C(3-6)cycloalkyl, C(3-6)cycloalkylC(1-3)alkyl or C(6-10)aryl, with all carbon atoms of the alkyl groups optionally substituted with one or more F.

In one embodiment the invention also relates to a compound according to Formula I wherein $R_5$ is H, $R_{15}$ is $CF_3$ and $R_{16}$ is methyl, $CF_3$, ethyl, propyl, isobutyl, 3-methylbutyl, cyclopropyl, cyclopentyl, cyclopentylmethyl, cyclohexylmethyl or phenyl.

In one embodiment the invention also relates to a compound according to Formula I wherein $R_5$ is H, $R_{15}$ is $CF_3$ and $R_{16}$ is C(1-6)alkyl with all carbon atoms of the alkyl groups optionally substituted with one or more F.

In one embodiment the invention also relates to a compound according to Formula I wherein $R_5$ is H, $R_{15}$ is $CF_3$ and $R_{16}$ is methyl, $CF_3$, ethyl, isobutyl, propyl or 3-methylbutyl.

In one embodiment the invention also relates to a compound according to Formula I wherein $R_5$ is H, $R_{15}$ is $CF_3$ and $R_{16}$ is C(3-6)cycloalkyl.

In one embodiment the invention also relates to a compound according to Formula I wherein $R_5$ is H, $R_{15}$ is $CF_3$ and $R_{16}$ is cyclopentyl.

In one embodiment the invention also relates to a compound according to Formula I wherein $R_5$ is H, $R_{15}$ is $CF_3$ and $R_{16}$ is C(3-6)cycloalkylC(1-3)alkyl.

In one embodiment the invention also relates to a compound according to Formula I wherein $R_5$ is H, $R_{15}$ is $CF_3$ and $R_{16}$ is cyclopentylmethyl or cyclohexylmethyl.

In one embodiment the invention also relates to a compound according to Formula I wherein $R_5$ is H, $R_{15}$ is $CF_3$ and $R_{16}$ is C(6-10)aryl.

In one embodiment the invention also relates to a compound according to Formula I wherein $R_5$ is H, $R_{15}$ is $CF_3$ and $R_{16}$ is phenyl.

In one embodiment the invention also relates to a compound according to Formula I wherein $R_5$ is H, $R_{15}$ is cyclopropyl and $R_{16}$ is cyclopropyl.

In one embodiment the invention also relates to a compound according to Formula I wherein $R_5$ is methyl or isopropyl, $R_{15}$ is $CF_3$ and $R_{16}$ is $CF_3$.

The invention also relates to those compounds wherein all specific definitions for $A_6$ through $A_{10}$, $A_{11}$ through $A_{14}$, $R_1$ through $R_{16}$, and all substituent groups in the various aspects of the inventions defined here above occur in any combination within the definition of the compound of Formula I.

In another aspect the invention relates to compounds of Formula I which have a pIC50 around 5 or higher. In yet another aspect the invention relates to compounds according to Formula I with a pIC50 of more than 6. In yet another aspect the invention relates to compounds according to Formula I with a pIC50 of more than 7.

In yet another aspect the invention resides in the compounds according to Formula I selected as described in examples 1 to 39.

Among the compounds according to the invention, mention may be made especially of the compounds below:

| N° | Structure | IUPAC name |
| --- | --- | --- |
| 1 | 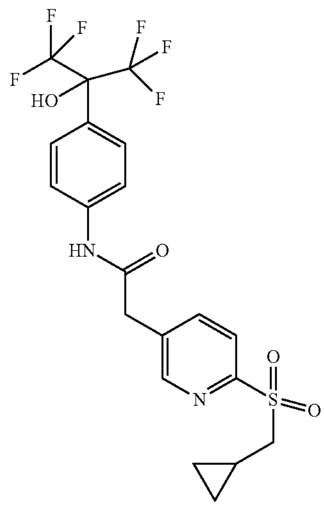 [SMILES: O=C(Cc1ccc(S(=O)(=O)CC2CC2)nc1)Nc1ccc(C(O)(C(F)(F)F)C(F)(F)F)cc1] | 2-[6-(cyclopropylmethylsulfonyl)-3-pyridyl]-N-[4-[2,2,2-trifluoro-1-hydroxy-1-(trifluoromethyl)ethyl]phenyl]acetamide |
| 2 | 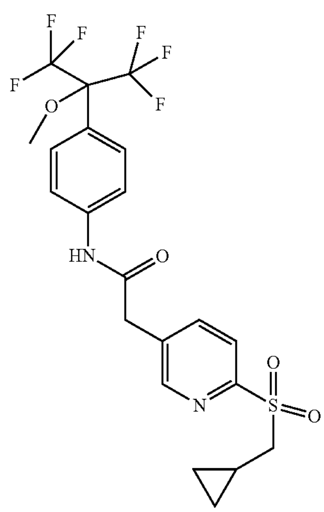 [SMILES: COC(c1ccc(NC(=O)Cc2ccc(S(=O)(=O)CC3CC3)nc2)cc1)(C(F)(F)F)C(F)(F)F] | 2-[6-(cyclopropylmethylsulfonyl)-3-pyridyl]-N-[4-[2,2,2-trifluoro-1-methoxy-1-(trifluoromethyl)ethyl]phenyl]acetamide |
| 3 | 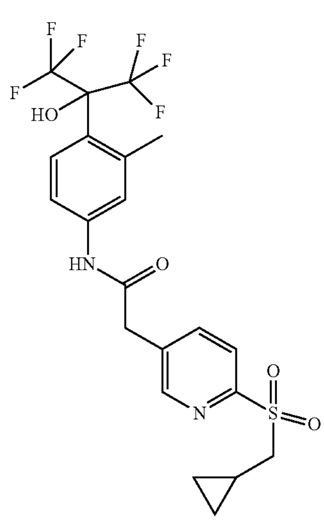 [SMILES: Cc1cc(NC(=O)Cc2ccc(S(=O)(=O)CC3CC3)nc2)ccc1C(O)(C(F)(F)F)C(F)(F)F] | 2-[6-(cyclopropylmethylsulfonyl)-3-pyridyl]-N-[3-methyl-4-[2,2,2-trifluoro-1-hydroxy-1-(trifluoromethyl)ethyl]phenyl]acetamide |

-continued

| N° | Structure | IUPAC name |
|---|---|---|
| 4 | 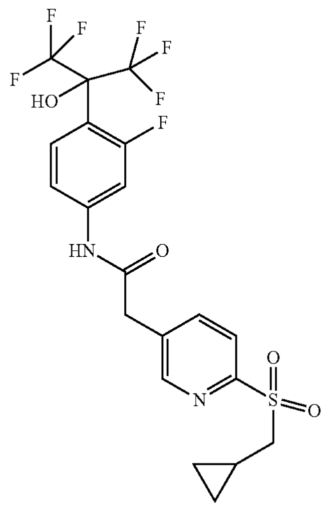 [SMILES: O=C(Cc1ccc(S(=O)(=O)CC2CC2)nc1)Nc1ccc(C(O)(C(F)(F)F)C(F)(F)F)c(F)c1] | 2-[6-(cyclopropylmethylsulfonyl)-3-pyridyl]-N-[3-fluoro-4-[2,2,2-trifluoro-1-hydroxy-1-(trifluoromethyl)ethyl]phenyl]acetamide |
| 5 | 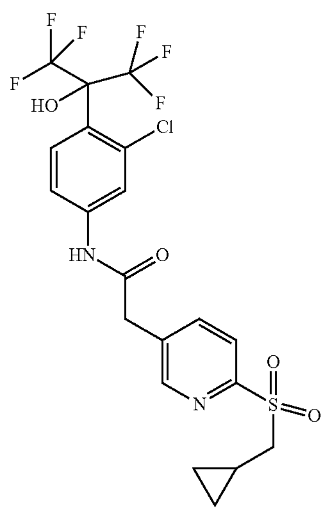 [SMILES: O=C(Cc1ccc(S(=O)(=O)CC2CC2)nc1)Nc1ccc(C(O)(C(F)(F)F)C(F)(F)F)c(Cl)c1] | N-[3-chloro-4-[2,2,2-trifluoro-1-hydroxy-1-(trifluoromethyl)ethyl]phenyl]-2-[6-(cyclopropylmethylsulfonyl)-3-pyridyl]acetamide |
| 6 | 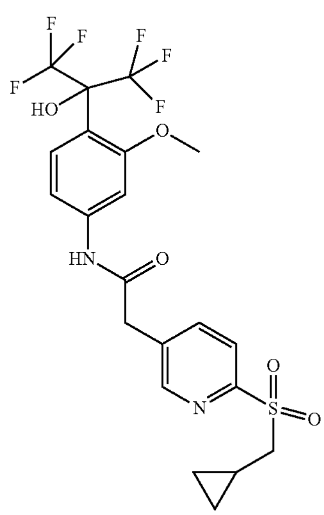 [SMILES: COc1cc(NC(=O)Cc2ccc(S(=O)(=O)CC3CC3)nc2)ccc1C(O)(C(F)(F)F)C(F)(F)F] | 2-[6-(cyclopropylmethylsulfonyl)-3-pyridyl]-N-[3-methoxy-4-[2,2,2-trifluoro-1-hydroxy-1-(trifluoromethyl)ethyl]phenyl]acetamide |

-continued

| N° | Structure | IUPAC name |
|---|---|---|
| 7 | 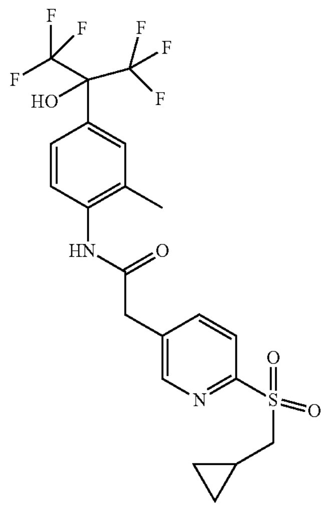 [SMILES: Cc1cc(C(O)(C(F)(F)F)C(F)(F)F)ccc1NC(=O)Cc1ccc(S(=O)(=O)CC2CC2)nc1] | 2-[6-(cyclopropylmethylsulfonyl)-3-pyridyl]-N-[2-methyl-4-[2,2,2-trifluoro-1-hydroxy-1-(trifluoromethyl)ethyl]phenyl]acetamide |
| 8 | 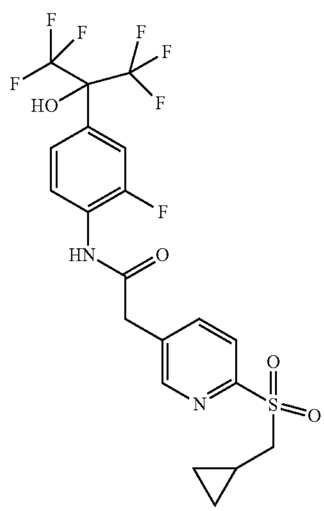 [SMILES: O=C(Cc1ccc(S(=O)(=O)CC2CC2)nc1)Nc1ccc(C(O)(C(F)(F)F)C(F)(F)F)cc1F] | 2-[6-(cyclopropylmethylsulfonyl)-3-pyridyl]-N-[2-fluoro-4-[2,2,2-trifluoro-1-hydroxy-1-(trifluoromethyl)ethyl]phenyl]acetamide |
| 9 | 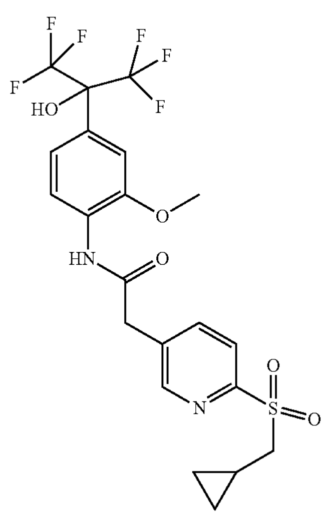 [SMILES: COc1cc(C(O)(C(F)(F)F)C(F)(F)F)ccc1NC(=O)Cc1ccc(S(=O)(=O)CC2CC2)nc1] | 2-[6-(cyclopropylmethylsulfonyl)-3-pyridyl]-N-[2-methoxy-4-[2,2,2-trifluoro-1-hydroxy-1-(trifluoromethyl)ethyl]phenyl]acetamide |

-continued

| N° | Structure | IUPAC name |
|---|---|---|
| 10 | 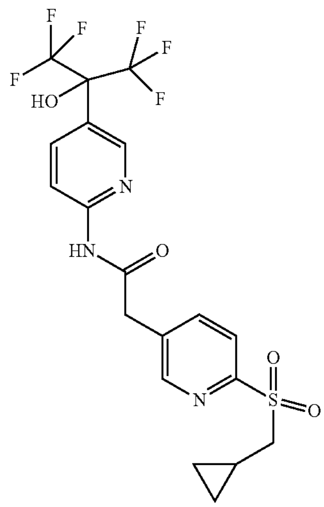 [SMILES: O=C(Cc1ccc(S(=O)(=O)CC2CC2)nc1)Nc1ccc(C(O)(C(F)(F)F)C(F)(F)F)cn1] | 2-[6-(cyclopropylmethylsulfonyl)-3-pyridyl]-N-[5-[2,2,2-trifluoro-1-hydroxy-1-(trifluoromethyl)ethyl]-2-pyridyl]acetamide |
| 11 | 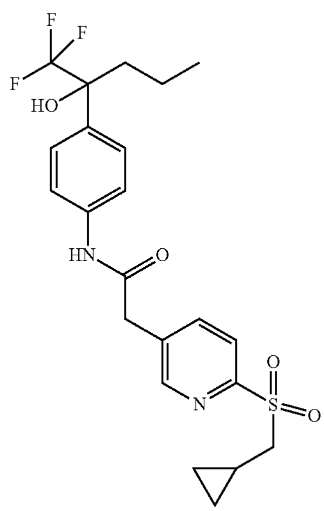 [SMILES: CCCC(O)(c1ccc(NC(=O)Cc2ccc(S(=O)(=O)CC3CC3)nc2)cc1)C(F)(F)F] | 2-[6-(cyclopropylmethylsulfonyl)-3-pyridyl]-N-[4-[1-hydroxy-1-(trifluoromethyl)butyl]phenyl]acetamide |
| 12 | 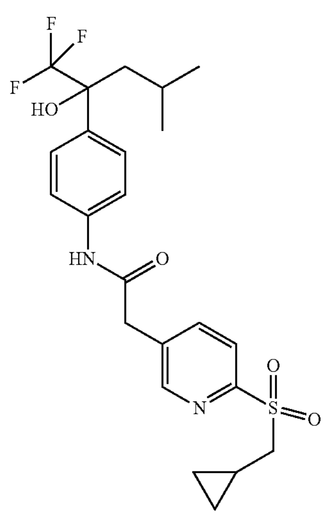 [SMILES: CC(C)CC(O)(c1ccc(NC(=O)Cc2ccc(S(=O)(=O)CC3CC3)nc2)cc1)C(F)(F)F] | 2-[6-(cyclopropylmethylsulfonyl)-3-pyridyl]-N-[4-[1-hydroxy-3-methyl-1-(trifluoromethyl)butyl]phenyl]acetamide |

-continued
| N° | Structure | IUPAC name |
|---|---|---|
| 13 | 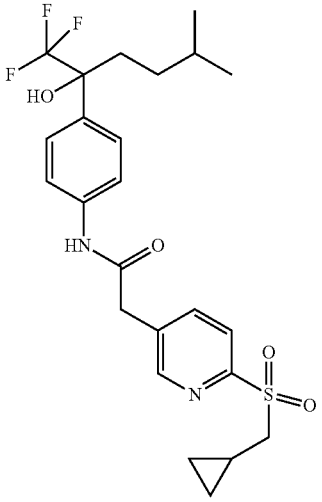 [SMILES: CC(C)CCC(O)(c1ccc(NC(=O)Cc2ccc(S(=O)(=O)CC3CC3)nc2)cc1)C(F)(F)F] | 2-[6-(cyclopropylmethylsulfonyl)-3-pyridyl]-N-[4-[1-hydroxy-4-methyl-1-(trifluoromethyl)pentyl]phenyl]acetamide |
| 14 | 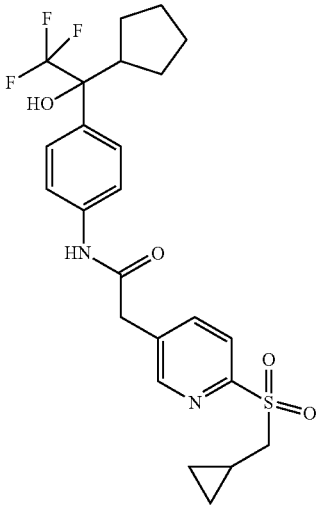 [SMILES: O=C(Cc1ccc(S(=O)(=O)CC2CC2)nc1)Nc1ccc(C(O)(C2CCCC2)C(F)(F)F)cc1] | N-[4-(1-cyclopentyl-2,2,2-trifluoro-1-hydroxy-ethyl)phenyl]-2-[6-(cyclopropylmethylsulfonyl)-3-pyridyl]acetamide |
| 15 | 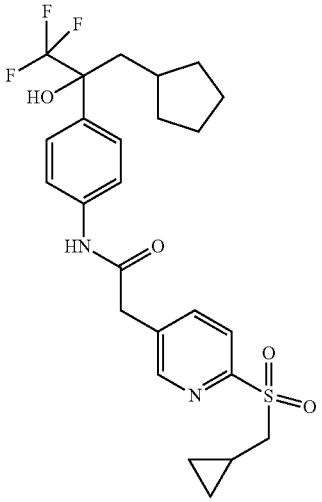 [SMILES: O=C(Cc1ccc(S(=O)(=O)CC2CC2)nc1)Nc1ccc(C(O)(CC2CCCC2)C(F)(F)F)cc1] | N-[4-[1-(cyclopentylmethyl)-2,2,2-trifluoro-1-hydroxy-ethyl]phenyl]-2-[6-(cyclopropylmethylsulfonyl)-3-pyridyl]acetamide |

-continued

| N° | Structure | IUPAC name |
|---|---|---|
| 16 | 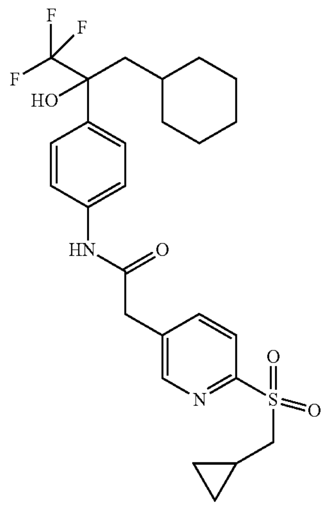 [SMILES: O=C(Cc1ccc(S(=O)(=O)CC2CC2)nc1)Nc1ccc(C(O)(CC2CCCCC2)C(F)(F)F)cc1] | N-[4-[1-(cyclohexylmethyl)-2,2,2-trifluoro-1-hydroxy-ethyl]phenyl]-2-[6-(cyclopropylmethylsulfonyl)-3-pyridyl]acetamide |
| 17 | 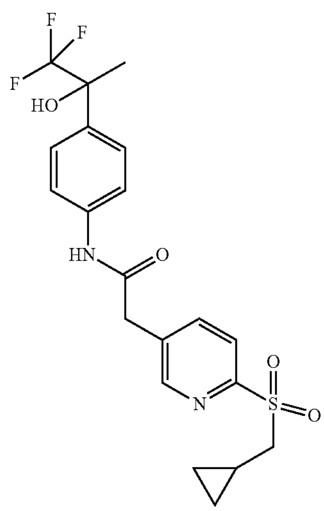 [SMILES: CC(O)(c1ccc(NC(=O)Cc2ccc(S(=O)(=O)CC3CC3)nc2)cc1)C(F)(F)F] | 2-[6-(cyclopropylmethylsulfonyl)-3-pyridyl]-N-[5-(2,2,2-trifluoro-1-hydroxy-1-methyl-ethyl)-2-pyridyl]acetamide |
| 18 | 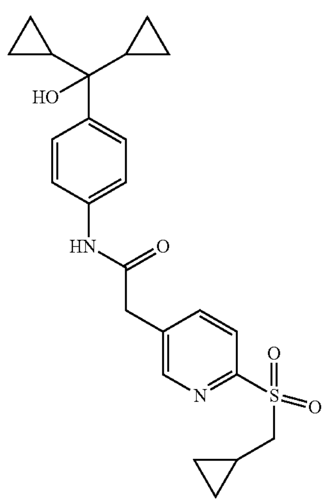 [SMILES: O=C(Cc1ccc(S(=O)(=O)CC2CC2)nc1)Nc1ccc(C(O)(C2CC2)C2CC2)cc1] | 2-[6-(cyclopropylmethylsulfonyl)-3-pyridyl]-N-[4-[dicyclopropyl(hydroxy)methyl]phenyl]acetamide |

-continued

| N° | Structure | IUPAC name |
|---|---|---|
| 19 | 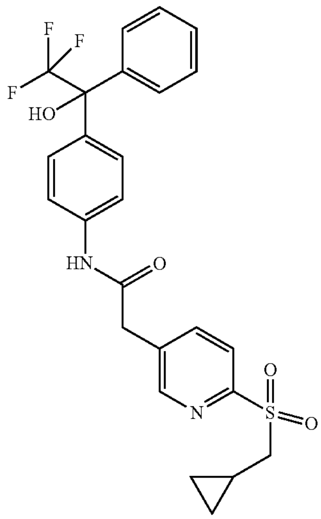 [SMILES: O=C(Cc1ccc(S(=O)(=O)CC2CC2)nc1)Nc1ccc(C(O)(c2ccccc2)C(F)(F)F)cc1] | 2-[6-(cyclopropylmethylsulfonyl)-3-pyridyl]-N-[4-(2,2,2-trifluoro-1-hydroxy-1-phenyl-ethyl)phenyl]acetamide |
| 20<br>(−)-20<br>(+)-20 | 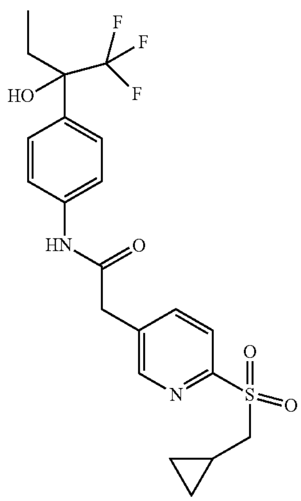 [SMILES: CCC(O)(c1ccc(NC(=O)Cc2ccc(S(=O)(=O)CC3CC3)nc2)cc1)C(F)(F)F] | 20: 2-[6-(cyclopropylmethylsulfonyl)-3-pyridyl]-N-[4-[1-hydroxy-1-(trifluoromethyl)propyl]phenyl]acetamide (racemate)<br>(−)-20: (+)-2-[6-(cyclopropylmethylsulfonyl)-3-pyridyl]-N-[4-[2,2,2-trifluoro-1-hydroxy-1-(trifluoromethyl)ethyl]phenyl]acetamide (levogyreenantiomer)<br>(+)-20: (+)-2-[6-(cyclopropylmethylsulfonyl)-3-pyridyl]-N-[4-[2,2,2-trifluoro-1-hydroxy-1-(trifluoromethyl)ethyl]phenyl]acetamide (dextrogyreenantiomer) |
| 21 | 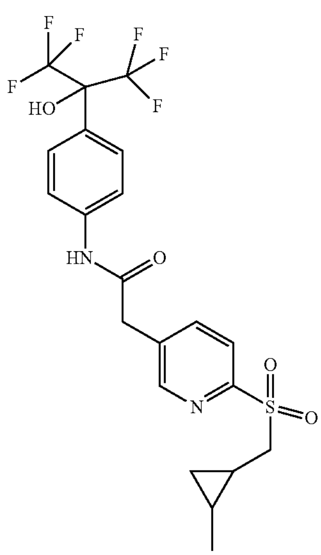 [SMILES: CC1CC1CS(=O)(=O)c1ccc(CC(=O)Nc2ccc(C(O)(C(F)(F)F)C(F)(F)F)cc2)cn1] | 2-[6-[(2-methylcyclopropyl)methylsulfonyl]-3-pyridyl]-N-[4-[2,2,2-trifluoro-1-hydroxy-1-(trifluoromethyl)ethyl]phenyl]acetamide |

-continued

| N° | Structure | IUPAC name |
|---|---|---|
| 22 (+)-22 (−)-22 | | 22: 2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (racemate)<br>(+)-22: (+)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (dextrogyreenantiomer)<br>(−)-22: (−)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (levogyreenantiomer) |
| 23 | 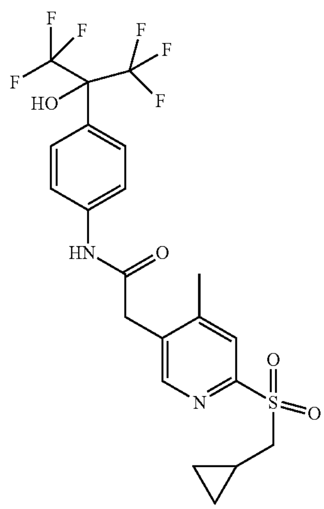 [SMILES: Cc1cc(S(=O)(=O)CC2CC2)ncc1CC(=O)Nc1ccc(C(O)(C(F)(F)F)C(F)(F)F)cc1] | 2-[6-(cyclopropylmethylsulfonyl)-4-methyl-3-pyridyl]-N-[4-[2,2,2-trifluoro-1-hydroxy-1-(trifluoromethyl)ethyl]phenyl]acetamide |
| 24 | 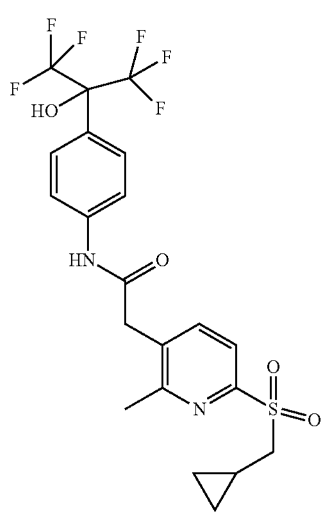 [SMILES: Cc1nc(S(=O)(=O)CC2CC2)ccc1CC(=O)Nc1ccc(C(O)(C(F)(F)F)C(F)(F)F)cc1] | 2-[6-(cyclopropylmethylsulfonyl)-2-methyl-3-pyridyl]-N-[4-[2,2,2-trifluoro-1-hydroxy-1-(trifluoromethyl)ethyl]phenyl]acetamide |

-continued

| N° | Structure | IUPAC name |
|---|---|---|
| 25 | 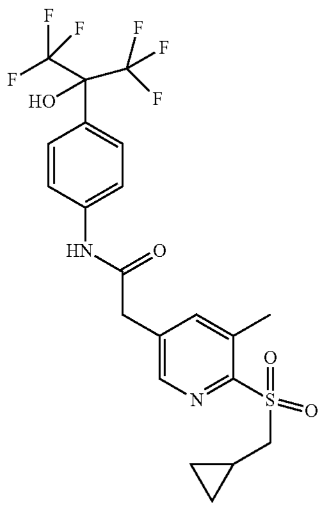 [SMILES: Cc1cc(CC(=O)Nc2ccc(C(O)(C(F)(F)F)C(F)(F)F)cc2)cnc1S(=O)(=O)CC1CC1] | 2-[6-(cyclopropylmethylsulfonyl)-5-methyl-3-pyridyl]-N-[4-[2,2,2-trifluoro-1-hydroxy-1-(trifluoromethyl)ethyl]phenyl]acetamide |
| 26 | 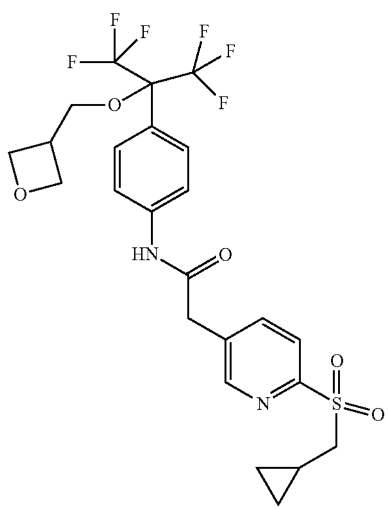 [SMILES: O=C(Cc1ccc(S(=O)(=O)CC2CC2)nc1)Nc1ccc(C(OCC2COC2)(C(F)(F)F)C(F)(F)F)cc1] | 2-[6-(cyclopropylmethylsulfonyl)-3-pyridyl]-N-[4-[2,2,2-trifluoro-1-(oxetan-3-ylmethoxy)-1-(trifluoromethyl)ethyl]phenyl]acetamide |
| 27 | 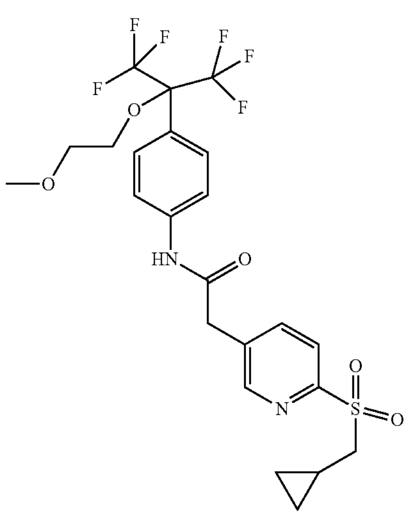 [SMILES: COCCOC(c1ccc(NC(=O)Cc2ccc(S(=O)(=O)CC3CC3)nc2)cc1)(C(F)(F)F)C(F)(F)F] | 2-[6-(cyclopropylmethylsulfonyl)-3-pyridyl]-N-[4-[2,2,2-trifluoro-1-(2-methoxyethoxy)-1-(trifluoromethyl)ethyl]phenyl]acetamide |

| N° | Structure | IUPAC name |
|---|---|---|
| 28 | 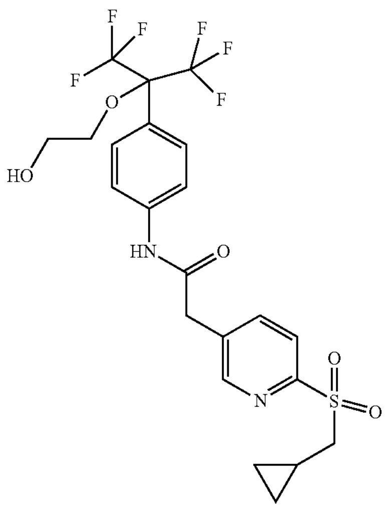 [SMILES: O=C(Cc1ccc(S(=O)(=O)CC2CC2)nc1)Nc1ccc(C(OCCO)(C(F)(F)F)C(F)(F)F)cc1] | 2-[6-(cyclopropylmethylsulfonyl)-3-pyridyl]-N-[4-[2,2,2-trifluoro-1-(2-hydroxyethoxy)-1-(trifluoromethyl)ethyl]phenyl]acetamide |
| 29 | 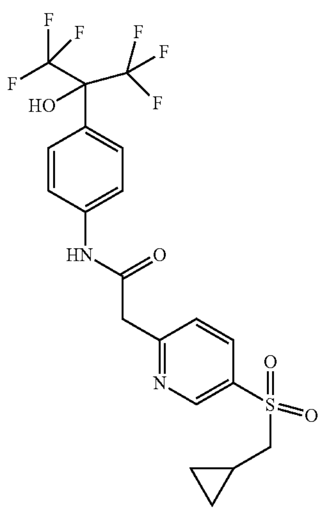 [SMILES: O=C(Cc1ccc(S(=O)(=O)CC2CC2)cn1)Nc1ccc(C(O)(C(F)(F)F)C(F)(F)F)cc1] | 2-[5-(cyclopropylmethylsulfonyl)-2-pyridyl]-N-[4-[2,2,2-trifluoro-1-hydroxy-1-(trifluoromethyl)ethyl]phenyl]acetamide |
| 30 | 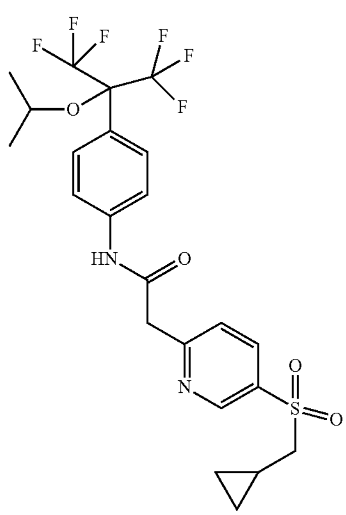 [SMILES: CC(C)OC(c1ccc(NC(=O)Cc2ccc(S(=O)(=O)CC3CC3)cn2)cc1)(C(F)(F)F)C(F)(F)F] | 2-[5-(cyclopropylmethylsulfonyl)-2-pyridyl]-N-[4-[2,2,2-trifluoro-1-isopropoxy-1-(trifluoromethyl)ethyl]phenyl]acetamide |

-continued

| N° | Structure | IUPAC name |
|---|---|---|
| 31 | 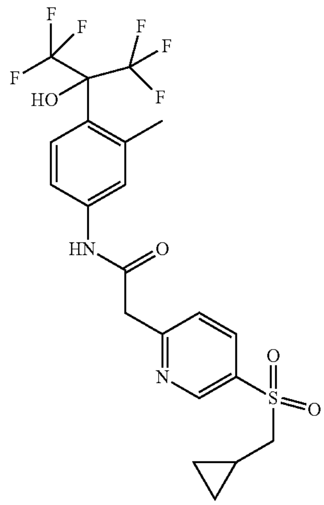 [SMILES: Cc1cc(NC(=O)Cc2ccc(S(=O)(=O)CC3CC3)cn2)ccc1C(O)(C(F)(F)F)C(F)(F)F] | 2-[5-(cyclopropylmethylsulfonyl)-2-pyridyl]-N-[3-methyl-4-[2,2,2-trifluoro-1-hydroxy-1-(trifluoromethyl)ethyl]phenyl]acetamide |
| 32 | 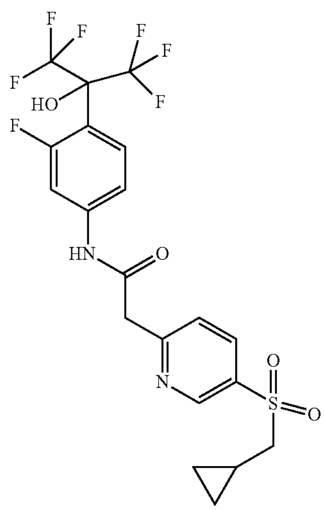 [SMILES: O=C(Cc1ccc(S(=O)(=O)CC2CC2)cn1)Nc1ccc(C(O)(C(F)(F)F)C(F)(F)F)c(F)c1] | 2-[5-(cyclopropylmethylsulfonyl)-2-pyridyl]-N-[3-fluoro-4-[2,2,2-trifluoro-1-hydroxy-1-(trifluoromethyl)ethyl]phenyl]acetamide |
| 33 | 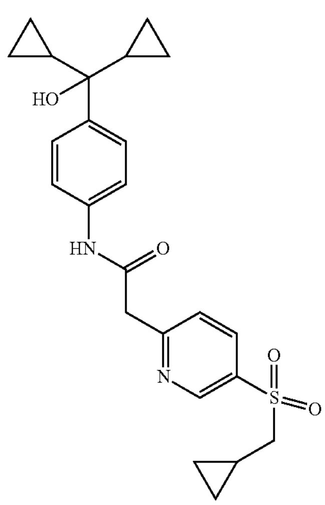 [SMILES: O=C(Cc1ccc(S(=O)(=O)CC2CC2)cn1)Nc1ccc(C(O)(C2CC2)C2CC2)cc1] | 2-[5-(cyclopropylmethylsulfonyl)-2-pyridyl]-N-[4-[dicyclopropyl(hydroxy)methyl]phenyl]acetamide |

-continued

| N° | Structure | IUPAC name |
|---|---|---|
| 34 | 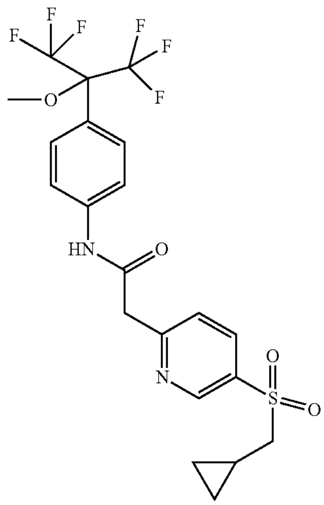 [SMILES: COC(c1ccc(NC(=O)Cc2ccc(S(=O)(=O)CC3CC3)cn2)cc1)(C(F)(F)F)C(F)(F)F] | 2-[5-(cyclopropylmethylsulfonyl)-2-pyridyl]-N-[4-[2,2,2-trifluoro-1-methoxy-1-(trifluoromethyl)ethyl]phenyl]acetamide |
| 35 | 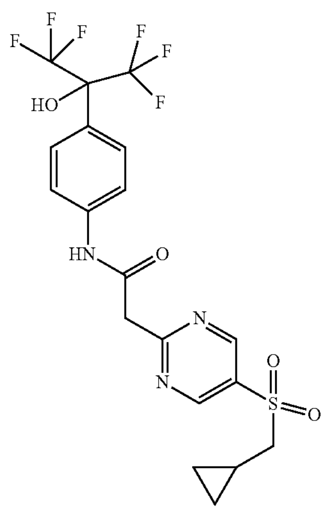 [SMILES: O=C(Cc1ncc(S(=O)(=O)CC2CC2)cn1)Nc1ccc(C(O)(C(F)(F)F)C(F)(F)F)cc1] | 2-[5-(cyclopropylmethylsulfonyl)pyrimidin-2-yl]-N-[4-[2,2,2-trifluoro-1-hydroxy-1-(trifluoromethyl)ethyl]phenyl]acetamide |
| 36 | 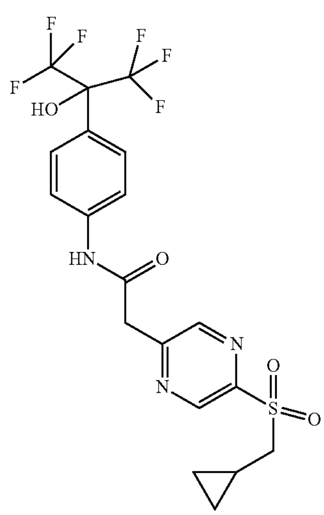 [SMILES: O=C(Cc1cnc(S(=O)(=O)CC2CC2)cn1)Nc1ccc(C(O)(C(F)(F)F)C(F)(F)F)cc1] | 2-[5-(cyclopropylmethylsulfonyl)pyrazin-2-yl]-N-[4-[2,2,2-trifluoro-1-hydroxy-1-(trifluoromethyl)ethyl]phenyl]acetamide |

| N° | Structure | IUPAC name |
|---|---|---|
| 37 | 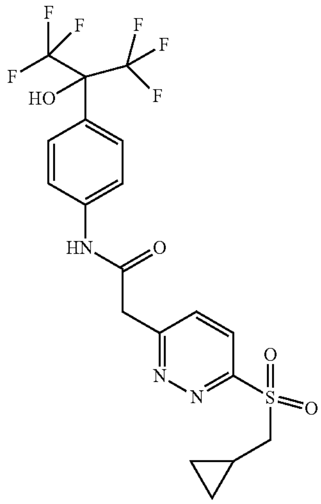 [SMILES: O=C(Cc1ccc(S(=O)(=O)CC2CC2)nn1)Nc1ccc(C(O)(C(F)(F)F)C(F)(F)F)cc1] | 2-[6-(cyclopropylmethylsulfonyl)pyridazin-3-yl]-N-[4-[2,2,2-trifluoro-1-hydroxy-1-(trifluoromethyl)ethyl]phenyl]acetamide |
| 38 | 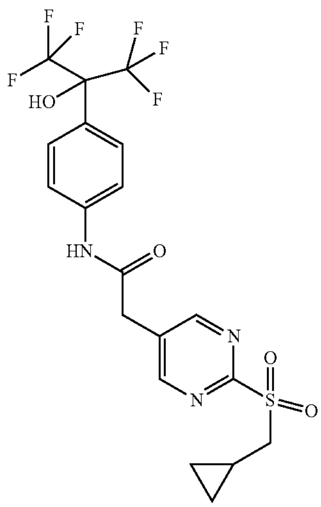 [SMILES: O=C(Cc1cnc(S(=O)(=O)CC2CC2)nc1)Nc1ccc(C(O)(C(F)(F)F)C(F)(F)F)cc1] | 2-[2-(cyclopropylmethylsulfonyl)pyrimidin-5-yl]-N-[4-[2,2,2-trifluoro-1-hydroxy-1-(trifluoromethyl)ethyl]phenyl]acetamide |

The compounds of Formula I can form salts, which are also within the scope of this invention. Reference to a compound of Formula I herein is understood to include reference to salts thereof, unless otherwise indicated.

The compounds of Formula I may contain asymmetric or chiral centers and, therefore, exist in different stereoisomeric forms. It is intended that all stereoisomeric forms of the compounds of Formula I as well as mixtures thereof, including racemic mixtures, form part of the present invention.

Diastereomeric mixtures can be separated into their individual diastereomers on the basis of their physical chemical differences by methods well known to those skilled in the art, such as, for example, chromatography and/or fractional crystallization. Enantiomers can be separated by converting the enantiomeric mixture into a diastereomeric mixture by reaction with an appropriate optically active compound (e.g. chiral auxiliary such as a chiral alcohol or Mosher's acid chloride), separating the diastereomers and converting (e.g. hydrolyzing) the individual diastereomers to the corresponding pure enantiomers. Enantiomers can also be separated by use of chiral HPLC column.

The skilled artisan will recognize that desirable IC50 values are dependent on the compound tested. For example, a compound with an IC50 value less than $10^{-5}$ M is generally considered a candidate for drug selection. Preferably, this value is lower than $10^{-6}$ M. However, a compound which has a higher IC50 value, but is selective for the particular receptor, may even be a better candidate.

The compounds of the invention inhibit RORγ activity. Modulation of RORγ activity can be measured using for example biophysical (natural) ligand displacement studies, biochemical AlphaScreen or FRET assays, cellular GAL4 reporter gene assays, cellular IL-17 promoter reporter assay or functional IL-17 ELISA assays using for example mouse splenocytes or human peripheral blood mononuclear cells (PBMCs) cultured under $T_H17$ polarizing conditions.

In such assays, the interaction of a ligand with RORγ can be determined by measuring, for example, the ligand modulated interaction of cofactor-derived peptides with the RORγ ligand binding domain, or measuring the gene products of ligand modulated RORγ mediated transcription using, for example, luciferase reporter assays or IL-17 ELISA assays.

The present invention also relates to a pharmaceutical composition comprising compounds or pharmaceutically acceptable salts thereof having the general Formula I in admixture with pharmaceutically acceptable excipients and optionally other therapeutic agents. The excipients must be "acceptable" in the sense of being compatible with the other ingredients of the composition and not deleterious to the recipients thereof.

The invention further includes a compound of Formula I in combination with one or more other drug(s).

Compositions include e.g. those suitable for oral, sublingual, subcutaneous, intravenous, intramuscular, topical, nasal, local, or rectal administration, and the like, all in unit dosage forms for administration.

For oral administration, the active ingredient may be presented as discrete units, such as tablets, capsules, powders, granulates, solutions, suspensions, and the like.

For parenteral administration, the pharmaceutical composition of the invention may be presented in unit-dose or multi-dose containers, e.g. injection liquids in predetermined amounts, for example in sealed vials and ampoules, and may also be stored in a freeze dried (lyophilized) condition requiring only the addition of sterile liquid carrier, e.g. water, prior to use.

Mixed with such pharmaceutically acceptable excipients, the active agent may be compressed into solid dosage units, such as pills, tablets, or be processed into capsules or suppositories. By means of pharmaceutically acceptable liquids the active agent can be applied as a fluid composition, e.g. as an injection preparation, in the form of a solution, suspension, emulsion, or as a spray, e.g. a nasal spray.

For making solid dosage units, the use of conventional additives such as fillers, colorants, polymeric binders and the like is contemplated. In general any pharmaceutically acceptable additive which does not interfere with the function of the active compounds can be used. Suitable carriers with which the active agent of the invention can be administered as solid compositions include lactose, starch, cellulose derivatives and the like, or mixtures thereof, used in suitable amounts. For parenteral administration, aqueous suspensions, isotonic saline solutions and sterile injectable solutions may be used, containing pharmaceutically acceptable dispersing agents and/or wetting agents, such as propylene glycol or butylene glycol.

The invention further includes a pharmaceutical composition, as hereinbefore described, in combination with packaging material suitable for said composition, said packaging material including instructions for the use of the composition for the use as hereinbefore described.

The exact dose and regimen of administration of the active ingredient, or a pharmaceutical composition thereof, may vary with the particular compound, the route of administration, and the age and condition of the individual subject to whom the medicament is to be administered.

In general parenteral administration requires lower dosages than other methods of administration which are more dependent upon absorption. However, a dosage for humans preferably contains 0.0001-100 mg per kg body weight. The desired dose may be presented as one dose or as multiple sub-doses administered at appropriate intervals throughout the day.

The compounds according to the invention can be used in therapy.

A further aspect of the invention resides in the use of compounds according to the invention or a pharmaceutically acceptable salt thereof for the treatment of RORγ-mediated diseases or RORγ mediated conditions.

The compounds according to the invention can be used in as medicament.

Another aspect of the invention resides in the use of compounds having the general Formula I or a pharmaceutically acceptable salt thereof for the treatment of autoimmune diseases, in particular those diseases in which Th17 cells and non-Th17 cells, which express Th17 hallmark cytokines play a prominent role. These include, but are not limited to, the treatment of rheumatoid arthritis, psoriasis, inflammatory bowel disease, Crohn's disease and multiple sclerosis.

In another aspect, compounds having the general Formula I or a pharmaceutically acceptable salt thereof can be used for treatment of inflammatory diseases in which Th17 cells and/or non-Th17 cells, which express Th17 hallmark cytokines play a prominent role such as, but not limited to respiratory diseases, osteoarthritis and asthma. Also, compounds or a pharmaceutically acceptable salt thereof having the general Formula I can be used for treatment of infectious diseases in which Th17 cells and/or non-Th17 cells, which express Th17 hallmark cytokines play a prominent role such as, but not limited to mucosal leishmaniasis.

Compounds having the general Formula I or a pharmaceutically acceptable salt thereof can also be used for treatment of other diseases in which Th17 cells and/or non-Th17 cells, which express Th17 hallmark cytokines play a prominent role such as, but not limited to Kawasaki disease and Hashimoto's thyroiditis.

In yet another aspect the invention resides in the use of compounds having the general Formula I for the treatment of multiple sclerosis, inflammatory bowel disease, Crohn's disease, psoriasis, rheumatoid arthritis, asthma, osteoarthritis, Kawasaki disease, Hashimoto's thyroiditis, cancer and mucosal leishmaniasis.

In another aspect, the compounds according to the invention can be used in therapies to treat or prevent multiple sclerosis, inflammatory bowel disease, Crohn's disease, psoriasis, rheumatoid arthritis, asthma, osteoarthritis, Kawasaki disease, Hashimoto's thyroiditis, cancer and mucosal leishmaniasis.

In another aspect the compounds according to the invention can be used to treat or prevent psoriasis.

In yet another aspect the compounds according to the invention can be used to treat inflammatory bowel disease.

The invention is illustrated by the following examples.

EXEMPLIFICATION

As depicted in the Examples below, in certain exemplary embodiments, compounds are prepared according to the following general procedures. It will be appreciated that, although the general methods depict the synthesis of certain compounds of the invention, the following general methods, and other methods known to one skilled in the art, can be applied to all compounds and subclasses and species of each of these compounds, as described herein.

General Methods of Preparation.

The compounds described herein, including compounds of general Formula I, building blocks II, III, IV and V can be readily prepared according to the following reaction schemes and examples, or modifications thereof, using readily available starting materials, reagents and conventional synthesis procedures. Many of the reactions can also be carried out under microwave conditions or using conventional heating or utilizing other technologies such as solid phase reagents/scavengers or flow chemistry. For example, hydrogenation reactions can be performed using a continuous flow chemistry apparatus such as the H-Cube Pro® from ThalesNano Nanotechnology company in Budapest, Hungary. In these reactions, it is also possible to make use of variants which are themselves known to those skilled in the art, but are not mentioned in greater detail.

For example, where specific acids, bases, reagents, coupling agents, solvents, etc. are mentioned, it is understood that other suitable acids, bases, reagents, coupling agents, solvents etc. may be used and are included within the scope of the present invention. Furthermore, other methods for preparing compounds of the invention will be readily apparent to a person of ordinary skill in the art in light of the following reaction schemes and examples. In cases where synthetic intermediates and final products contain potentially reactive functional groups, for example amino, hydroxyl, thiol and carboxylic acid groups that may interfere with the desired reaction, it may be advantageous to employ protected forms of the intermediate. Methods for the selection, introduction and subsequent removal of protecting groups are well known to those skilled in the art. The compounds obtained by using the general reaction sequences may be of insufficient purity. The compounds can be purified by using any of the methods of purification of organic compounds, for example, crystallization or silica gel or alumina column chromatography, using different solvents in suitable ratios. All possible stereoisomers are envisioned within the scope of the invention. In the discussion below variables have the meaning indicated above unless otherwise indicated.

The abbreviations used in these experimental details are listed below and additional ones should be considered known to a person skilled in the art of synthetic chemistry.

Abbreviations used herein are as follow: HATU: 2-(7-Aza-1H-benzotriazole-1-yl)-1,1,3,3-tetramethyluronium hexafluorophosphate; DMF: Dimethylformamide; DiPEA: Diisopropylethylamine; DMAP: 4-(dimethylamino)pyridine; $CH_2Cl_2$, DCM: dichloromethane; DCC: N,N'-Dicyclohexylcarbodiimide; mCPBA: 3-chloroperoxybenzoic acid; TFA: Trifluoroacetic acid; TFAA: Trifluoroacetic anhydride; THF: Tetrahydrofuran; DMSO: Dimethylsulfoxide; PTSA: p-Toluenesulfonic acid; PyBOP: (Benzotriazol-1-yloxy)tripyrrolidinophosphonium hexafluorophosphate; EtOH: Ethanol; DIAD: Diisopropyl azodicarboxylate; TLC: Thin Layer Chromatography; $Pd(dba)_2$: Bis(dibenzylideneacetone)palladium(0); $PPh_3$: Triphenyl phosphine; NMP: N-Methyl-2-pyrrolidinone; EDCl: 1-Ethyl-3-(3-dimethylaminopropyl)carbodiimide hydrochloride; n-BuLi: n-Butyl lithium; TBAF: Tetra-N-butylammonium fluoride; TMS: Trimethylsilyl; NBS: N-bromosuccinimide; AIBN: 2,2'-azobis(2-methylpropionitrile); DCE: dichloroethane; TMSCN: trimethylsilyl cyanide; EtOAc: ethyl acetate; ACN, $CH_3CN$: acetonitrile; RT: room temperature; MeOH: methanol; $Et_3N$, TEA: triethylamine; $NaIO_4$: sodium periodate; $K_2CO_3$: potassium carbonate; $MgSO_4$: magnesium sulfate; $NaBH_3CN$: sodium cyanoborohydride; NaCl: sodium chloride; $NaHCO_3$: sodium bicarbonate; $Na_2CO_3$: sodium carbonate; $Na_2SO_4$: sodium sulfate; $Na_2SO_3$: sodium sulfite; $NH_4Cl$: ammonium chloride; $NH_4OAc$: ammonium acetate; $TMSCF_3$: Trifluoromethyltrimethylsilane; CsF: cesium fluoride; $H_2O$: water; HCl: hydrochloric acid; $CuOSO_2CF_3$: copper(I) trifluoromethanesulfonate; $Cu_2O$: copper(I) oxide; NaOMe: sodium methoxide; NaOH: sodium hydroxide; $NH_4OH$: ammonium hydroxide; $SOCl_2$: thionyl chloride; $Et_2O$: diethyl ether; DBU: 2,3,4,6,7,8,9,10-octahydropyrimido[1,2-a]azepine; $KH_2PO_4$: potassium dihydrogen phosphate; TES: triethylsilyl; $AlMe_3$: trimethylalumane; $Pd(PtBu_3)_2$: bis(tri-tert-butylphosphine)palladium (0); $ZnF_2$: difluorozinc; TES: triethylsilyl.

Chemical names are preferred IUPAC names, generated using Accelrys Draw 4.1.

If a chemical compound is referred to using both a chemical structure and a chemical name, and an ambiguity exists between the structure and the name, the structure predominates.

General Procedures

Scheme 1:

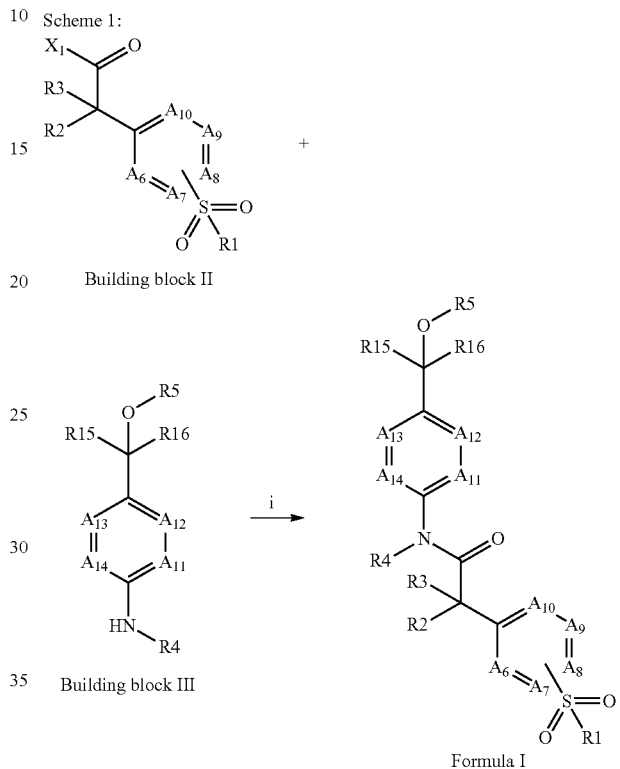

Conditions: i) EDCl, DMAP, DCM.

Scheme 1 demonstrates two alternative routes for the preparation of derivatives of Formula I wherein $R_1$, $R_2$, $R_3$, $R_4$, $R_5$, $R_{15}$, $R_{16}$, $A_6$, $A_7$, $A_8$, $A_9$, $A_{10}$, $A_{11}$, $A_{12}$, $A_{13}$ and $A_{14}$ are as defined for compounds of Formula I.

Compounds of the invention can for example be obtained by an amide coupling reaction between a phenylacetic acid derivative of building block II ($X_1$=OH) and an aniline derivative of building block III, using a coupling reagent such as EDCl, HATU, DCC or PyBOP or the like, in the presence of a suitable base such as DiPEA or DMAP. The reaction is usually performed at room temperature but it could be heated in certain cases to 60° C. under microwave irradiation.

Alternatively, the phenylacetic acid derivative of building block II ($X_1$=OH) can be converted into an acyl chloride derivative of building block II ($X_1$=Cl), using for example $SOCl_2$ or oxalyl chloride. The obtained acyl chloride derivative of building block II ($X_1$=Cl) can be coupled with an aniline derivative of building block III in the presence of a suitable base such as $Et_3N$ or the like.

Alternatively, when $R_5$=$CH_2CH_2OH$, the building block III in which the hydroxyl group in $R_5$ is protected as an acetal, such as a tetrahydropyran-2-yl group, can be condensed with building block II as described above followed by deprotection of the protecting group under acidic conditions to provide the derivatives of Formula I.

Scheme 2:

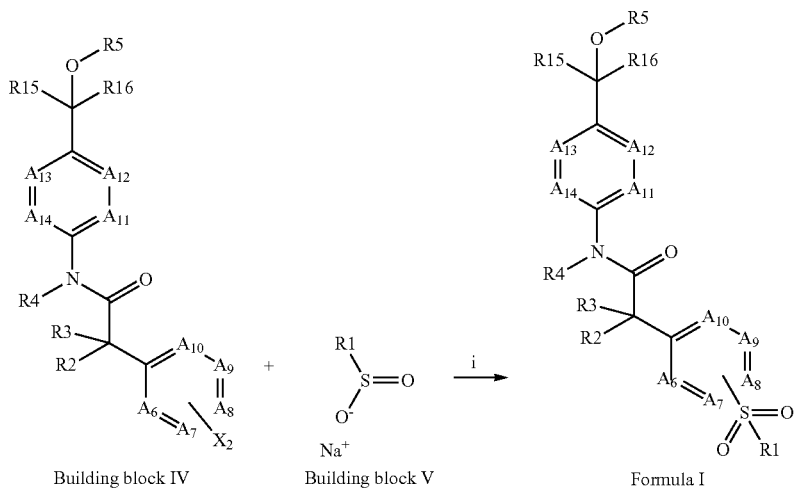

Building block IV    Building block V    Formula I

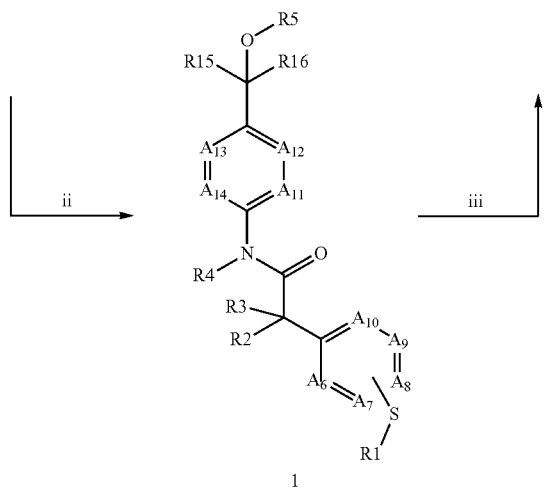

1

Conditions: i) CuOSO$_2$CF$_3$, 1,2-diaminocyclohexane, DMSO, 125° C.; ii) R$_1$SH, NaOMe, MeOH, 85° C., sealed tube; iii) mCPBA, DCM, 0° C.→RT.

Scheme 2 demonstrates two alternative routes for the preparation of derivatives of Formula I wherein R$_1$, R$_2$, R$_3$, R$_4$, R$_5$, R$_{15}$, R$_{16}$, A$_6$, A$_7$, A$_8$, A$_9$, A$_{10}$ A$_{11}$, A$_{12}$, A$_{13}$ and A$_{14}$ are as defined for compounds of Formula I.

Compounds of the invention can be obtained for example by a coupling of an heteroaryl halide derivative (X$_2$=I, Br or Cl) of building block IV and a sulfinic acid salt derivative of building block V such as a sodium sulfinate, using a copper (I) catalyst such as copper(I) trifluoromethanesulfonate benzene complex, copper(I) iodide or the like, in the presence of a suitable ligand such as trans-1,2-diaminocyclohexane, phenanthroline, dimethylimidazolidinone, or the like. The reaction is performed by heating the mixture in a polar solvent such as DMSO, DMF or the like at temperature between 80 and 140° C. using microwave or conventional heating conditions.

Alternatively, certain heteroaryl chloride derivatives (X$_2$=Cl) of building block IV can be treated with a thiol R$_1$SH, wherein R$_1$ has the meaning as previously described, in presence of a base such as sodium methoxide or the like, to give the corresponding thioether derivative 1, which upon oxidation using mCPBA or the like can provide derivatives of the invention having Formula I.

Alternatively, when R$_5$=H, the hydroxyl group of the building block IV can be protected as silyl ether, such as TES or the like. Subsequent deprotection, for example by treatment with a fluoride source such as TBAF, provides the derivatives of Formula I wherein R$_5$=H.

Scheme 3:

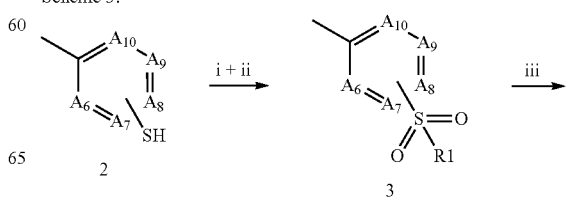

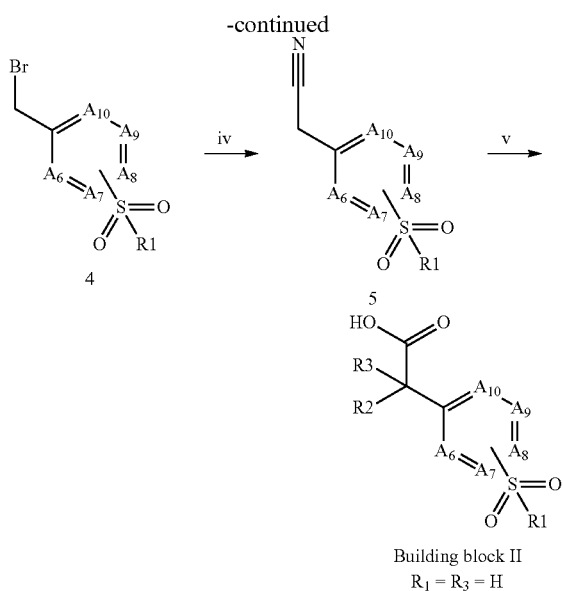

Building block II
$R_1 = R_3 = H$

Conditions ($R_2$, $R_3$=H): i) alkyl halide, $K_2CO_3$, $CH_3CN$; ii) mCPBA, DCM, 0° C.→RT; iii) NBS, AIBN, DCE, 70° C.; iv) TMSCN, TBAF, $CH_3CN$, reflux; v) NaOH, reflux.

Scheme 3 shows a general method for the preparation of building block II, wherein $R_2$=$R_3$=H and $R_1$, $A_6$, $A_7$, $A_8$, $A_9$, $A_{10}$ are as defined for compounds of Formula I.

Thiol derivatives 2 can be alkylated in the presence of a suitable base such as potassium carbonate and oxidized using mCPBA for example to give the corresponding sulfone derivatives 3, which upon radical bromination with NBS in presence of a radical initiator such as AIBN provide bromide derivatives 4. These bromide derivatives can be converted to the corresponding nitrile derivatives 5 by treating them with a cyanide source such as TMSCN or potassium cyanide or the like. If TMSCN is used, it is required to add a fluoride source such as TBAF or the like to generate the cyanide nucleophile in situ. Hydrolysis of the nitrile derivatives 5 can provide the corresponding carboxylic acid derivatives of building block II wherein $R_2$ and $R_3$ are H.

Some of the building blocks II are commercially available, known or prepared according to methods known to those skilled in the art.

Conditions: i) ($R_{15}$, $R_{16}$=$CF_3$, $R_5$=H), hexafluoroacetone hydrate; ii) n-BuLi, ketone; iii) DIAD, PPh$_3$, DMAP, $R_5$OH; iv) deprotection.

Scheme 4 shows two general methods for the preparation of (4-aminophenyl) methanol derivatives of building block III, wherein $R_4$, $R_5$, $R_{15}$, $R_{16}$, $A_{11}$, $A_{12}$, $A_{13}$ and $A_{14}$ are as defined for compounds of Formula I.

If $R_{15}$ and $R_{16}$ are both $CF_3$, then heating the aniline derivatives 6 in 1,1,1,3,3,3-hexafluoroacetone hydrate as the solvent in a sealed tube in a microwave, provides in one step 2-(4-aminophenyl)-1,1,1,3,3,3-hexafluoropropan-2-ol derivatives ($R_5$=H) of building block III.

Alternatively, the 1,1,1,3,3,3-hexafluoropropan-2-ol moiety can be introduced by treating suitable (N-protected) bromoaniline derivatives 7 with n-butyl lithium to form the corresponding lithiated intermediate, which then can be converted by treatment with 1,1,1,3,3,3-hexafluoroacetone gas followed by deprotection of the amine moiety to the desired 2-(4-aminophenyl)-1,1,1,3,3,3-hexafluoropropan-2-ol derivatives ($R_5$=H) of building block III. This method can also be used for the introduction of other tertiary alcohols, by using e.g. dry dicyclopropylmethanone, dry 2,2,2-trifluoro-1-phenyl-ethanone or the like, as the corresponding ketone.

The alcohol derivatives of building block III ($R_5$=H) can, for example, be converted under Mitsunobu conditions, using e.g. DIAD, PPh$_3$, DMAP and a suitable alcohol, to the corresponding ether derivatives of building block III ($R_5$=e.g. alkyl, cycloalkyl).

Scheme 5

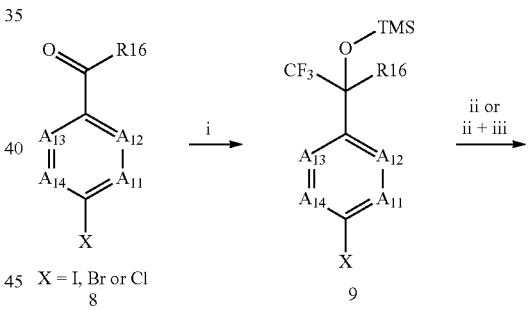

X = I, Br or Cl

Scheme 4:

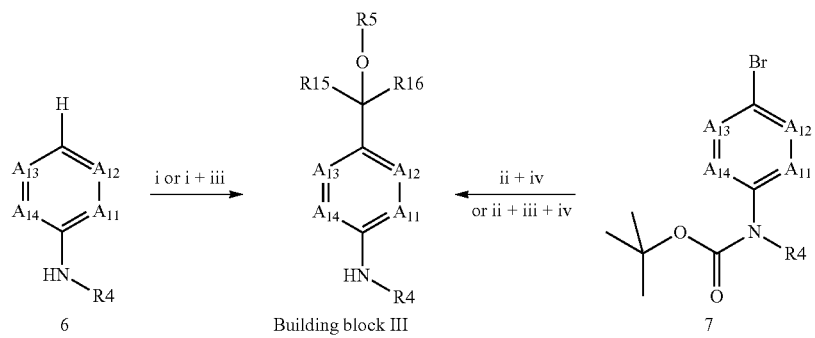

-continued

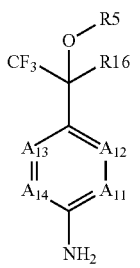

Building block III

Conditions: i) TMSCF$_3$, CsF, Toluene/DCM; ii) NH$_4$OH, Cu$_2$O, NMP, 80° C., microwave; iii) DIAD, PPh$_3$, DMAP, R$_5$OH.

Scheme 5 shows an alternative general method for the preparation of 1-(4-aminophenyl)-2,2,2-trifluoroethanol derivatives of building block III, wherein R$_5$, R$_{16}$, A$_{11}$, A$_{12}$, A$_{13}$ and A$_{14}$ have the meaning as previously described and R$_{15}$ is CF$_3$.

Aryl or heteroaryl halide derivatives 8 (X=I, Br or Cl) can be converted via a cesium fluoride or TBAF catalyzed trifluoromethylation to the corresponding TMS protected 1-(4-aminophenyl)-2,2,2-trifluoroethanol derivatives 9, which can be transformed into the corresponding 1-(4-aminophenyl)-2,2,2-trifluoroethanol derivatives III (R$_5$=H) by a copper catalyzed amination, using Cu$_2$O for example in the presence of ammonia. These alcohol derivatives of building block III can, for instance, be converted under Mitsunobu conditions, using e.g. DIAD, PPh$_3$, DMAP and a suitable alcohol, to the corresponding ether derivatives of building block III (R$_5$=e.g. alkyl, cycloalkyl).

Alternatively, when in the building block III R$_5$ contains a hydroxyl group, this group can be protected as an acetal for example, such as a tetrahydropyran-2-yl group.

Some of the building blocks III are commercially available, known or prepared according to methods known to those skilled in the art.

Scheme 6:

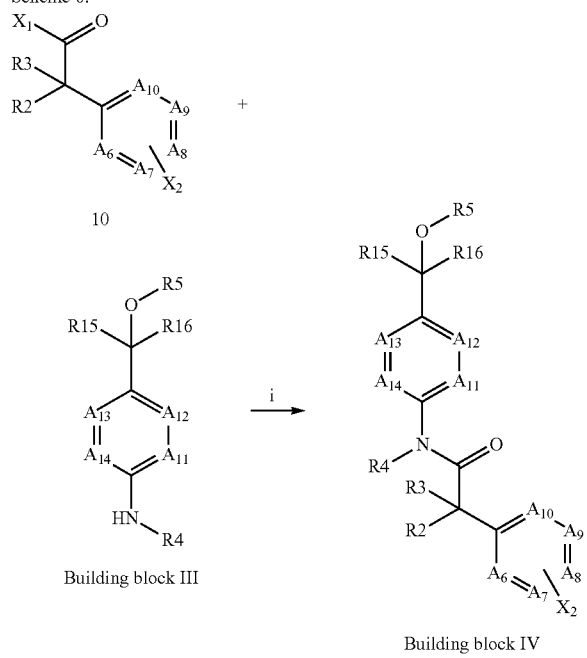

Conditions: i) EDCl, DMAP, DCM.

Scheme 6 shows two general methods for the preparation of derivatives of building block IV, wherein X$_2$ is Cl, Br or I and R$_2$, R$_3$, R$_4$, R$_5$, R$_{15}$, R$_{16}$, A$_6$, A$_7$, A$_8$, A$_9$, A$_{10}$, A$_{11}$, A$_{12}$, A$_{13}$ and A$_{14}$ are as defined for compounds of Formula I.

The building blocks IV can be prepared by an amide coupling reaction between a carboxylic acid derivative 10 (X$_1$=OH) and an aniline derivative of building block III, using a coupling reagent such as EDCl, HATU, DCC, or PyBOP or the like, in the presence of a suitable base such as DiPEA or DMAP.

Alternatively, the carboxylic acid derivative 10 (X$_1$=OH) can be converted into an acyl chloride derivative of 10 (X$_1$=Cl), using for example SOCl$_2$ or oxalyl chloride. The obtained acyl chloride derivative of 10 (X$_1$=Cl) can be coupled with an aniline derivative of building block III are as defined for compounds of Formula I, in the presence of a suitable base such as Et$_3$N or the like.

Alternatively, an ester derivative 10 (X$_1$=OMe) can be condensed with an aniline derivative of building block III in the presence of a suitable Lewis acid such as AlMe$_3$ or the like, to provide the building blocks IV.

Alternatively, when R5=H, the building block III can be protected as silyl ether, such as TES or the like. As a consequence, the resulting building blocks IV can also be protected.

Scheme 7:

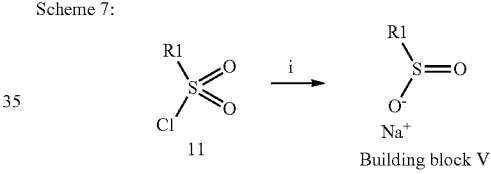

Conditions: i) Na$_2$SO$_3$, NaHCO$_3$, H$_2$O, 50° C.

Scheme 7 shows a general reaction scheme for the preparation of building blocks V wherein R$_1$ has the meaning as previously described.

Sulfonyl chloride derivatives 11 can be converted to sodium sulfinate derivatives of building block V by treatment with sodium sulfite in water in the presence of a suitable base such as sodium bicarbonate.

Some of the building blocks V are commercially available, known or prepared according to methods known to those skilled in the art.

Scheme 8:

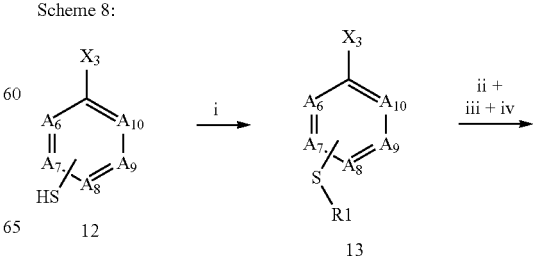

47
-continued

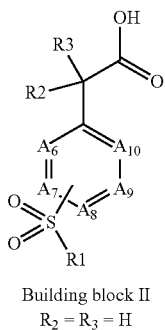

Building block II
R2 = R3 = H

Conditions (R2, R3=H): i) alkyl halide, K2CO3, CH3CN, DMF; ii) (CH3)3CSi(CH3)2OC(OCH3)=CH2, Pd(PtBu3)2, ZnF2, DMF, 100° C., microwave; iii) mCPBA, DCM, 0° C.→RT; iv) NaOH, THF, MeOH.

Thiol derivatives 12 can be alkylated in the presence of a suitable base such as potassium carbonate to give the corresponding thioether derivatives 13 substituted with a halogen X3=I, Br, Cl. These halide derivatives can be converted to the corresponding the carboxylic acid derivatives of building block II wherein R2 and R3 are H by a Heck coupling with tert-butyl-(1-methoxyvinyloxy)-dimethyl-silane catalyzed, for example by Pd(PtBu3)2 and ZnF2, followed by oxydation of the thioether into the sulfone and hydrolysis of the ester.

Some of the building blocks II are commercially available, known or prepared according to methods known to those skilled in the art.

Building Block II-1

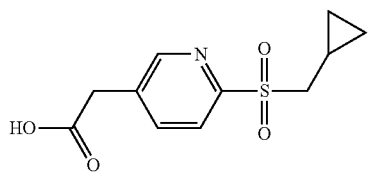

2-[6-(cyclopropylmethylsulfonyl)-3-pyridyl]
acetic acid i) To a suspension of 5-methylpyridine-2-thiol (3 g) and K2CO3 (6.59 g) in ACN (30 mL) was added (bromomethyl)cyclopropane (2.48 mL). After stirring overnight at RT, the reaction mixture was filtered and concentrated under reduced pressure. The residue was taken up in DCM, washed with water, filtered on a water repellent filter cartridge and concentrated under reduced pressure to obtain 4.35 g of the 2-(cyclopropylmethylsulfanyl)-5-methyl-pyridine. MS(ES+) m/z 180.0 [M+H]+.

ii) To a cooled (0° C.) solution of the product obtained in the previous step (3.3 g) in DCM (50 mL) was added portionwise mCPBA (9.94 g). After stirring overnight at RT, DCM was added followed by a saturated aqueous solution of K2CO3. The mixture was stirred for 1 hour, the organic layer was separated, washed twice with water and concentrated under reduced pressure to obtain 3.85 g of the 2-(cyclopropylmethylsulfonyl)-5-methyl-pyridine. MS(ES+) m/z 212.0 [M+H]+.

iii) To a solution of the product obtained in the previous step (610 mg) in DCE (10 mL), was added AIBN (50 mg) followed by NBS (514 mg). The reaction mixture was heated to 70° C. for 7 hours and concentrated under reduced pressure. Water was added to the residue and it was extracted with DCM. The extract was filtered on a water repellent filter cartridge, concentrated under reduced pressure and purified by column chromatography on silica gel using 10% EtOAc in heptane as the eluent to obtain 210 mg of the 5-(bromomethyl)-2-(cyclopropylmethylsulfonyl)pyridine. MS(ES+) m/z 289.9 [M+H]+.

iv) To a solution of the product obtained in the previous step (200 mg) in ACN (10 mL) was added TMSCN (102 mg) and a 1N solution of TBAF in THF (1 mL). The reaction mixture was heated to reflux for 5 minutes, poured into a diluted aqueous solution of ammonia, extracted with EtOAc and concentrated under reduced pressure. The crude product was purified by column chromatography on silica gel using 20% EtOAc in heptane as the eluent to obtain 90 mg of the 2-[6-(cyclopropylmethylsulfonyl)-3-pyridyl]acetonitrile. MS(ES+) m/z 237.0 [M+H]+.

v) To the product obtained in the previous step (90 mg) was added an aqueous 15% w/w NaOH solution (2.5 mL). The reaction mixture was refluxed for 30 minutes. After allowing to cool down to RT, water and an aqueous 2N HCl solution (3 mL) were added and it was extracted three times with ether then twice with EtOAc. The extracts were concentrated under reduced pressure, taken into DCM, filtered on a water repellent filter cartridge and concentrated under reduced pressure to obtain 70 mg of the expected product. MS(ES+) m/z 256.0 [M+H]+.

Building Block II-2

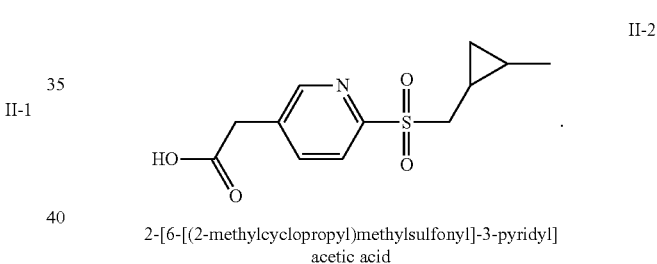

2-[6-[(2-methylcyclopropyl)methylsulfonyl]-3-pyridyl]
acetic acid i) To a suspension of 5-bromopyridine-2-thiol (600 mg) and K2CO3 (881 mg) in ACN (10 mL) were added 1-(bromomethyl)-2-methyl-cyclopropane (545 mg) dropwise and DMF (2 mL). After stirring 2 hours at RT, Et2O (100 mL) was added to the reaction mixture and the organic layer was washed with water (100 mL), with brine (100 mL), dried over Na2SO4, filtered and concentrated under reduced pressure to obtain 790 mg of 5-bromo-2-[(2-methylcyclopropyl)methylsulfanyl]pyridine. The crude product was used in the next step without further purification. MS(ES+) m/z 258.1, 260.1 [M+H]+.

ii) To a solution of the product obtained in the previous step (790 mg) in anhydrous DMF (5 mL) placed in a microwave tube were added tert-butyl-(1-methoxyvinyloxy)-dimethyl-silane (1.19 g) and difluorozinc (160 mg). The reaction mixture was degazed, and bis(tri-tert-butylphosphine)palladium (0) (156 mg) was added. The tube was sealed and heated to 100° C. under microwave irradiation for 45 minutes. The reaction mixture was poured onto EtOAc (50 mL), and the organic layer was washed with water (2×50 mL), brine (50 mL), dried over Na2SO4, filtered and concentrated under reduced pressure. The residue was purified by column chromatography on silica gel, using 0% to 30% EtOAc in cyclohexane as the eluent to obtain 520 mg of methyl 2-[6-[(2-methylcyclopropyl)methylsulfanyl]-3-pyridyl]acetate. MS(ES+) m/z 252.2 [M+H]+.

iii) To a cooled (0° C.) solution of the product obtained in the previous step (520 mg) in DCM (10 mL) was added portionwise mCPBA (1.02 g). After stirring overnight at RT, a saturated aqueous solution of NaHCO3 (50 mL) was added and the mixture was stirred for 15 minutes, followed by addition of DCM (80 mL) and a saturated aqueous solution of NaHCO3 (50 mL). The organic layer was separated, dried over Na2SO4, filtered and concentrated under reduced pressure. The residue was purified by column chromatography on silica gel, using 0 to 60% EtOAc in cyclohexane as the eluent to obtain 430 mg of methyl 2-[6-[(2-methylcyclopropyl)methylsulfonyl]-3-pyridyl]acetate. MS(ES+) m/z 284.0 [M+H]+.

iv) A 1N aqueous solution of NaOH (1.5 mL) was added to a solution of the product obtained in the previous step (430 mg) in THF (8 mL) and MeOH (2 mL) and the mixture was stirred overnight at RT. Water (20 mL) and DCM (50 mL) were added, and the organic layer was discarded. The aqueous layer was acidified using HCl 1N, and extracted with DCM (3×50 mL). The combined organic layers were dried over Na2SO4, filtered and concentrated under reduced pressure to obtain 350 mg of the expected product. MS(ES+) m/z 270.1 [M+H]+.

Following a procedure analogous to that described for compound 11-2, the following compounds were prepared.

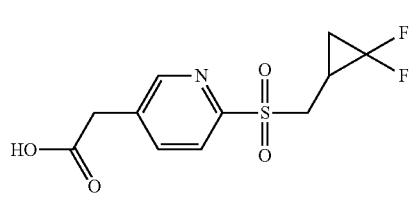

II-3

2-[6-[(2,2-difluorocyclopropyl)methylsulfonyl]-3-pyridyl]acetic acid. MS(ES+) m/z 292.1 [M+H]+.

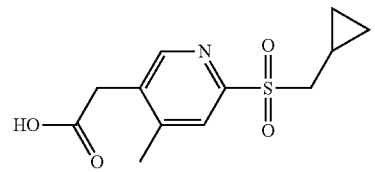

II-4

2-[6-(cyclopropylmethylsulfonyl)-4-methyl-3-pyridyl]acetic acid. MS(ES+) m/z 270.1 [M+H]+.

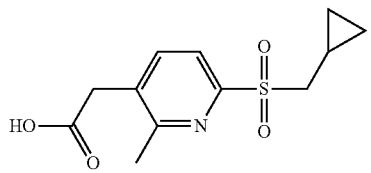

II-5

2-[6-(cyclopropylmethylsulfonyl)-2-methyl-3-pyridyl]acetic acid. MS(ES+) m/z 270.1 [M+H]+.

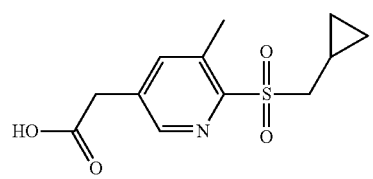

II-6

2-[6-(cyclopropylmethylsulfonyl)-5-methyl-3-pyridyl]acetic acid. MS(ES+) m/z 270.1 [M+H]+.

Building blocks III-1-III-8

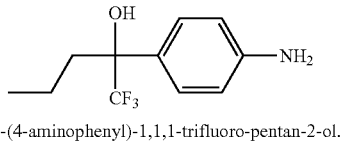

III-1

2-(4-aminophenyl)-1,1,1-trifluoro-pentan-2-ol.

i) To a solution of 1-(4-bromophenyl)butan-1-one (1.0 g) in a mixture of toluene and DCM (2 mL, 9:10) was added TMSCF3 (0.65 mL). To this suspension CsF (67 mg) was added. After a few minutes an exothermic reaction started and the reaction mixture was stirred for another 30 minutes until completion. The reaction mixture was quenched by the addition of water. The organic layer was washed with water, brine, dried over MgSO4 and concentrated under reduced pressure. The residue was purified by column chromatography on silica gel using 0% to 40% EtOAc in heptane as the eluent to obtain 1.5 g of [1-(4-bromophenyl)-1-(trifluoromethyl)butoxy]-trimethyl-silane.

ii) To a solution of the product obtained in the previous step (1.5 g) in NMP (4 mL) were added Cu2O (30 mg) and an aqueous NH4OH solution (4 mL). The reaction mixture was stirred for 15 hours at 80° C. in a microwave. The blue reaction mixture was poured into water and the product was extracted with EtOAc. The organic extract was washed with water, brine, dried over MgSO4 and concentrated under reduced pressure to obtain the expected compound. The crude product was used without further purification. MS(ES+) m/z 234.1 [M+H]+.

Following a procedure analogous to that described for Example III-1, the following compounds were prepared.

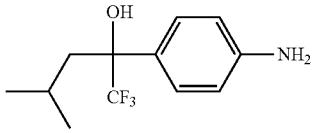

III-2

2-(4-aminophenyl)-1,1,1-trifluoro-4-methyl-pentan-2-ol. MS(ES+) m/z 262.3 [M+H]+.

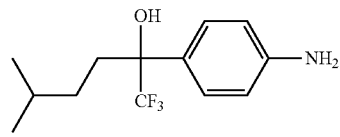

III-3

2-(4-aminophenyl)-1,1,1-trifluoro-5-methyl-hexan-2-ol. MS(ES+) m/z 248.1 [M+H]+.

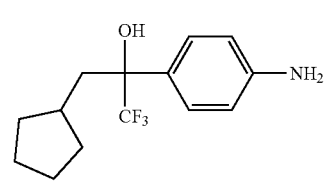

III-4

2-(4-aminophenyl)-3-cyclopentyl-1,1,1-trifluoro-propan-2-ol. MS(ES+) m/z 274.1 [M+H]+.

-continued

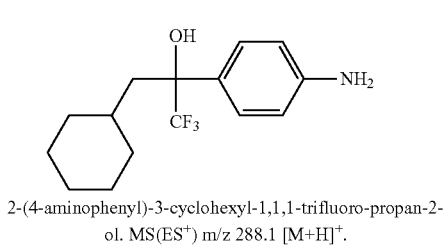

2-(4-aminophenyl)-3-cyclohexyl-1,1,1-trifluoro-propan-2-ol. MS(ES+) m/z 288.1 [M+H]+.

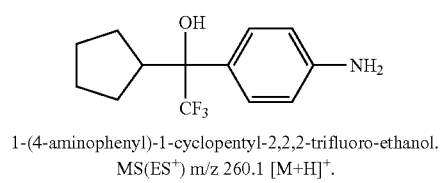

1-(4-aminophenyl)-1-cyclopentyl-2,2,2-trifluoro-ethanol. MS(ES+) m/z 260.1 [M+H]+.

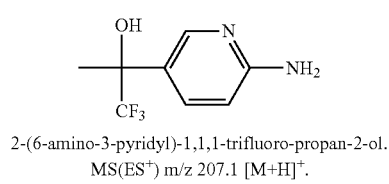

2-(6-amino-3-pyridyl)-1,1,1-trifluoro-propan-2-ol. MS(ES+) m/z 207.1 [M+H]+.

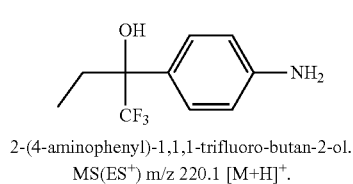

2-(4-aminophenyl)-1,1,1-trifluoro-butan-2-ol. MS(ES+) m/z 220.1 [M+H]+.

Building Blocks III-9–III-11

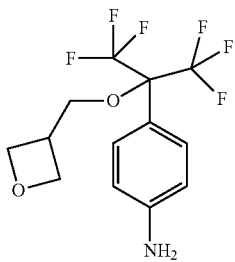

4-[2,2,2-trifluoro-1-(oxetan-3-ylmethoxy)-1-(trifluoromethyl)ethyl]aniline

To a solution of 2-(4-aminophenyl)-1,1,1,3,3,3-hexafluoropropan-2-ol (500 mg) and oxetan-3-ylmethanol (177 mg) in THF (5 mL) cooled at −10° C. were successively added PPh₃ (1.01 g) and dropwise DIAD (0.760 mL). The reaction mixture was stirred at RT overnight and concentrated under reduced pressure. The residue was purified by column chromatography on silica gel, using 20% to 40% EtOAc in heptane as the eluent to obtain 389 mg of 4-[2,2,2-trifluoro-1-(oxetan-3-ylmethoxy)-1-(trifluoromethyl)ethyl]aniline. MS(ES+) m/z 330.1 [M+H]+.

Following a procedure analogous to that described for compound III-9, the following compounds were prepared.

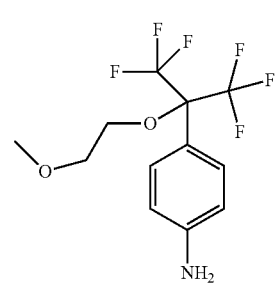

4-[2,2,2-trifluoro-1-(2-methoxyethoxy)-1-(trifluoromethyl)ethyl]aniline. MS(ES+) m/z 318.1 [M+H]+.

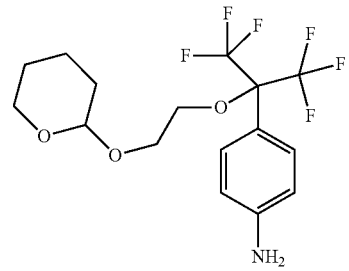

4-[2,2,2-trifluoro-1-(2-tetrahydropyran-2-yloxyethoxy)-1-(trifluoromethyl)ethyl]aniline. MS(ES+) m/z 388.2 [M+H]+; 410.1 [M+Na]+.

Building Block III-12

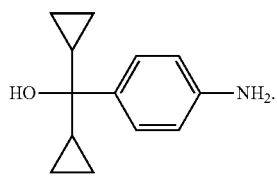

(4-aminophenyl)-dicyclopropyl-methanol i) To a solution of tert-butyl N-(4-bromophenyl)carbamate (20.1 g) in dry THF (400 mL) at −78° C. under nitrogen atmosphere was added dropwise n-BuLi (59.1 mL, 2.5 M in hexanes). After stirring at −78° C. for 2 hours, dicyclopropylmethanone (9.28 mL) was added dropwise and the reaction mixture was allowed to slowly warm up to RT overnight. The reaction mixture was quenched by addition of a saturated aqueous NH₄Cl solution (200 mL). The layers were separated and the aqueous layer was extracted with EtOAc (2×200 mL). The combined organic extracts were washed with brine, dried over Na₂SO₄ and concentrated under reduced pressure. The residue was purified by column chromatography on silica gel, using DCM as the eluent to obtain 16.5 g of tert-butyl N-[4-[dicyclopropyl(hydroxy)methyl]phenyl]carbamate.

ii) To a solution of the product obtained in the previous step (16.5 g) in dry THF (200 mL) under a nitrogen atmosphere was added at RT a 1 M solution of TBAF in THF (82 mL). The reaction mixture was stirred at 80° C. overnight. The next day, a 1 M solution of TBAF in THF (103 mL) was added and the reaction mixture was stirred at 80° C. overnight. The next day, the reaction mixture was concentrated to half of the volume, a 1 M solution of TBAF in THF (120 mL) was added and the reaction mixture was stirred at 80° C. overnight. After being cooled to RT, the reaction mixture was quenched with a mixture of water (900 mL) and a saturated aqueous Na$_2$CO$_3$ solution (100 mL) and was extracted with EtOAc (3×300 mL). The combined organic layers were washed with brine, dried over Na$_2$SO$_4$ and concentrated under reduced pressure. The residue was purified by column chromatography on silica gel, using 5% to 40% EtOAc in n-heptane as the eluent to obtain 7.8 g of the expected compound.

MS(ES$^+$) m/z 186.1 [(M-18)+H]$^+$.

$^1$H NMR (500 MHz, CDCl$_3$): δ 7.40-7.34 (m, 2H), 6.67-6.62 (m, 2H), 3.62 (s, 2H), 1.39 (s, 1H), 1.26-1.11 (m, 2H), 0.57-0.45 (m, 4H), 0.39-0.32 (m, 4H).

Building Block III-13

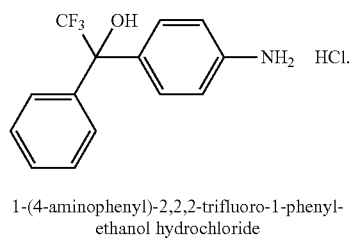

III-13

1-(4-aminophenyl)-2,2,2-trifluoro-1-phenyl-ethanol hydrochloride i) To a solution of tert-butyl N-(4-bromophenyl)carbamate (1.0 g) in dry THF (20 mL) at −78° C. under nitrogen atmosphere was added dropwise n-BuLi (3.7 mL, 2.5 M in hexanes). After stirring for 2 hours at −78° C., 2,2,2-trifluoro-1-phenyl-ethanone (0.7 g) was added dropwise and the reaction mixture was allowed to slowly warm up to RT overnight. The reaction mixture was quenched by addition of a saturated aqueous NH$_4$Cl solution (200 mL). The layers were separated and the aqueous layer was extracted with EtOAc (2×200 mL). The combined organic extracts were washed with brine, dried over Na$_2$SO$_4$ and concentrated under reduced pressure. The residue was purified by column chromatography on silica gel to obtain 384 mg of tert-butyl N-[4-(2,2,2-trifluoro-1-hydroxy-1-phenyl-ethyl)phenyl]carbamate.

ii) To a solution of the product obtained in the previous step (379 mg) in DCM (10 mL) under a nitrogen atmosphere was added hydrochloric acid (1.29 mL, 4N in dioxane). The reaction mixture was stirred overnight at RT. The next day, hydrochloric acid (1.29 mL, 4N in dioxane) was added and the reaction mixture was stirred at RT for 2 days. The reaction mixture was then concentrated under reduced pressure, and the solid was suspended in DCM and again concentrated under reduced pressure to obtain 293 mg of the expected compound.

MS(ES$^+$) m/z 268.0 [M+H]$^+$.

Building Blocks IV-1-IV-9

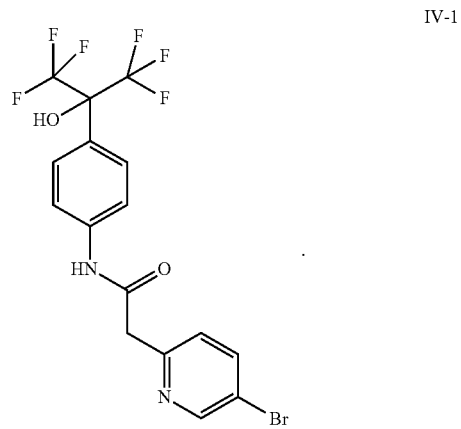

IV-1

2-(5-bromo-2-pyridyl)-N-[4-[2,2,2-trifluoro-1-hydroxy-1-(trifluoromethyl)ethyl]phenyl]acetamide i) To a solution of 2-(5-bromopyridin-2-yl)acetic acid (500 mg) in DCM (4 mL) were added 2-(4-aminophenyl)-1,1,1,3,3,3-hexafluoro-propan-2-ol (625 mg), EDCl (476 mg) and DMAP (57 mg). The reaction mixture was stirred at RT for 1 hour, poured into water, filtered on a water repellent filter cartridge and concentrated under reduced pressure. The residue was purified by column chromatography on silica gel, using 10% EtOAc in heptane as the eluent, followed by trituration with ether/pentane to obtain 820 mg of the expected compound. MS(ES$^+$) m/z 456.9 [M+H]$^+$.

Following a procedure analogous to that described for compound IV-1, using the appropriate building blocks III or any commercially available ones, the following compounds were prepared.

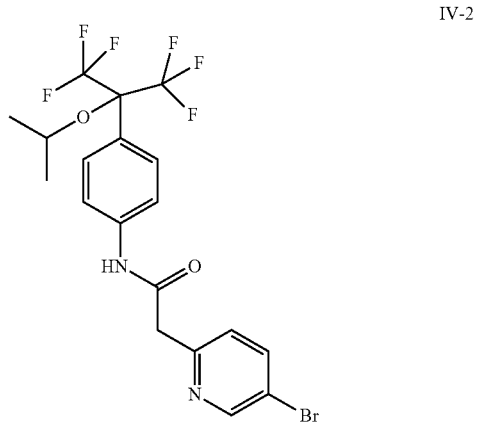

IV-2

2-(5-bromo-2-pyridyl)-N-[4-[2,2,2-trifluoro-1-isopropoxy-1-(trifluoromethyl)ethyl]phenyl]acetamide.
MS(ES$^+$) m/z 499.0 [M+H]$^+$.

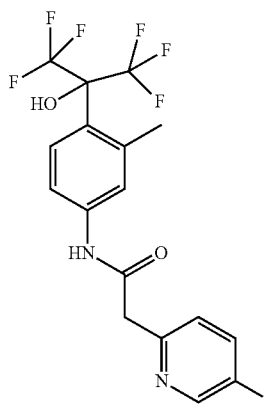

IV-3

2-(5-bromo-2-pyridyl)-N-[3-methyl-4-[2,2,2-trifluoro-1-hydroxy-1-(trifluoromethyl)ethyl]phenyl]acetamide.
MS(ES$^+$) m/z 471.0 [M+H]$^+$.

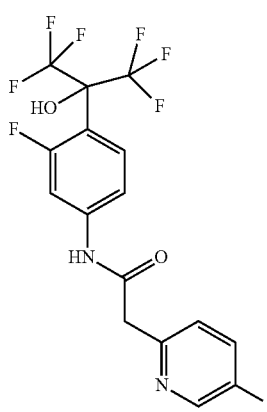

IV-4

2-(5-bromo-2-pyridyl)-N-[3-fluoro-4-[2,2,2-trifluoro-1-hydroxy-1-(trifluoromethyl)ethyl]phenyl]acetamide.
MS(ES$^+$) m/z 475.2 [M+H]$^+$.

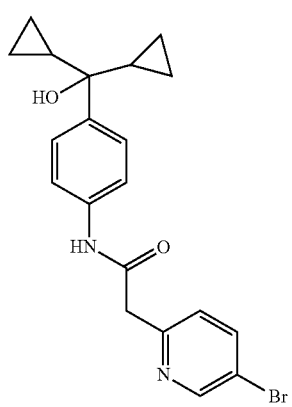

IV-5

2-(5-bromo-2-pyridyl)-N-[4-[dicyclopropyl(hydroxy)methyl]phenyl]acetamide.
MS(ES$^+$) m/z 401.1 [M+H]$^+$.

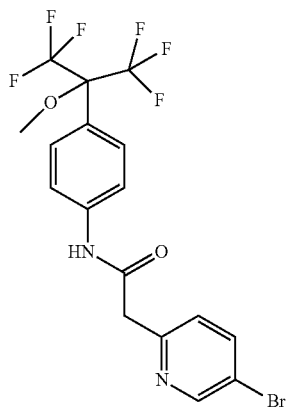

IV-6

2-(5-bromo-2-pyridyl)-N-[4-[2,2,2-trifluoro-1-methoxy-1-(trifluoromethyl)ethyl]phenyl]acetamide.
MS(ES$^+$) m/z 471.2 [M+H]$^+$.

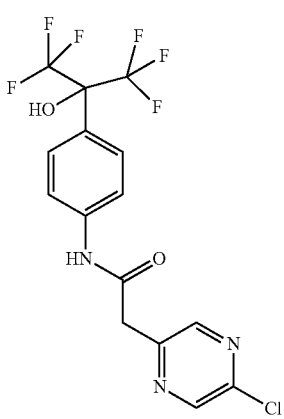

IV-7

2-(5-chloropyrazin-2-yl)-N-[4-[2,2,2-trifluoro-1-hydroxy-1-(trifluoromethyl)ethyl]phenyl]acetamide.
MS(ES$^+$) m/z 414.0 [M+H]$^+$.

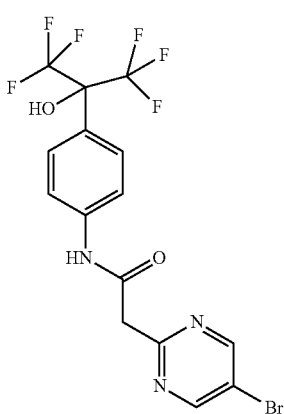

IV-8

2-(5-bromopyrimidin-2-yl)-N-[4-[2,2,2-trifluoro-1-hydroxy-1-(trifluoromethyl)ethyl]phenyl]acetamide.
MS(ES$^+$) m/z 458.0, 460.0 [M+H]$^+$.

-continued

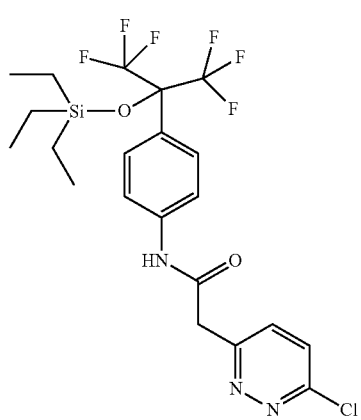

2-(6-chloropyridazin-3-yl)-N-[4-[2,2,2-trifluoro-1-triethylsilyloxy-1-(trifluoromethyl)ethyl]phenyl]acetamide.

i) To a solution of 2-(4-aminophenyl)-1,1,1,3,3,3-hexafluoro-propan-2-ol (2 g) in DMF (50 mL) were added chloro(triethyl)silane (1.74 g), and DBU (1.84 g) dropwise. After stirring at RT for 2 hours, the reaction mixture was quenched by addition of water and Et$_2$O. The layers were separated and the aqueous layer was extracted twice with Et$_2$O. The combined organic extracts were concentrated under reduced pressure, and the residue was taken up in DCM, washed with water, filtered on a water repellent filter cartridge and concentrated under reduced pressure. The residue was purified by column chromatography on silica gel, using 5% EtOAc in heptane as the eluent to obtain 1.9 g of 4-[2,2,2-trifluoro-1-triethylsilyloxy-1-(trifluoromethyl)ethyl]aniline. MS(ES$^+$) m/z 374.1 [M+H]$^+$.

ii) Trimethylalumane (2.49 mL, 2M in toluene) was added to a solution of the product obtained in the previous step (1.86 g) in toluene (50 mL) and the reaction mixture was stirred at RT for 30 minutes before adding ethyl 2-(6-chloropyridazin-3-yl)acetate (500 mg). The reaction mixture was refluxed for 2 hours, then cooled to RT and stirred overnight. It was quenched by pouring onto a mixture of water and EtOAc, and adding a saturated aqueous solution of KH$_2$PO$_4$. The organic layer was recovered, washed with water, concentrated under reduced pressure, and the residue was taken up in DCM, washed with water, filtered on a water repellent filter cartridge and concentrated under reduced pressure. The residue was purified by column chromatography on silica gel, using 10% EtOAc in heptane as the eluent to obtain 375 mg of the expected product. MS(ES$^+$) m/z 528.1 [M+H]$^+$.
Building Block V-1

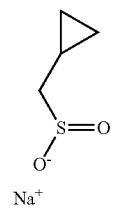

Sodium cyclopropylmethanesulfinate i) A solution of Na$_2$SO$_3$ (414 mg) in water (1.3 mL) was stirred for 10 minutes at RT. To the resulting mixture was added NaHCO$_3$ (547 mg). After stirring for 1 hour at 50° C., cyclopropylmethanesulfonyl chloride (430 mg) was added dropwise. The reaction mixture was stirred at 50° C. for 4 hours. Water was evaporated by flushing argon. The residue was dried under high vacuum. The residue was taken up into MeOH (1.3 mL), filtered and concentrated under reduced pressure to obtain 380 mg of the expected compound. MS(ES$^+$) m/z 120.9 [M+H]$^+$.

Examples 1-27

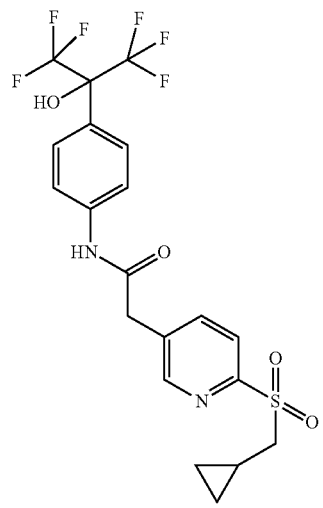

2-[6-(cyclopropylmethylsulfonyl)-3-pyridyl]-N-[4-[2,2,2-trifluoro-1-hydroxy-1-(trifluoromethyl)ethyl]phenyl]acetamide i) To a solution of acid II-1 (55 mg) in DCM (4 mL) were added 2-(4-aminophenyl)-1,1,1,3,3,3-hexafluoro-propan-2-ol (59 mg), EDCl (44 mg) and DMAP (5 mg). The reaction mixture was stirred at RT for 1 hour. DCM and water were added and the mixture was filtered on a water repellent filter cartridge and concentrated under reduced pressure. The residue was purified by column chromatography on silica gel, using 10% to 50% EtOAc in heptane as the eluent, followed by trituration with ether/pentane to obtain 45 mg of the expected compound. MS(ES$^+$) m/z 497.0 [M+H]$^+$.

1H NMR (400 MHz, DMSO-d6) δ ppm 10.50 (s, 1H) 8.73 (d, J=1.25 Hz, 1H) 8.59 (br s, 1H) 8.04-8.11 (m, 2H) 7.68-7.73 (m, 2H) 7.61 (d, J=8.78 Hz, 2H) 3.92 (s, 2H) 3.35-3.43 (m, 2H) 0.82-0.92 (m, 1H) 0.40-0.46 (m, 2H) 0.12-0.17 (m, 2H).

Following a procedure analogous to that described for Example 1, using the appropriate building blocks II and III or any commercially available or known ones, the following compounds were prepared.

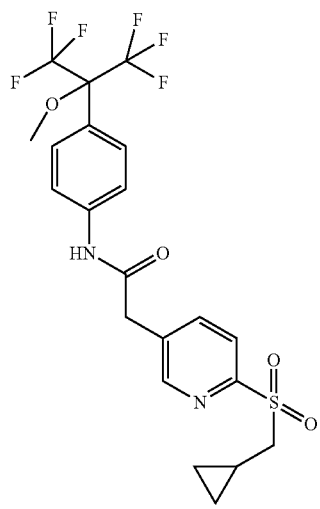

MS(ES⁺) m/z 511.0 [M + H]⁺
2-[6-(cyclopropylmethylsulfonyl)-3-pyridyl]-N-[4-[2,2,2-trifluoro-1-methoxy-1-(trifluoromethyl)ethyl]phenyl]acetamide 1H NMR (400 MHz, DMSO-d6) δ ppm 10.58 (s, 1H) 8.73 (d, J=1.25 Hz, 1H) 8.02-8.13 (m, 2H) 7.79 (d, J=8.04 Hz, 2H) 7.51 (d, J=8.78 Hz, 2H) 3.93 (s, 2H) 3.34-3.45 (m, 5H) 0.82-0.96 (m, 1H) 0.39-0.47 (m, 2H) 0.10-0.19 (m, 2H).

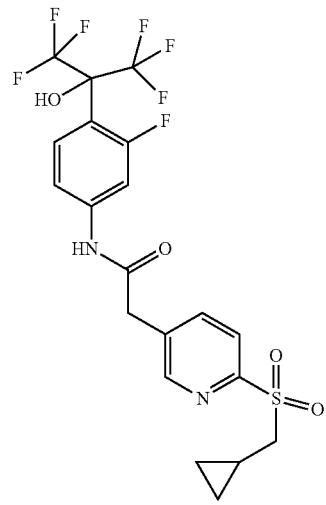

2-[6-(cyclopropylmethylsulfonyl)-3-pyridyl]-N-[3-fluoro-4-[2,2,2-trifluoro-1-hydroxy-1-(trifluoromethyl)ethyl]phenyl]acetamide.
MS(ES⁺) m/z 515.1 [M+H]⁺.

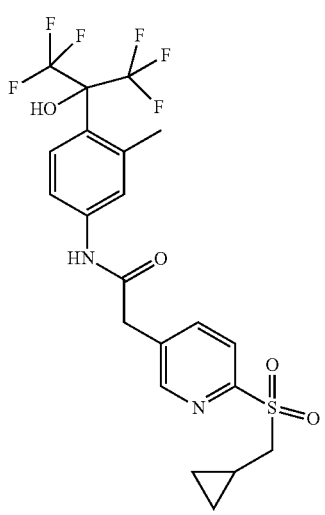

2-[6-(cyclopropylmethylsulfonyl)-3-pyridyl]-N-[3-methyl-4-[2,2,2-trifluoro-1-hydroxy-1-(trifluoromethyl)ethyl]phenyl]acetamide.
MS(ES⁺) m/z 511.2 [M+H]⁺.

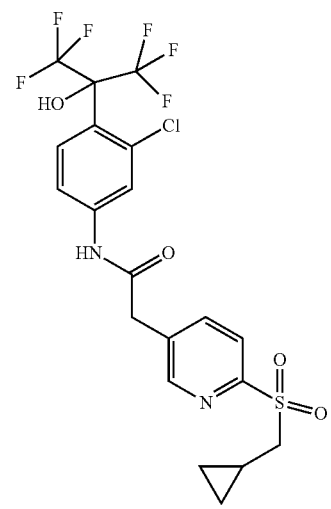

N-[3-chloro-4-[2,2,2-trifluoro-1-hydroxy-1-(trifluoromethyl)ethyl]phenyl]-2-[6-(cyclopropylmethylsulfonyl)-3-pyridyl]acetamide.
MS(ES⁺) m/z 531.1 [M+H]⁺.

5

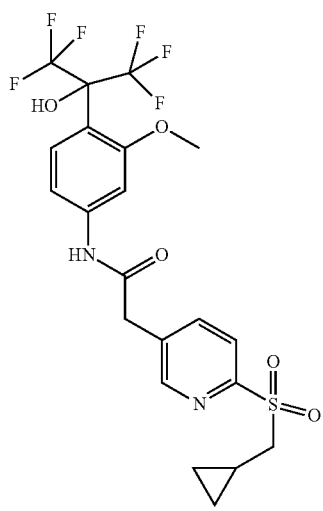

2-[6-(cyclopropylmethylsulfonyl)-3-pyridyl]-N-[3-methoxy-4-[2,2,2-trifluoro-1-hydroxy-1-(trifluoromethyl)ethyl]phenyl]acetamide. MS(ES⁺) m/z 527.1 [M+H]⁺.

6

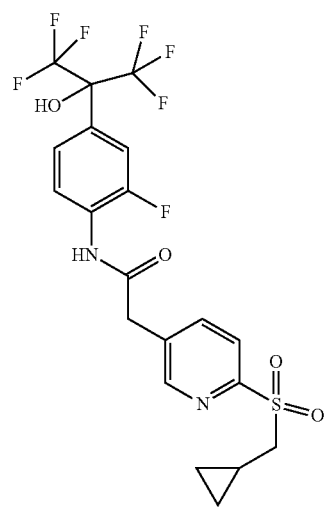

2-[6-(cyclopropylmethylsulfonyl)-3-pyridyl]-N-[2-fluoro-4-[2,2,2-trifluoro-1-hydroxy-1-(trifluoromethyl)ethyl]phenyl]acetamide. MS(ES⁺) m/z 515.1 [M+H]⁺.

7

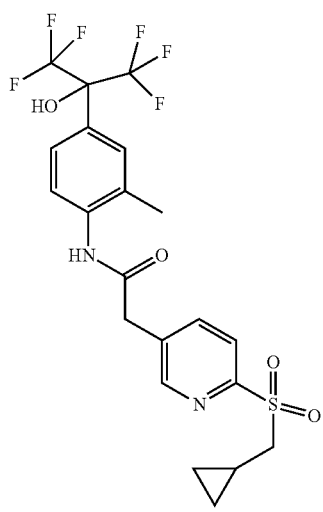

2-[6-(cyclopropylmethylsulfonyl)-3-pyridyl]-N-[2-methyl-4-[2,2,2-trifluoro-1-hydroxy-1-(trifluoromethyl)ethyl]phenyl]acetamide. MS(ES⁺) m/z 511.2 [M+H]⁺.

8

9

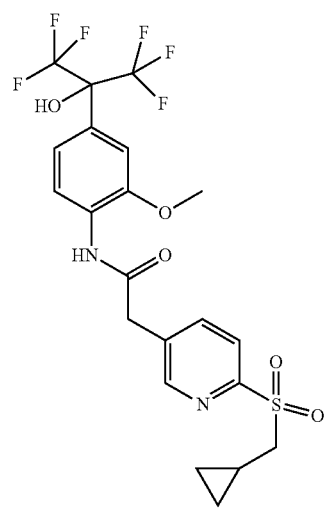

2-[6-(cyclopropylmethylsulfonyl)-3-pyridyl]-N-[2-methoxy-4-[2,2,2-trifluoro-1-hydroxy-1-(trifluoromethyl)ethyl]phenyl]acetamide. MS(ES⁺) m/z 527.1 [M+H]⁺.

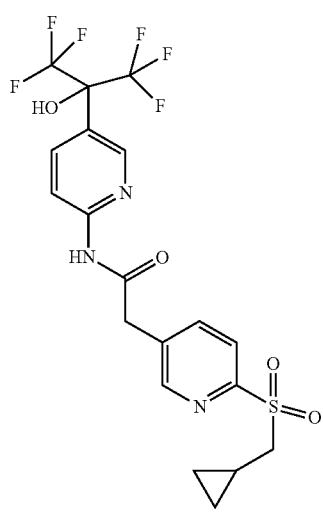

2-[6-(cyclopropylmethylsulfonyl)-3-pyridyl]-N-[5-[2,2,2-trifluoro-1-hydroxy-1-(trifluoromethyl)ethyl]-2-pyridyl]acetamide.
MS(ES$^+$) m/z 498.1 [M+H]$^+$.

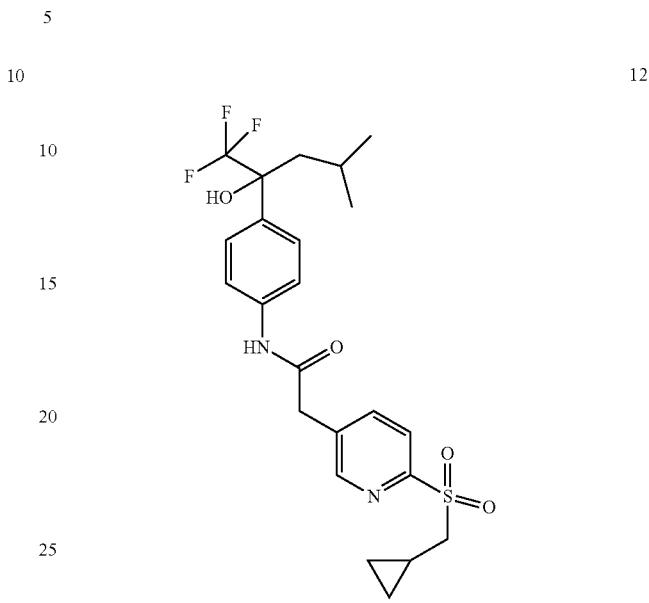

2-[6-(cyclopropylmethylsulfonyl)-3-pyridyl]-N-[4-[1-hydroxy-3-methyl-1-(trifluoromethyl)butyl]phenyl]acetamide.
MS(ES$^+$) m/z 485.2 [M+H]$^+$.

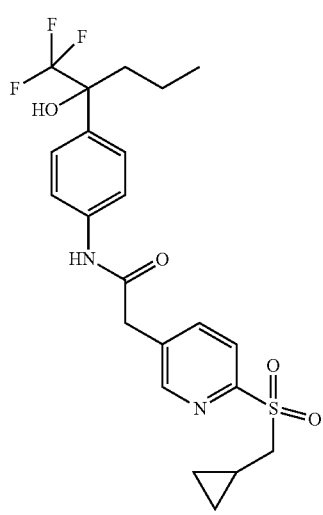

2-[6-(cyclopropylmethylsulfonyl)-3-pyridyl]-N-[4-[1-hydroxy-1-(trifluoromethyl)butyl]phenyl]acetamide.
MS(ES$^+$) m/z 471.2 [M+H]$^+$.

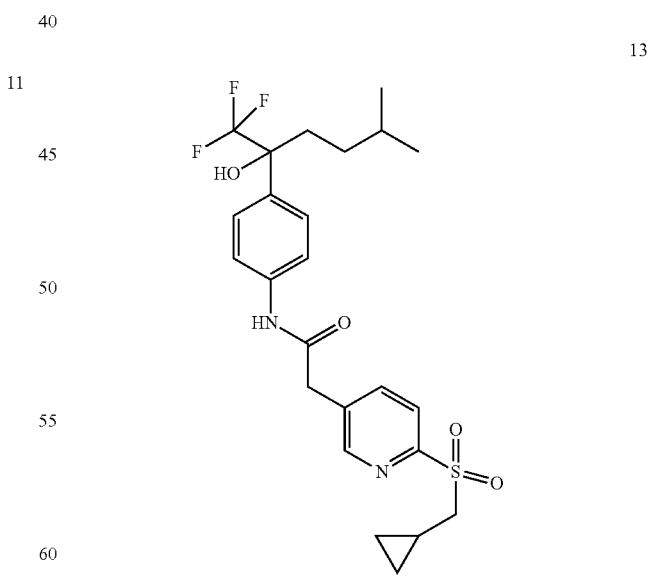

2-[6-(cyclopropylmethylsulfonyl)-3-pyridyl]-N-[4-[1-hydroxy-4-methyl-1-(trifluoromethyl)pentyl]phenyl]acetamide.
MS(ES$^+$) m/z 499.2 [M+H]$^+$.

14

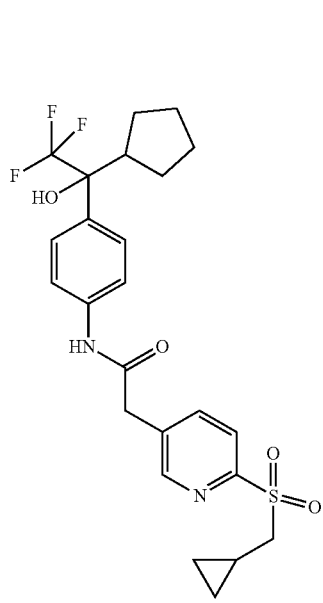

N-[4-(1-cyclopentyl-2,2,2-trifluoro-1-hydroxy-ethyl)phenyl]-2-[6-(cyclopropylmethylsulfonyl)-3-pyridyl]acetamide.
MS(ES$^+$) m/z 497.2 [M+H]$^+$.

16

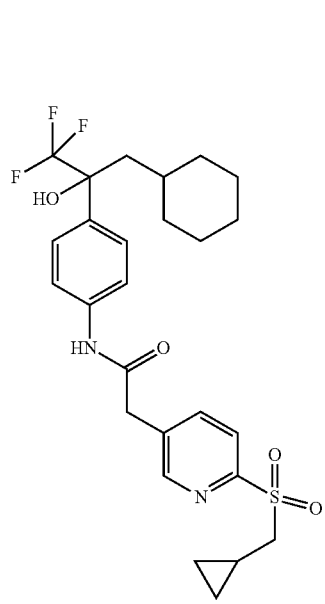

N-[4-[1-cyclohexylmethyl)-2,2,2-trifluoro-1-hydroxy-ethyl]phenyl]-2-[6-(cyclopropylmethylsulfonyl)-3-pyridyl]acetamide.
MS(ES$^+$) m/z 525.3 [M+H]$^+$.

15

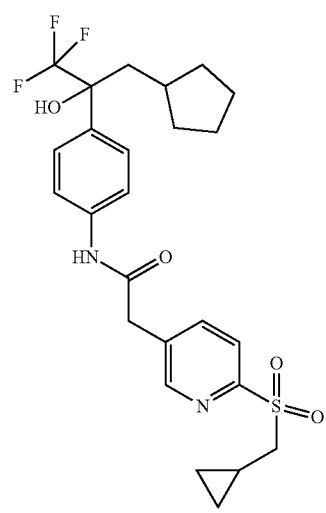

N-[4-[1-cyclopentylmethyl)-2,2,2-trifluoro-1-hydroxy-ethyl]phenyl]-2-[6-(cyclopropylmethylsulfonyl)-3-pyridyl]acetamide.
MS(ES$^+$) m/z 511.2 [M+H]$^+$.

17

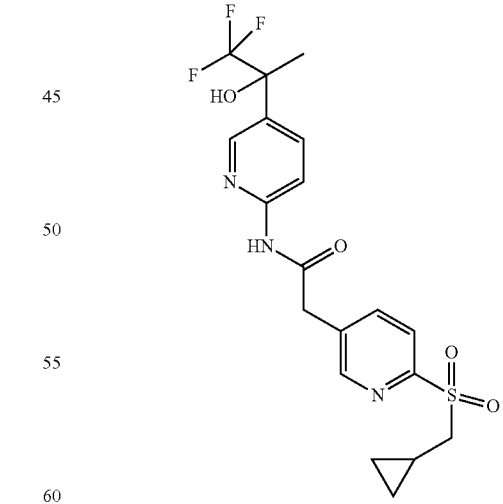

2-[6-(cyclopropylmethylsulfonyl)-3-pyridyl]-N-[5-(2,2,2-trifluoro-1-hydroxy-1-methyl-ethyl)-2-pyridyl]acetamide.
MS(ES$^+$) m/z 444.1 [M+H]$^+$.

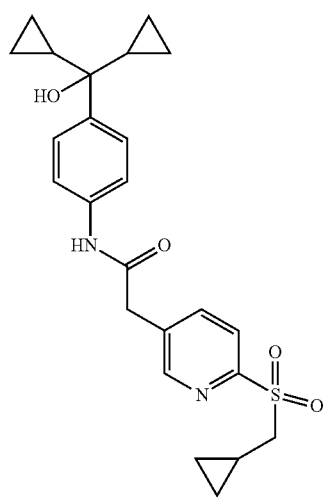

2-[6-(cyclopropylmethylsulfonyl)-3-pyridyl]-N-[4-[dicyclopropyl(hydroxy)methyl]phenyl]acetamide.
MS(ES$^+$) m/z 423.2 [M+H]$^+$.

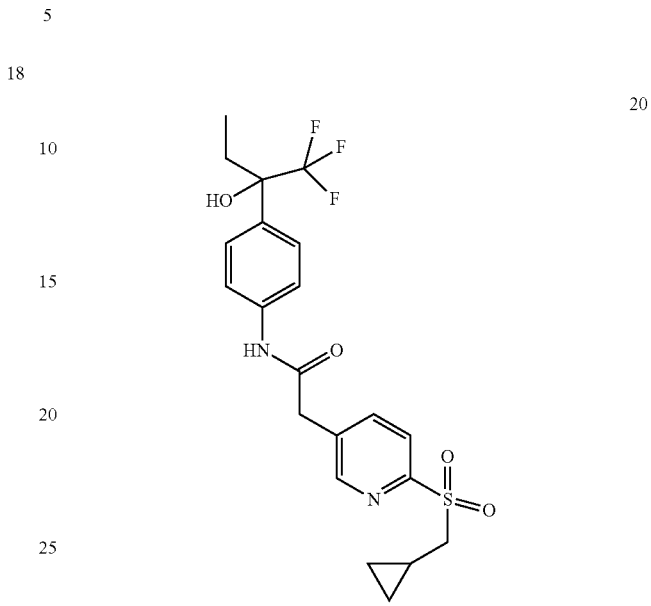

2-[6-(cyclopropylmethylsulfonyl)-3-pyridyl]-N-[4-[1-hydroxy-1-(trifluoromethyl)propyl]phenyl]acetamide.
MS(ES$^+$) m/z 457.1 [M+H]$^+$.

1H NMR (400 MHz, DMSO-d6) δ ppm 10.34 (s, 1H) 8.72 (dd, J=2.2, 0.8 Hz, 1H) 8.10 (dd, J=8.1, 2.2 Hz, 1H) 8.05 (dd, J=8.1, 0.8 Hz, 1H) 7.60 (d, J=9.0 Hz, 2H) 7.46 (br d, J=9.0 Hz, 2H) 6.28 (br s, 1H) 3.89 (s, 2H) 3.39 (d, J=7.3 Hz, 2H) 2.13 (m, 1H) 1.97 (m, 1H) 0.88 (m, 1H) 0.67 (t, J=7.4 Hz, 3H) 0.42 (m, 2H) 0.14 (m, 2H).

The 2 enantiomers of example 20 were separated by chiral chromatography using a column Chiralpak AD 20 μm, 76.5×350 mm and a mobile phase, EtOH:MeOH:TEA 60:40:0.1, 300 mL/min, with UV detection at 254 nm.

Starting from 225 mg of racemate, after concentration, 104 mg of (−)-2-[6-(cyclopropylmethylsulfonyl)-3-pyridyl]-N-[4-[1-hydroxy-1-(trifluoromethyl)propyl]phenyl]acetamide (first isomer to be eluted) and 116 mg of (+)-2-[6-(cyclopropylmethylsulfonyl)-3-pyridyl]-N-[4-[1-hydroxy-1-(trifluoromethyl)propyl]phenyl]acetamide were obtained.

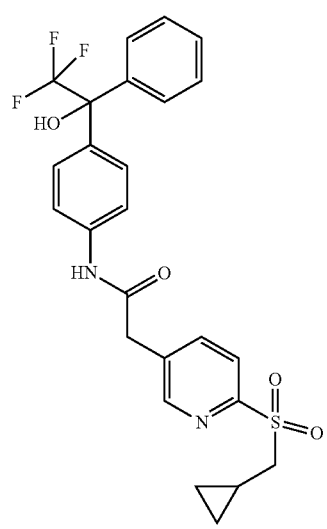

2-[6-(cyclopropylmethylsulfonyl)-3-pyridyl]-N-[4-(2,2,2-trifluoro-1-hydroxy-1-phenyl-ethyl)phenyl]acetamide.
MS(ES$^+$) m/z 505.2 [M+H]$^+$.

(−)-20: (−)-2-[6-(cyclopropylmethylsulfonyl)-3-pyridyl]-N-[4-[1-hydroxy-1-(trifluoromethyl)propyl]phenyl]acetamide Optical rotation: $[\alpha]_D^{20}=-7.31°$ (c=0.2152, DMSO).

(+)-20: (+)-2-[6-(cyclopropylmethylsulfonyl)-3-pyridyl]-N-[4-[1-hydroxy-1-(trifluoromethyl)propyl]phenyl]acetamide Optical rotation: $[\alpha]_D^{20}=+13.56°$ (c=0.2644, DMSO).

21

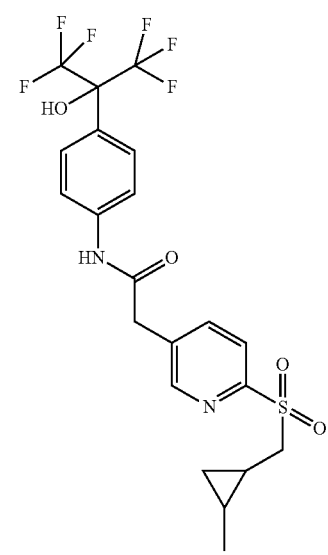

MS(ES$^+$) m/z 511.1 [M + H]$^+$
2-[6-[(2-methylcyclopropyl)methylsulfonyl]-3-pyridyl]-N-[4-[2,2,2-trifluoro-1-hydroxy-1-(trifluoromethyl)ethyl]phenyl]acetamide 1H NMR (400 MHz, DMSO-d6) δ ppm 10.50 (s, 1H) 8.73 (dd, J=2.3, 0.8 Hz, 1H) 8.59 (br s, 1H) 8.10 (dd, J=8.2, 2.3 Hz, 1H) 8.05 (dd, J=8.2, 0.8 Hz, 1H) 7.71 (d, J=9.2 Hz, 2H) 7.61 (br d, J=9.2 Hz, 2H) 3.42 (dd, J=14.7, 6.6 Hz, 1H) 3.38-3.28 (m, 1H) 0.92-0.80 (m, 1H) 0.79 (d, J=6.0 Hz, 2H) 0.65-0.40 (m, 4H) 0.30 (m, 1H) 0.20 (m, 1H).

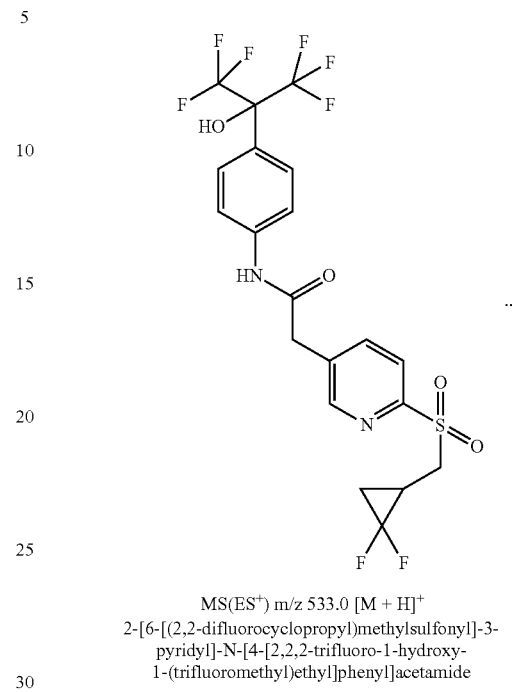

MS(ES$^+$) m/z 533.0 [M + H]$^+$
2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide 1H NMR (400 MHz, DMSO-d6) δ ppm 10.52 (s, 1H) 8.76 (dd, J=2.2, 0.8 Hz, 1H) 8.61 (br s, 1H) 8.11 (dd, J=8.1, 2.2 Hz, 1H) 8.08 (dd, J=8.1, 0.8 Hz, 1H) 7.71 (d, J=9.1 Hz, 2H) 7.61 (br d, J=9.1 Hz, 2H) 3.92 (s, 2H) 3.65 (dd, J=7.6, 2.4 Hz, 2H) 1.92 (m, 1H) 1.70 (m, 1H) 1.31 (m, 1H).

The 2 enantiomers of example 22 were separated by chiral chromatography using a column Chiralpak AD 10 μm, 30×250 mm and a mobile phase, CO$_2$:EtOH:TEA 75:25:0.1, 120 mL/min, with UV detection at 254 nm, and column temperature of 35° C.

Starting from 340 mg of racemate, 116.5 mg of (+)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (first isomer to be eluted) and 119.5 mg of (−)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide were obtained.

(+)-22: (+)-2-[6-[(2,2-difluorocyclopropyl)methyl-sulfonyl]-3-pyridyl]-N-[4-[2,2,2-trifluoro-1-hydroxy-1-(trifluoromethyl)ethyl]phenyl]acetamide Optical rotation: $[\alpha]_D^{20}$=+19.34° (c=0.3872, DMSO).

(−)-22: (−)-2-[6-[(2,2-difluorocyclopropyl)methyl-sulfonyl]-3-pyridyl]-N-[4-[2,2,2-trifluoro-1-hydroxy-1-(trifluoromethyl)ethyl]phenyl]acetamide Optical rotation: $[\alpha]_D^{20}$=−10.14° (c=0.4406, DMSO).

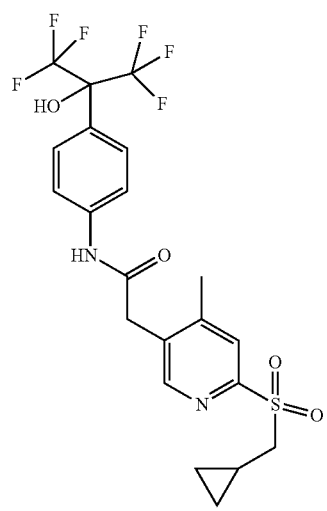

23

2-[6-(cyclopropylmethylsulfonyl)-4-methyl-3-pyridyl]-N-[4-[2,2,2-trifluoro-1-hydroxy-1-(trifluoromethyl)ethyl]phenyl]acetamide.
MS(ES$^+$) m/z 511.1 [M+H]$^+$.

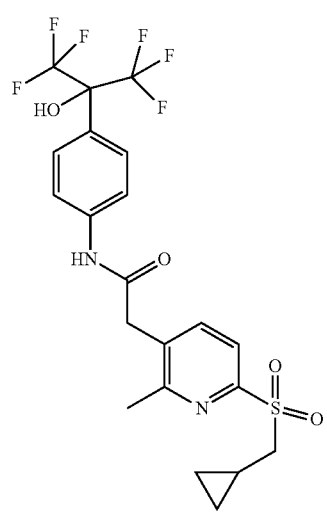

2-[6-(cyclopropylmethylsulfonyl)-2-methyl-3-pyridyl]-N-[4-[2,2,2-trifluoro-1-hydroxy-1-(trifluoromethyl)ethyl]phenyl]acetamide.
MS(ES$^+$) m/z 511.1 [M+H]$^+$.

-continued

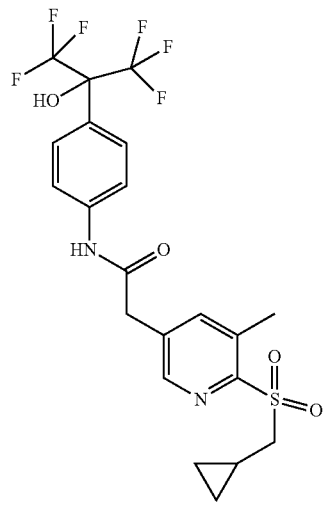

25

2-[6-(cyclopropylmethylsulfonyl)-5-methyl-3-pyridyl]-N-[4-[2,2,2-trifluoro-1-hydroxy-1-(trifluoromethyl)ethyl]phenyl]acetamide.
MS(ES$^+$) m/z 511.1 [M+H]$^+$.

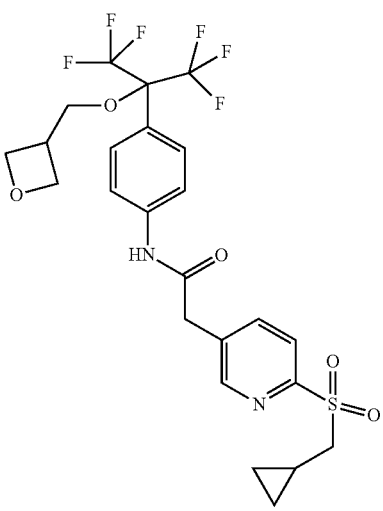

26

2-[6-(cyclopropylmethylsulfonyl)-3-pyridyl]-N-[4-[2,2,2-trifluoro-1-(oxetan-3-ylmethoxy-1-(trifluoromethyl)ethyl]phenyl]acetamide.
MS(ES$^+$) m/z 567.2 [M+H]$^+$.

1H NMR (400 MHz, DMSO-d6) δ ppm 10.60 (s, 1H) 8.73 (d, J=2.3 Hz, 1H) 8.10 (dd, J=8.1, 2.3 Hz, 1H) 8.06 (d, J=8.1 Hz, 1H) 7.80 (d, J=9.0 Hz, 2H) 7.51 (br d, J=9.0 Hz, 2H) 4.67 (dd, J=8.0, 6.2 Hz, 1H) 4.35 (t, J=6.2 Hz, 2H) 3.92 (s, 2H) 3.78 (d, J=6.9 Hz, 2H) 3.39 (d, J=7.3 Hz, 2H) 3.30 (m, 1H) 0.88 (m, 1H) 0.43 (m, 2H) 0.14 (m, 2H).

27

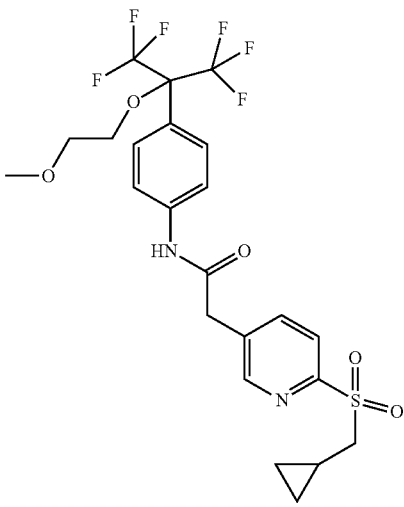

2-[6-(cyclopropylmethylsulfonyl)-3-pyridyl]-N-[4-[2,2,2-trifluoro-1-(2-methoxyethoxy)-1-(trifluoromethyl)ethyl]phenyl]acetamide. MS(ES$^+$) m/z 555.2 [M+H]$^+$.

1H NMR (400 MHz, DMSO-d6) δ ppm 10.59 (s, 1H) 8.72 (dd, J=2.3, 0.8 Hz, 1H) 8.10 (dd, J=8.1, 2.2 Hz, 1H) 8.06 (dd, J=8.1, 0.8 Hz, 1H) 7.78 (d, J=9.0 Hz, 2H) 7.58 (br d, J=9.0 Hz, 2H) 3.92 (s, 2H) 3.68-3.48 (m, 4H) 3.40 (d, J=7.2 Hz, 2H) 3.30 (s, 3H) 0.88 (m, 1H) 0.42 (m, 2H) 0.14 (m, 2H).

Example 28

28

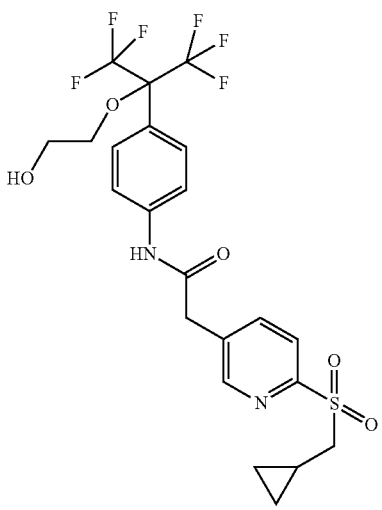

2-[6-(cyclopropylmethylsulfonyl)-3-pyridyl]-N-[4-[2,2,2-trifluoro-1-(2-hydroxyethoxy)-1-(trifluoromethyl)ethyl]phenyl]acetamide i) Following a procedure analogous to that described for Example 1, using the appropriate building blocks II-1 (65 mg) and III-11 (99 mg), the crude product was triturated successively with EtOAc and diisopropyl ether to obtain 65 mg of 2-[6-(cyclopropylmethylsulfonyl)-3-pyridyl]-N-[4-[2,2,2-trifluoro-1-(2-tetrahydropyran-2-yloxyethoxy)-1-(trifluoromethyl)ethyl]phenyl]acetamide. MS(ES$^+$) m/z 647.4 [M+Na]$^+$. ii) To a solution of the product obtained in the previous step (55 mg) in methanol (3 mL) was added PTSA (18 mg). The reaction mixture was stirred at RT for 1.5 hours and then concentrated under reduced pressure. The residue was purified by column chromatography on silica gel, using 60% to 80% EtOAc in heptane as the eluent to obtain 40 mg of the expected compound. MS(ES$^+$) m/z 541.1 [M+H]$^+$.

1H NMR (400 MHz, DMSO-d6) δ ppm 10.58 (s, 1H) 8.73 (dd, J=2.2, 0.8 Hz, 1H) 8.10 (dd, J=8.1, 2.2 Hz, 1H) 8.06 (dd, J=8.1, 0.8 Hz, 1H) 7.77 (d, J=9.1 Hz, 2H) 7.61 (br d, J=9.1 Hz, 2H) 4.92 (t, J=5.6 Hz, 1H) 3.92 (s, 2H) 3.65 (q, J=5.6 Hz, 2H) 3.54 (t, J=5.6 Hz, 2H) 3.39 (d, J=7.3 Hz, 2H) 0.88 (m, 1H) 0.42 (m, 2H) 0.14 (m, 2H).

Examples 29-35

29

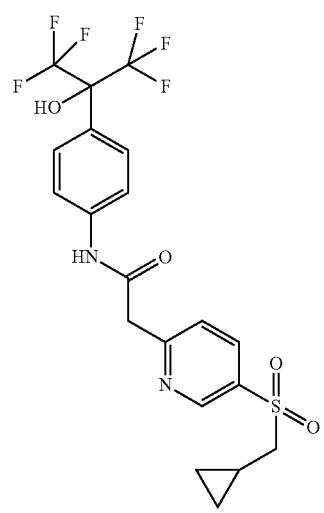

2-[5-(cyclopropylmethylsulfonyl)-2-pyridyl]-N-[4-[2,2,2-trifluoro-1-hydroxy-1-(trifluoromethyl)ethyl]phenyl]acetamide i) To a solution of the building block IV-1 (250 mg) in DMSO (3 mL) were added sodium cyclopropylmethanesulfinate V-1 (113 mg), (+/−)-trans-1,2-diaminocyclohexane (26 µL) and copper(I) trifluoromethanesulfonate benzene complex (46 mg). The resulting mixture was heated to 12500 under microwave irradiation in a sealed tube for 45 minutes. The reaction mixture was poured into water/ether and extracted with ether. The extract was concentrated under reduced pressure, taken up in DCM/water, filtered on a water repellent filter cartridge and concentrated under reduced pressure. The residue was purified by column chromatography on silica gel, using 5% to 100% EtOAc in heptane as the eluent, followed by trituration with ether/pentane to obtain 95 mg of the expected compound. MS(ES$^+$) m/z 497.0 [M+H]$^+$.

1H NMR (400 MHz, DMSO-d6) δ ppm 10.51 (s, 1H) 8.95 (d, J=2.01 Hz, 1H) 8.58 (s, 1H) 8.26 (dd, J=8.16, 2.38 Hz, 1H) 7.68-7.76 (m, 3H) 7.61 (br d, J=8.78 Hz, 2H) 4.05 (s, 2H) 3.32-3.41 (m, 2H) 0.83-0.92 (m, 1H) 0.44-0.50 (m, 2H) 0.09-0.14 (m, 2H).

Following a procedure analogous to that described for Example 29, using the appropriate building blocks IV and V-1, the following compounds were prepared.

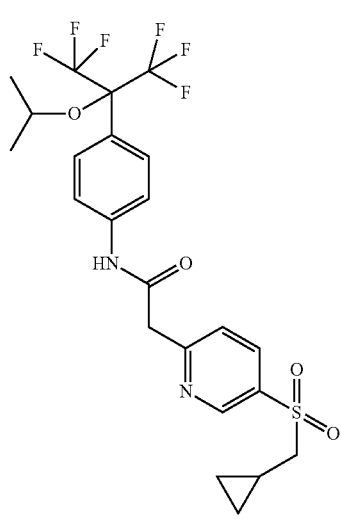

MS(ES⁺) m/z 539.2 [M + H]⁺
2-[5-(cyclopropylmethylsulfonyl)-2-pyridyl]-
N-[4-[2,2,2-trifluoro-1-isopropoxy-1-
(trifluoromethyl)ethyl]phenyl]acetamide 1H NMR (400 MHz, DMSO-d6) δ ppm 10.60 (s, 1H) 8.95 (s, 1H) 8.26 (dd, J=8.28, 2.51 Hz, 1H) 7.78 (d, J=8.11 Hz, 2H) 7.70 (d, J=8.78 Hz, 1H) 7.58 (d, J=8.53 Hz, 2H) 4.05 (s, 2H) 3.93 (dt, J=12.11, 5.87 Hz, 1H) 3.34-3.39 (m, 2H) 1.21 (d, J=6.02 Hz, 6H) 0.83-0.92 (m, 1H) 0.44-0.49 (m, 2H) 0.09-0.13 (m, 2H).

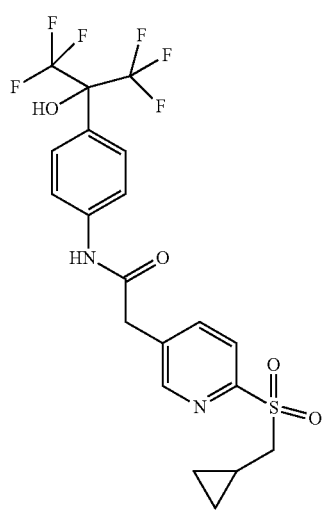

2-[5-(cyclopropylmethylsulfonyl)-2-pyridyl]-N-[3-methyl-4-[2,2,2-
trifluoro-1-hydroxy-1-(trifluoromethyl)ethyl]phenyl]acetamide.
MS(ES⁺) m/z 511.4 [M+H]⁺.

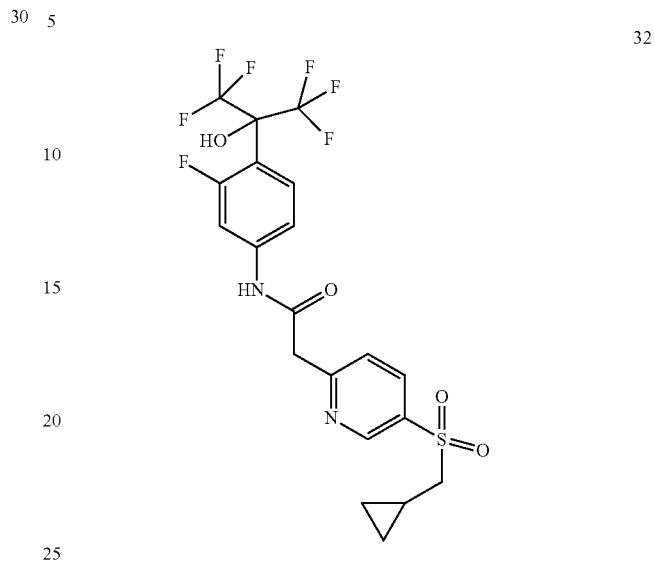

2-[5-(cyclopropylmethylsulfonyl)-2-pyridyl]-N-[3-fluoro-4-[2,2,2-
trifluoro-1-hydroxy-1-(trifluoromethyl)ethyl]phenyl]acetamide.
MS(ES⁺) m/z 515.1 [M+H]⁺.

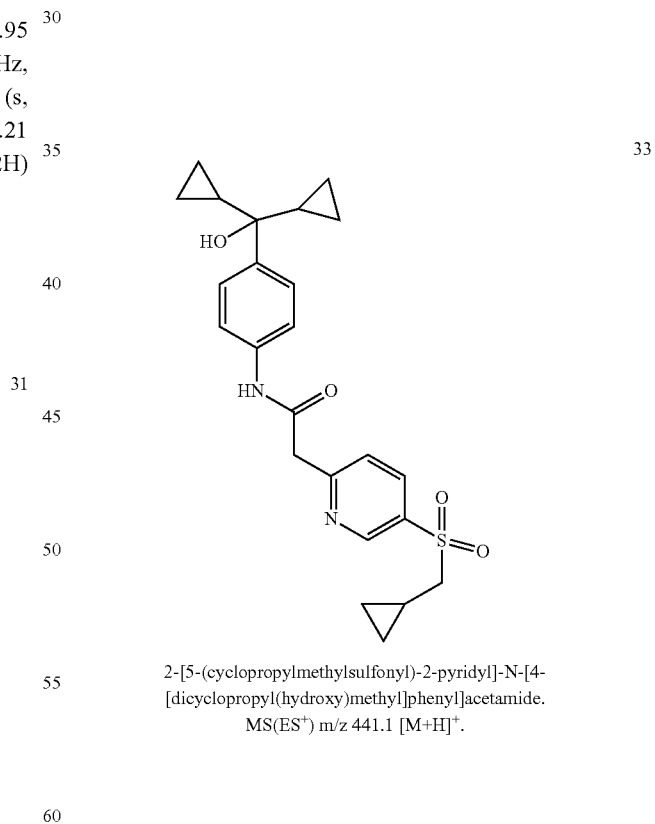

2-[5-(cyclopropylmethylsulfonyl)-2-pyridyl]-N-[4-
[dicyclopropyl(hydroxy)methyl]phenyl]acetamide.
MS(ES⁺) m/z 441.1 [M+H]⁺.

1H NMR (400 MHz, DMSO-d6) δ ppm 10.22 (s, 1H) 8.95 (d, J=1.76 Hz, 1H) 8.25 (dd, J=8.16, 2.38 Hz, 1H) 7.69 (d, J=8.28 Hz, 1H) 7.41-7.54 (m, 4H) 4.30 (s, 1H) 4.00 (s, 2H) 3.33-3.40 (m, 2H) 1.09-1.20 (m, 2H) 0.81-0.96 (m, 1H) 0.44-0.55 (m, 4H) 0.23-0.41 (m, 4H) 0.08-0.22 (m, 4H).

Example 36

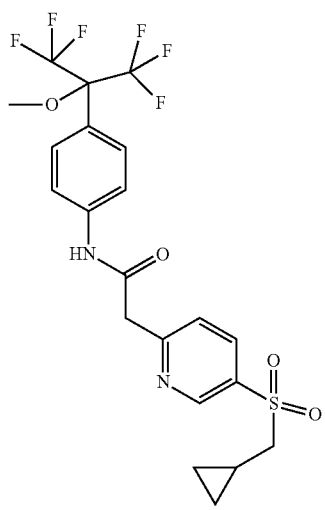

2-[5-(cyclopropylmethylsulfonyl)-2-pyridyl]-N-[4-[2,2,2-trifluoro-1-methoxy-1-(trifluoromethyl)ethyl]phenyl]acetamide.
MS(ES$^+$) m/z 511.2 [M+H]$^+$.

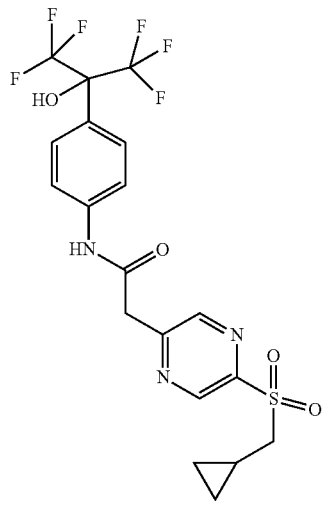

2-[5-cyclopropylmethylsulfonyl)pyrazin-2-yl]-N-[4-[2,2,2-trifluoro-1-hydroxy-1-(trifluoromethyl)ethyl]phenyl]acetamide.

i) To MeOH (5 mL) was added sodium (17 mg). The resulting mixture was stirred until complete dissolution and cyclopropylmethanethiol (64 mg) was added. After stirring for 10 minutes, the building block IV-7 (300 mg) was added. The resulting mixture was heated to 85° C. in a sealed tube for 1 hour, then poured into water/brine and extracted twice with ether. The extract was concentrated under reduced pressure, taken up in DCM/water, filtered on a water repellent filter cartridge and concentrated under reduced pressure to obtain 330 mg of 2-[5-(cyclopropylmethylsulfonyl)pyrazin-2-yl]-N-[4-[2,2,2-trifluoro-1-hydroxy-1-(trifluoromethyl)ethyl]phenyl]acetamide. MS(ES$^+$) m/z 466.0 [M+H]$^+$.

ii) To a cooled (0° C.) solution of the product obtained in the previous step (330 mg) in DCM (20 mL) was added portionwise mCPBA (245 mg). After stirring overnight at RT, additional mCPBA (172 mg) was added. The mixture was concentrated under reduced pressure and purified by column chromatography on silica gel, using 5% to 100% EtOAc in heptane as the eluent to obtain 160 mg of the expected compound. MS(ES$^+$) m/z 498.0 [M+H]$^+$.

1H NMR (400 MHz, DMSO-d6) δ ppm 10.56 (s, 1H) 9.14 (s, 1H) 9.05 (s, 1H) 8.59 (s, 1H) 7.67-7.72 (m, 2H) 7.62 (d, J=8.78 Hz, 2H) 4.15 (s, 2H) 3.37-3.44 (m, 2H) 0.84-0.94 (m, 1H) 0.35-0.41 (m, 2H) 0.05-0.10 (m, 2H).

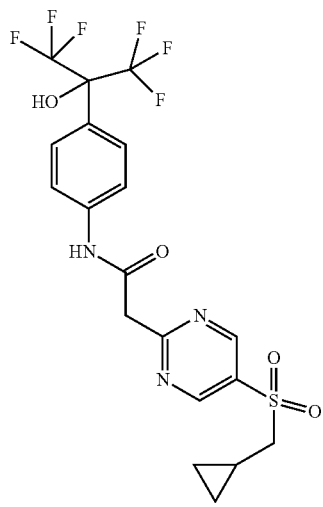

2-[5-(cyclopropylmethylsulfonyl)pyrimidin-2-yl]-N-[4-[2,2,2-trifluoro-1-hydroxy-1-(trifluoromethyl)ethyl]phenyl]acetamide.
MS(ES$^+$) m/z 498.1 [M+H]$^+$.

1H NMR (400 MHz, DMSO-d6) δ ppm 10.53 (s, 1H) 9.20 (s, 2H) 8.59 (s, 1H) 7.72 (d, J=9.1 Hz, 2H) 7.61 (br d, J=9.1 Hz, 2H) 4.20 (s, 2H) 3.48 (d, J=7.2 Hz, 2H) 0.94 (m, 1H) 0.51 (m, 2H) 0.13 (m, 2H).

Example 37

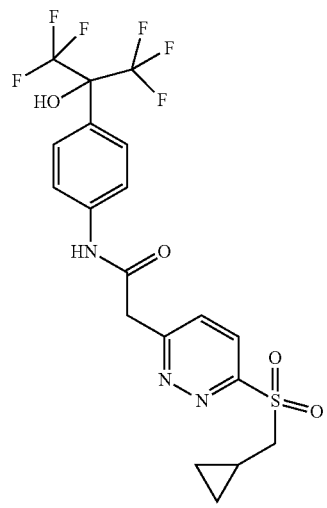

2-[6-cyclopropylmethylsulfonyl)pyridazin-3-yl]-N-[4-[2,2,2-trifluoro-1-hydroxy-1-(trifluoromethyl)ethyl]phenyl]acetamide.

i) To MeOH (5 mL) was added sodium (16 mg). The resulting mixture was stirred until complete dissolution and cyclopropylmethanethiol (62 mg) was added. After stirring for 10 minutes, the building block IV-9 (300 mg) was added. The resulting mixture was heated to 8500 in a sealed tube for 2 hours, then poured into water/brine and extracted twice with ether. The extract was concentrated under reduced pressure, taken up in DCM/water, filtered on a water repellent filter cartridge, concentrated under reduced pressure and purified by column chromatography on silica gel, using 30% to 40% EtOAc in heptane as the eluent to obtain 130 mg of 2-[6-(cyclopropylmethylsulfanyl)pyridazin-3-yl]-N-[4-[2,2,2-trifluoro-1-hydroxy-1-(trifluoromethyl)ethyl]phenyl]acetamide. MS(ES$^+$) m/z 466.1 [M+H]$^+$.

ii) To a cooled (0° C.) solution of the product obtained in the previous step (130 mg) in DCM (13 mL) was added portionwise mCPBA (138 mg). After stirring at 00° C. for 35 minutes, DCM/water was added brine. The aqueous layer was separated and extracted twice with DCM. The combined organic extracts were concentrated under reduced pressure and purified by column chromatography on silica gel to obtain 15 mg of the expected compound. MS(ES$^+$) m/z 498.1 [M+H]$^+$. 1H NMR (400 MHz, DMSO-d6) δ ppm 10.62 (s, 1H) 8.60 (s, 1H) 8.32 (d, J=8.7 Hz, 1H) 8.10 (d, J=8.7 Hz, 1H) 7.72 (d, J=9.2 Hz, 2H) 7.62 (br d, J=9.2 Hz, 2H) 4.30 (s, 2H) 3.59 (d, J=7.3 Hz, 2H) 0.94 (m, 1H) 0.48 (m, 2H) 0.18 (m, 2H).

Example 38

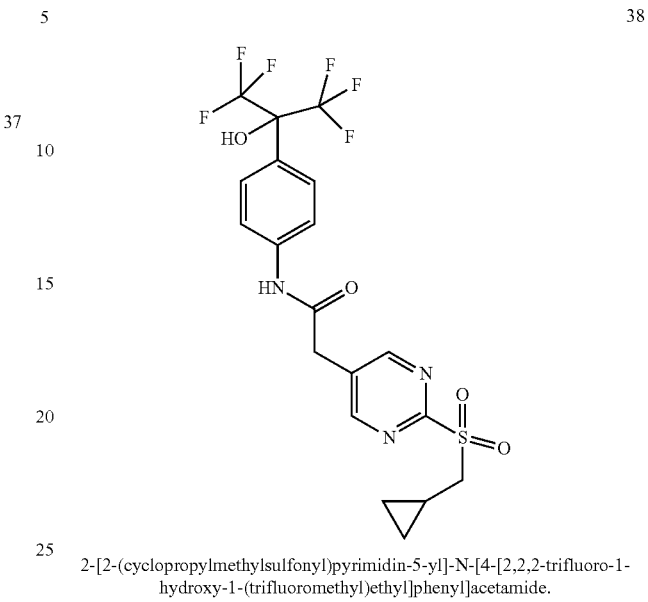

2-[2-(cyclopropylmethylsulfonyl)pyrimidin-5-yl]-N-[4-[2,2,2-trifluoro-1-hydroxy-1-(trifluoromethyl)ethyl]phenyl]acetamide.

i) K$_2$CO$_3$ (723 mg), bromomethylcyclopropane (297 mg) and 1,4,7,10,13,16-hexaoxacyclooctadecane (56 mg) were added to a solution of 5-bromo-1H-pyrimidine-2-thione (400 mg) in toluene (30 mL). The mixture was refluxed for 1 hour, then concentrated under reduced pressure. The residue was taken up in DCM, washed with water, filtered on a water repellent filter cartridge and the filtrate was concentrated under reduced pressure. The residue was purified by column chromatography on silica gel, using 10% EtOAc in heptane as the eluent to obtain 470 mg of 5-bromo-2-(cyclopropylmethylsulfanyl)pyrimidine. MS(ES$^+$) m/z 244.9 [M+H]$^+$.

ii) To a solution of the product obtained in the previous step (470 mg) in anhydrous DMF (4 mL) placed in a microwave tube were added tert-butyl-(1-methoxyvinyloxy)-dimethyl-silane (722 mg) and ZnF$_2$ (99 mg). The reaction mixture was degazed, and Pd(PtBu$_3$)$_2$ (98 mg) was added. The tube was sealed and heated to 100° C. under microwave irradiation for 45 minutes. The reaction mixture was poured onto water, and the aqueous layer was extracted with isopropyl ether. The combined organic extracts were concentrated under reduced pressure, and the residue was taken up in DCM, washed with water, filtered on a water repellent filter cartridge and concentrated under reduced pressure. The residue was purified by column chromatography on silica gel, using 5% to 20% EtOAc in heptane as the eluent to obtain 170 mg of methyl 2-[2-(cyclopropylmethylsulfanyl)pyrimidin-5-yl]acetate. MS(ES$^+$) m/z 239.1 [M+H]$^+$.

iii) NaOH 2N (533 μL) was added to a solution of the product obtained in the previous step (127 mg) in THF (4 mL) and MeOH (1 mL) and the mixture was stirred for 30 minutes at RT. Water and DCM were added, the organic layer was extracted with water, then discarded. The aqueous layer was acidified using HCl 2N (0.6 mL), extracted with DCM, filtered on a water repellent filter cartridge and concentrated under reduced pressure to obtain 115 mg of 2-[2-(cyclopropylmethylsulfanyl)pyrimidin-5-yl]acetic acid. MS(ES$^+$) m/z 225.1 [M+H]$^+$.

iv) To a solution of the product obtained in the previous step (98 mg) in DCM (30 mL) were added 2-(4-aminophenyl)-1,1,1,3,3,3-hexafluoro-propan-2-ol (113 mg), EDCl (85 mg) and DMAP (11 mg). The reaction mixture was stirred at RT for 1 hour, poured onto a mixture of water and DCM, filtered on a water repellent filter cartridge and concentrated under reduced pressure. The residue was purified by column chromatography on silica gel, using 10% to 20% EtOAc in heptane as the eluent to obtain 160 mg of 2-[2-(cyclopropylmethylsulfanyl)pyrimidin-5-yl]-N-[4-[2,2,2-trifluoro-1-hydroxy-1-(trifluoromethyl)ethyl]phenyl]acetamide. MS(ES$^+$) m/z 466.1 [M+H]$^+$.

v) To a cooled (0° C.) solution of the product obtained in the previous step (156 mg) in DCM (30 mL) and THF (1 mL) was added portionwise mCPBA (165 mg). After stirring for 30 minutes, the ice bath was removed and the mixture was allowed to stir an additional 1 h 30. mCPBA (40 mg) was added and stirring was continued during 1 h. A saturated aqueous solution of NaHCO$_3$ (30 mL) was added and the mixture was stirred for 20 minutes. The organic layer was separated, filtered on a water repellent filter cartridge and concentrated under reduced pressure. The residue was purified by column chromatography on silica gel, using 20% EtOAc in heptane as the eluent, followed by trituration in ether/pentane to obtain 135 mg of the expected compound. MS(ES$^+$) m/z 498.1 [M+H]$^+$.

1H NMR (400 MHz, DMSO-d6) δ ppm 10.54 (s, 1H) 9.02 (s, 2H) 8.60 (br s, 1H) 7.71 (d, J=9.1 Hz, 2H) 7.62 (br d, J=9.1 Hz, 2H) 3.97 (s, 2H) 3.55 (d, J=7.3 Hz, 2H) 1.00 (m, 1H) 0.50 (m, 2H) 0.28 (m, 2H).

Example 39

RORγ GAL4 Reporter Gene Assay

Example inhibitors 1-38 were tested for their ability to inhibit RORγ activity in a RORγ GAL4 reporter gene assay. The assay procedure and results are described below.

RORγ GAL4 Reporter Gene Assay Description

A GAL4 one-hybrid reporter system employing luciferase readout was established to determine inhibition of RORγ in 293FT cells. The RORγ ligand-binding domain (LBD) was fused to the yeast GAL4 DNA binding domain (DBD) and placed under the control of the human cytomegalovirus (CMV) immediate early promoter, using expression vector pFN26A (Promega) and standard recombinant DNA cloning methods. To serve as a control in the assay, a similar vector was generated in which the GAL4-DBD was fused to Herpes simplex virus protein 16 (VP16), a constitutive transcriptional activator.

To monitor the inhibitory effect of compounds on RORγ, a transcriptional reporter construct was used. The pGL4.35 vector (Promega) contains nine copies of the GAL4 Upstream Activator Sequence (UAS). This sequence drives the transcription of the luciferase reporter gene luc2P in response to binding of a fusion protein containing the GAL4 DNA binding domain, as for example expressed by the GAL4-RORγ-LBD and GAL4-VP16 expression vectors described above. To allow a GAL4 fusion protein to drive the expression of the luciferase reporter, the pGL4.35 expression vector and the appropriate GAL4 fusion protein expression vector were bulk transfected in the 293FT cells using standard transfection techniques.

The day after transfection, cells were plated into 96 well plates, test compound was added and the plates were incubated overnight. Subsequently, the firefly luciferase activity was quantified using luciferase detection reagent and luminescence readout.

Detailed Assay Description

293FT cells (Invitrogen) were transfected with a GAL4 fusion protein expression vector (as described above) and the transcriptional reporter construct (pGL4.35, Promega). 60 µL of TransIT-293 transfection reagent (Mirus Bio) was added drop wise to 1500 µl Opti-MEM I Reduced Serum Medium (Invitrogen) and incubated at RT (RT) for 5 to 20 minutes. 1500 µL of this reagent mixture was added to 5 µg of GAL4 fusion protein expression vector and 5 µg of the transcriptional reporter construct, and incubated at RT for 20 minutes.

To harvest 293FT cells from a T75 flask, first the culture medium was taken off the cells. Subsequently, the cells were washed with Phosphate Buffered Saline (PBS) (Lonza), after which the PBS was removed. To dissociate the cells, 1 ml of TrypLE Express (Invitrogen) was added to the flask, followed by incubation at RT until the cells visually started to detach. Cells were collected in 5 mL of assay medium (DMEM culture medium (Lonza), 10% dialyzed FBS (Invitrogen) and Pen/Strep (Lonza)) to achieve a single cell suspension. 10×10$^6$ cells were spun down and re-suspended in 10 mL of assay medium. Subsequently, the cell suspension was added to the transfection mix tube, and then transferred as a whole to a T75 flask (Greiner), followed by overnight (16-24 hours) incubation at 37° C. and 5% CO$_2$.

For compound screening, the cells were harvested (as described above) and counted. 13×10$^6$ cells were spun down, the supernatant was aspirated and the cells were re-suspended in 17.3 mL of assay medium obtaining a cell suspension of 0.75×10$^6$ cells/mL. 80 µL of cell suspension (60,000 cells) was plated per well into a white, flat bottom, tissue culture treated, 96 well screening plates (Greiner).

Test compounds were diluted, starting from a 10 mM dimethylsulfoxide (DMSO) stock solution, to serial dilutions in DMSO at 500× the final test concentration. Subsequently, these solutions were diluted to 5× the final test concentration in two 10-fold-dilution steps in assay medium. The final DMSO concentration of the 5× test compound solution was 1%. 20 µL of the 5× test compound solution was added to each test well of the 96 well plate previously plated with 80 µl cell suspension, resulting in the final test concentration with 0.2% DMSO.

The plates were incubated overnight (16-24 hours) at 37° C. and 5% CO$_2$.

For the luciferase readout, the luciferase reagent (Britelite Plus, Perkin Elmer) was brought to RT. To each test well of the screening plates, 100 µL of 2.5-fold diluted Britelite Plus reagent was added, followed by incubation at RT for 10 minutes. The luciferase luminescence signal was measured using a Wallac Victor Microplate Reader (Perkin Elmer).

The half maximum inhibitory concentration (IC$_{50}$) values for the test compounds were calculated from the luciferase signal using GraphPad Prism software (GraphPad Software).

All exemplified compounds of Formula I (Examples 1-39) are expected to have mean pIC$_{50}$ values around or above 5.

Examples 1, 2, 3, 4, 5, 6, 7, 8, 9, 10, 11, 12, 13, 14, 15, 16, 18, 19, 20, (−)-20, (+)-20, (−)-22, 23, 24, 26, 27, 28, 29, 30, 33, 34, 35, 37 and 38 were found to have mean pIC$_{50}$ values above or equal to 6.

Examples 1, 2, 3, 4, 5, 8, 12, 19, 27, 29, 30 and 34 were found to have mean pIC$_{50}$ values above or equal to 7.

The invention claimed is:
1. A compound according to Formula I

(Formula I)

Meta or para or a pharmaceutically acceptable salt thereof wherein:
$A_{11}$-$A_{14}$ are N or $CR_{11}$, $CR_{12}$, $CR_{13}$, $CR_{14}$, respectively, with the proviso that no more than two of the four positions A in $A_{11}$-$A_{14}$ can be simultaneously N;
$A_6$, $A_7$, $A_8$, $A_9$, $A_{10}$ are N or $CR_6$, $CR_7$, $CR_8$, $CR_9$, $CR_{10}$, respectively, with the proviso that at least one but no more than two of the five positions A in $A_6$, $A_7$, $A_8$, $A_9$, $A_{10}$ is N;
$R_1$ is C(2-6)alkyl, C(3-6)cycloalkyl, C(3-6)cycloalkylC(1-3)alkyl, (di)C(3-6)cycloalkylamino or (di)(C(3-6)cycloalkylC(1-3)alkyl)amino, with all carbon atoms of alkyl groups optionally substituted with one or more F and all carbon atoms of cycloalkyl groups optionally substituted with one or more F or methyl;
$R_2$ and $R_3$ are independently H, F, methyl, ethyl, hydroxy, methoxy or $R_2$ and $R_3$ together is carbonyl, all alkyl groups, if present, optionally being substituted with one or more F;
$R_4$ is H or C(1-6)alkyl;
$R_5$ is H, hydroxyethyl, methoxyethyl, C(1-6)alkyl, C(6-10)aryl, C(6-10)arylC(1-3)alkyl, C(1-9)heteroaryl, C(1-9)heteroarylC(1-3)alkyl, C(3-6)cycloalkyl, C(3-6)cycloalkylC(1-3)alkyl, C(2-5)heterocycloalkyl or C(2-5)heterocycloalkylC(1-3)alkyl, all groups optionally substituted with one or more F, C(1-2)alkoxy or cyano;
the sulfonyl group with $R_1$ is represented by one of $R_7$, $R_8$ or $R_9$;
the remaining $R_6$-$R_{14}$ are independently H, halogen, amino, C(1-3)alkoxy, (di)C(1-3)alkylamino or C(1-6)alkyl, all of the alkyl groups optionally being substituted with one or more F; and
$R_{15}$ is H, C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, C(1-2)alkoxy or cyano;
and $R_{16}$ is C(1-6)alkyl, C(3-6)cycloalkyl, C(3-6)cycloalkylC(1-3)alkyl, C(6-10)aryl, C(6-10)arylC(1-3)alkyl, C(1-9)heteroaryl, C(1-9)heteroarylC(1-3)alkyl, C(2-5)heterocycloalkyl or C(2-5)heterocycloalkyl-C(1-3)alkyl, all groups optionally substituted with one or more F, C(1-2)alkyl, C(1-2)alkoxy or cyano.

2. The compound according to claim 1 wherein:
$A_{11}$-$A_{14}$ are N or $CR_{11}$, $CR_{12}$, $CR_{13}$, $CR_{14}$, respectively, with the proviso that no more than two of the four positions A in $A_{11}$-$A_{14}$ can be simultaneously N;
$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;
$A_8$ is $CR_8$;
$R_1$ is C(3-6)cycloalkylC(1-3)alkyl or (di)C(3-6)cycloalkylamino with all carbon atoms of alkyl groups optionally substituted with one or more F and all carbon atoms of cycloalkyl groups optionally substituted with one or more F or methyl;
$R_2$ and $R_3$ are independently H;
$R_4$ is H;
$R_5$ is H, hydroxyethyl, methoxyethyl, C(1-6)alkyl, C(2-5)heterocycloalkyl or C(2-5)heterocycloalkylC(1-3)alkyl, all groups optionally substituted with one or more F, C(1-2)alkoxy or cyano;
the sulfonyl group with $R_1$ is represented by $R_8$;
the remaining $R_6$-$R_{14}$ are independently H, halogen, C(1-3)alkoxy or C(1-6)alkyl, all of the alkyl groups optionally being substituted with one or more F or hydroxy; and
$R_{15}$ is C(1-6)alkyl or C(3-6)cycloalkyl, all groups optionally substituted with one or more F, C(1-2)alkoxy or cyano;
and $R_{16}$ is C(1-6)alkyl, C(3-6)cycloalkyl, C(3-6)cycloalkylC(1-3)alkyl, C(6-10)aryl, C(2-5)heterocycloalkyl or C(2-5)heterocycloalkyl-C(1-3)alkyl, all groups optionally substituted with one or more F, C(1-2)alkyl, C(1-2)alkoxy or cyano.

3. The compound according to claim 1 wherein:
$A_{11}$-$A_{14}$ are respectively $CR_{11}$, $CR_{12}$, $CR_{13}$, $CR_{14}$;
$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;
$A_8$ is $CR_8$;
$R_1$ is C(3-6)cycloalkylC(1-3)alkyl, all carbon atoms of cycloalkyl groups optionally substituted with one or more F or methyl;
$R_2$ and $R_3$ are independently H;
$R_4$ is H;
$R_5$ is H, hydroxyethyl, methoxyethyl, C(1-6)alkyl or C(2-5)heterocycloalkylC(1-3)alkyl;
the sulfonyl group with $R_1$ is represented by $R_8$;
the remaining $R_6$-$R_{14}$ are independently H, halogen, C(1-3)alkoxy or C(1-6)alkyl, all carbon atoms of alkyl groups optionally substituted with one hydroxy;
$R_{15}$ is C(1-6)alkyl or C(3-6)cycloalkyl, all carbon atoms of the alkyl groups optionally substituted with one or more F;
and R16 is C(1-6)alkyl, C(3-6)cycloalkyl, C(3-6)cycloalkylC(1-3)alkyl or C(6-10)aryl, all carbon atoms of the alkyl groups optionally substituted with one or more F.

4. The compound according to claim 1 wherein:
$A_{11}$ or $A_{14}$ is N, the remaining position A being $CR_{11}$ or $CR_{14}$;
$A_{12}$ and $A_{13}$ are respectively $CR_{12}$ and $CR_{13}$;
$A_6$, $A_7$, $A_9$, $A_{10}$ are N or $CR_6$, $CR_7$, $CR_9$, $CR_{10}$, respectively, with the proviso that at least one but no more than two of the four positions A in $A_6$, $A_7$, $A_9$, $A_{10}$ is N;
$A_8$ is $CR_8$;
$R_1$ is C(3-6)cycloalkylC(1-3)alkyl;

R$_2$ and R$_3$ are independently H;
R$_4$ is H;
R$_5$ is H;
the sulfonyl group with R$_1$ is represented by R$_8$;
the remaining R$_6$-R$_{14}$ are independently H;
R$_{15}$ is C(1-6)alkyl, all carbon atoms of alkyl groups optionally substituted with one or more F;
and R$_{16}$ is C(1-6)alkyl, all carbon atoms of alkyl groups optionally substituted with one or more F.

5. The compound as defined in claim 1 which is selected from the group of:

2-[6-(cyclopropylmethylsulfonyl)-3-pyridyl]-N-[4-[2,2,2-trifluoro-1-hydroxy-1-(trifluoromethyl)ethyl]phenyl]acetamide;

2-[6-(cyclopropylmethylsulfonyl)-3-pyridyl]-N-[4-[2,2,2-trifluoro-1-methoxy-1-(trifluoromethyl)ethyl]phenyl]acetamide;

2-[6-(cyclopropylmethylsulfonyl)-3-pyridyl]-N-[3-methyl-4-[2,2,2-trifluoro-1-hydroxy-1-(trifluoromethyl)ethyl]phenyl]acetamide;

2-[6-(cyclopropylmethylsulfonyl)-3-pyridyl]-N-[3-fluoro-4-[2,2,2-trifluoro-1-hydroxy-1-(trifluoromethyl)ethyl]phenyl]acetamide;

N-[3-chloro-4-[2,2,2-trifluoro-1-hydroxy-1-(trifluoromethyl)ethyl]phenyl]-2-[6-(cyclopropylmethylsulfonyl)-3-pyridyl]acetamide;

2-[6-(cyclopropylmethylsulfonyl)-3-pyridyl]-N-[3-methoxy-4-[2,2,2-trifluoro-1-hydroxy-1-(trifluoromethyl)ethyl]phenyl]acetamide;

2-[6-(cyclopropylmethylsulfonyl)-3-pyridyl]-N-[2-methyl-4-[2,2,2-trifluoro-1-hydroxy-1-(trifluoromethyl)ethyl]phenyl]acetamide;

2-[6-(cyclopropylmethylsulfonyl)-3-pyridyl]-N-[2-fluoro-4-[2,2,2-trifluoro-1-hydroxy-1-(trifluoromethyl)ethyl]phenyl]acetamide;

2-[6-(cyclopropylmethylsulfonyl)-3-pyridyl]-N-[2-methoxy-4-[2,2,2-trifluoro-1-hydroxy-1-(trifluoromethyl)ethyl]phenyl]acetamide;

2-[6-(cyclopropylmethylsulfonyl)-3-pyridyl]-N-[5-[2,2,2-trifluoro-1-hydroxy-1-(trifluoromethyl)ethyl]-2-pyridyl]acetamide;

2-[6-(cyclopropylmethylsulfonyl)-3-pyridyl]-N-[4-[1-hydroxy-1-(trifluoromethyl)butyl]phenyl]acetamide;

2-[6-(cyclopropylmethylsulfonyl)-3-pyridyl]-N-[4-[1-hydroxy-3-methyl-1-(trifluoromethyl)butyl]phenyl]acetamide;

2-[6-(cyclopropylmethylsulfonyl)-3-pyridyl]-N-[4-[1-hydroxy-4-methyl-1-(trifluoromethyl)pentyl]phenyl]acetamide;

N-[4-(1-cyclopentyl-2,2,2-trifluoro-1-hydroxy-ethyl)phenyl]-2-[6-(cyclopropylmethylsulfonyl)-3-pyridyl]acetamide;

N-[4-[1-(cyclopentylmethyl)-2,2,2-trifluoro-1-hydroxy-ethyl]phenyl]-2-[6-(cyclopropylmethylsulfonyl)-3-pyridyl]acetamide;

N-[4-[1-(cyclohexylmethyl)-2,2,2-trifluoro-1-hydroxy-ethyl]phenyl]-2-[6-(cyclopropylmethylsulfonyl)-3-pyridyl]acetamide;

2-[6-(cyclopropylmethylsulfonyl)-3-pyridyl]-N-[5-(2,2,2-trifluoro-1-hydroxy-1-methyl-ethyl)-2-pyridyl]acetamide;

2-[6-(cyclopropylmethylsulfonyl)-3-pyridyl]-N-[4-[dicyclopropyl(hydroxy)methyl]phenyl]acetamide;

2-[6-(cyclopropylmethylsulfonyl)-3-pyridyl]-N-[4-(2,2,2-trifluoro-1-hydroxy-1-phenyl-ethyl)phenyl]acetamide;

2-[6-(cyclopropylmethylsulfonyl)-3-pyridyl]-N-[4-[1-hydroxy-1-(trifluoromethyl)propyl]phenyl]acetamide (racemate);

(−)-2-[6-(cyclopropylmethylsulfonyl)-3-pyridyl]-N-[4-[2,2,2-trifluoro-1-hydroxy-1-(trifluoromethyl)ethyl]phenyl]acetamide (levogyre enantiomer);

(+)-2-[6-(cyclopropylmethylsulfonyl)-3-pyridyl]-N-[4-[2,2,2-trifluoro-1-hydroxy-1-(trifluoromethyl)ethyl]phenyl]acetamide (dextrogyre enantiomer);

2-[6-[(2-methylcyclopropyl)methylsulfonyl]-3-pyridyl]-N-[4-[2,2,2-trifluoro-1-hydroxy-1-(trifluoromethyl)ethyl]phenyl]acetamide;

2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (racemate);

(+)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (dextrogyre enantiomer);

(−)-2-[6-[(2,2-difluorocyclopropyl)methylsulfonyl]-3-pyridyl]-N-[4-[2,2,2-trifluoro-1-hydroxy-1-(trifluoromethyl)ethyl]phenyl]acetamide (levogyre enantiomer);

2-[6-(cyclopropylmethylsulfonyl)-4-methyl-3-pyridyl]-N-[4-[2,2,2-trifluoro-1-hydroxy-1-(trifluoromethyl)ethyl]phenyl]acetamide;

2-[6-(cyclopropylmethylsulfonyl)-2-methyl-3-pyridyl]-N-[4-[2,2,2-trifluoro-1-hydroxy-1-(trifluoromethyl)ethyl]phenyl]acetamide;

2-[6-(cyclopropylmethylsulfonyl)-5-methyl-3-pyridyl]-N-[4-[2,2,2-trifluoro-1-hydroxy-1-(trifluoromethyl)ethyl]phenyl]acetamide;

2-[6-(cyclopropylmethylsulfonyl)-3-pyridyl]-N-[4-[2,2,2-trifluoro-1-(oxetan-3-ylmethoxy)-1-(trifluoromethyl)ethyl]phenyl]acetamide;

2-[6-(cyclopropylmethylsulfonyl)-3-pyridyl]-N-[4-[2,2,2-trifluoro-1-(2-methoxyethoxy)-1-(trifluoromethyl)ethyl]phenyl]acetamide;

2-[6-(cyclopropylmethylsulfonyl)-3-pyridyl]-N-[4-[2,2,2-trifluoro-1-(2-hydroxyethoxy)-1-(trifluoromethyl)ethyl]phenyl]acetamide;

2-[5-(cyclopropylmethylsulfonyl)-2-pyridyl]-N-[4-[2,2,2-trifluoro-1-hydroxy-1-(trifluoromethyl)ethyl]phenyl]acetamide;

2-[5-(cyclopropylmethylsulfonyl)-2-pyridyl]-N-[4-[2,2,2-trifluoro-1-isopropoxy-1-(trifluoromethyl)ethyl]phenyl]acetamide;

2-[5-(cyclopropylmethylsulfonyl)-2-pyridyl]-N-[3-methyl-4-[2,2,2-trifluoro-1-hydroxy-1-(trifluoromethyl)ethyl]phenyl];

2-[5-(cyclopropylmethylsulfonyl)-2-pyridyl]-N-[3-fluoro-4-[2,2,2-trifluoro-1-hydroxy-1-(trifluoromethyl)ethyl]phenyl]acetamide;

2-[5-(cyclopropylmethylsulfonyl)-2-pyridyl]-N-[4-[dicyclopropyl(hydroxy)methyl]phenyl]acetamide;

2-[5-(cyclopropylmethylsulfonyl)-2-pyridyl]-N-[4-[2,2,2-trifluoro-1-methoxy-1-(trifluoromethyl)ethyl]phenyl]acetamide;

2-[5-(cyclopropylmethylsulfonyl)pyrimidin-2-yl]-N-[4-[2,2,2-trifluoro-1-hydroxy-1-(trifluoromethyl)ethyl]phenyl]acetamide;

2-[5-(cyclopropylmethylsulfonyl)pyrazin-2-yl]-N-[4-[2,2,2-trifluoro-1-hydroxy-1-(trifluoromethyl)ethyl]phenyl]acetamide;

2-[6-(cyclopropylmethylsulfonyl)pyridazin-3-yl]-N-[4-[2,2,2-trifluoro-1-hydroxy-1-(trifluoromethyl)ethyl]phenyl]

2-[2-(cyclopropylmethylsulfonyl)pyrimidin-5-yl]-N-[4-[2,2,2-trifluoro-1-hydroxy-1-(trifluoromethyl)ethyl]phenyl]acetamide.

6. A compound according to claim 1 or a pharmaceutically acceptable salt thereof for use in therapy.

7. The compound according to claim 1 or a pharmaceutically acceptable salt thereof for the treatment of ROR γ-mediated diseases or conditions.

8. A medicament according to claim 1 or a pharmaceutically acceptable salt thereof.

9. A pharmaceutical composition which comprises a compound of Formula I according to claim 1 or a pharmaceutically acceptable salt thereof and one or more pharmaceutically acceptable excipients.

10. The pharmaceutical composition according to claim 9, which further comprises at least one additional therapeutically active agent.

* * * * *